(12) United States Patent
Ping et al.

(10) Patent No.: US 7,223,778 B2
(45) Date of Patent: May 29, 2007

(54) 5-SUBSTITUTED-2-ARYLPYRIDINES

(75) Inventors: Ge Ping, Durham, CT (US); Taeyoung Yoon, Guilford, CT (US); Lu Yan Zhang, Branford, CT (US); Raymond F. Horvath, Guilford, CT (US)

(73) Assignee: Neurogen Corporation, Branford, CT (US)

( * ) Notice: Subject to any disclaimer, the term of this patent is extended or adjusted under 35 U.S.C. 154(b) by 645 days.

(21) Appl. No.: 10/154,396

(22) Filed: May 22, 2002

(65) Prior Publication Data

US 2003/0152520 A1 Aug. 14, 2003

Related U.S. Application Data

(60) Provisional application No. 60/292,703, filed on May 22, 2001.

(51) Int. Cl.
  *C07D 213/02* (2006.01)
  *A61K 31/44* (2006.01)
(52) U.S. Cl. ............ 514/352; 514/349; 514/353; 546/297; 546/304; 546/307
(58) Field of Classification Search ............ 546/292, 546/297, 298, 299, 300, 301, 302, 305, 304, 546/307; 514/346, 348, 349, 351, 352, 353
See application file for complete search history.

(56) References Cited

U.S. PATENT DOCUMENTS

| 3,546,237 | A |   | 12/1970 | Doyle et al. |          |
|-----------|---|---|---------|--------------|----------|
| 3,673,198 | A |   | 6/1972  | Doyle et al. |          |
| 5,185,339 | A | * | 2/1993  | Pilkington et al. | 514/256 |
| 5,629,428 | A | * | 5/1997  | Schlosser et al. | 546/303 |
| 5,783,522 | A |   | 7/1998  | Schaefer et al. |         |
| 5,849,758 | A | * | 12/1998 | Kleemann et al. | 514/269 |
| 6,165,941 | A |   | 12/2000 | Schaefer et al. |         |

FOREIGN PATENT DOCUMENTS

| DE | 19748439 A1 | * | 5/1999 |
|----|-------------|---|--------|
| WO | WO 95/33750 |   | 12/1995 |
| WO | WO 01/60806 A2 |   | 8/2001 |
| WO | WO 01/68614 A2 |   | 9/2001 |

OTHER PUBLICATIONS

Caplus 122:213937.*
Caplus 71:38813.*
Caplus 91:140754.*
Caplus 85:142218.*
Caplus 81:105345.*
Caplus 124:274627.*
Iwamoto et al, Heterocycles, vol. 43, No. 1, pp. 199-204, 1996.*
McCarthy et al., "Recent Advances with the $CRF_1$ Receptor: Design of Small Molecule Inhibitors, Receptor Subtypes and Clinical Indications," *Current Pharmaceutical Design* 5:289-315 (1999).
O'Neill et al., "Total Synthesis of (±)-Cytisine," *Organic Letters* 2:4201-4204 (2000).
Vernin et al., "14. Etude en serie triazenique. $IV^1$) $^2$). Synthese et reactivite d'aryl-3-(dimethyl-3,4-isoxazolyl-5)-1-triazenes et d'arylazo-4-dimethyl-3,4-isoxazolones-5," Helvetica Chimica Acta, vol. 62, Fasc. 5:1570-1585, (1979) Nr. 164.
Abramovitch et al., "Reaction of Pyridine 1-Oxides with Benzyne, β-Hydroxyarylation of Pyridines *via* [σ2s + π2a + π4s] Rearrangements," Communications to the Editor, Journal of the American Chemical Society, 96:16, 5265-5267 (1974).
Lyle et al., "Regioselective Nucleophilic Addition to 3,4,-Lutidine," J. Org. Chem., vol. 41, No. 20 3250-3252 (1976).

* cited by examiner

*Primary Examiner*—Zinna N. Davis
(74) *Attorney, Agent, or Firm*—Edwards Angell Palmer & Dodge LLP; Peter F. Corless; Dwight D. Kim

(57) ABSTRACT

Novel 5-substituted-2-arylpyridine compounds are provided. Such compounds can act as selective modulators of CRF receptors. The 5-substituted-2-arylpyridine compounds provided herein are useful in the treatment of a number of CNS and periphereal disorders, particularly stress, anxiety, depression, cardiovascular disorders, and eating disorders. Methods of treatment of such disorders and well as packaged pharmaceutical compositions are also provided.

Compounds provided are also useful as probes for the localization of CRF receptors and as standards in assays for CRF receptor binding. Methods of using the compounds in receptor localization studies are given.

29 Claims, No Drawings

5-SUBSTITUTED-2-ARYLPYRIDINES

This application claims the benefit of U.S. Provisional Application Ser. No. 60/292,703 filed May 22, 2001, the teachings of which are incorporated herein by reference.

BACKGROUND

1. Field of the Invention

The present invention relates to 5-substituted-2-arylpyridine compounds. Such compounds bind with high selectivity and/ or high affinity to CRF1 receptors (Corticotropin Releasing Factor 1 Receptors). Preferred compounds block, inhibit, activate, or otherwise modulate the activity of the receptors to which they bind. This invention also relates to pharmaceutical compositions comprising such compounds and to the use of such compounds in treatment of psychiatric disorders and neurological diseases, including major depression, anxiety-related disorders, post-traumatic stress disorder, supranuclear palsy and feeding disorders, as well as treatment of immunological, cardiovascular or heart-related diseases, irritable bowel syndrome, and colonic hypersensitivity associated with psychopathological disturbance and stress. Additionally this invention relates to the use such compounds as probes for the localization of CRF1 receptors in cells and tissues.

2. Background of the Invention

Corticotropin releasing factor (CRF), a 41 amino acid peptide, is the primary physiological regulator of proopiomelanocortin (POMC) derived peptide secretion from the anterior pituitary gland. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain. There is also evidence that CRF plays a significant role in integrating the response of the immune system to physiological, psychological, and immunological stressors.

CRF acts by binding to and modulating the signal transduction activities of specific cell surface receptors, including CRF1 receptors and CRF2 receptors. These receptors are found at high concentrations in the central nervous system (CNS), particularly in certain regions of the brain. CRF1 receptors are also found outside the CNS.

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system.

In affective disorder, or major depression, the concentration of CRF is significantly increased in the cerebral spinal fluid (CSF) of drug-free individuals. Furthermore, the density of CRF receptors is significantly decreased in the frontal cortex of suicide victims, consistent with a hypersecretion of CRF. In addition, there is a blunted adrenocorticotropin (ACTH) response to CRF (i.v. administered) observed in depressed patients. Preclinical studies in rats and non-human primates provide additional support for the hypothesis that hypersecretion of CRF may be involved in the symptoms seen in human depression. There is also preliminary evidence that tricyclic antidepressants can alter CRF levels and thus modulate the numbers of CRF receptors in brain.

The mechanisms and sites of action through which conventional anxiolytics and antidepressants produce their therapeutic effects remain to be fully elucidated. It has been hypothesized however, that they are involved in the suppression of CRF hypersecretion that is observed in these disorders.

CRF has been implicated in the etiology of anxiety-related disorders. CRF produces anxiogenic effects in animals and interactions between benzodiazepine/non-benzodiazepine anxiolytics and CRF have been demonstrated in a variety of behavioral anxiety models. Preliminary studies using the putative CRF receptor antagonist α-helical ovine CRF (9–41) in a variety of behavioral paradigms demonstrate that the antagonist produces "anxiolytic-like" effects that are qualitatively similar to the benzodiazepines. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test and in the acoustic startle test in rats. The benzodiazepine receptor antagonist Ro 15-1788, which was without behavioral activity alone in the operant conflict test, reversed the effects of CRF in a dose-dependent manner, while the benzodiazepine inverse agonist FG 7142 enhanced the actions of CRF.

CRF activity has also been implicated in the pathogeneisis of certain cardiovascular or heart-related, digestive, degenerative, dermatological, and immunological, diseases and disorders such as hypertension, tachycardia and congestive heart failure, stroke, acne and osteoporosis, as well as in premature birth, psychosocial dwarfism, stress-induced fever, ulcer, diarrhea, post-operative ileus and colonic hypersensitivity, e.g., associated with psychopathological disturbance and stress.

SUMMARY OF THE INVENTION

The invention provides novel compounds of Formula I (shown below). The invention also comprises pharmaceutical compositions comprising compounds of Formula I and at least one pharmaceutically acceptable carrier or excipient. Such 5-substituted-2-arylpyridines bind to cell surface receptors, preferably G-coupled protein receptors, especially CRF receptors and most preferably CRF1 receptors. Preferred compounds of Formula I exhibit high affinity for CRF1 receptors, i.e., they bind to, activate, inhibit, or otherwise modulate the activity of receptors other than CRF receptors with affinity constants of less than 1 micromolar, preferably less than 100 nanomolar, and most preferably less than 10 nanomolar. Additionally, preferred compounds of Formula I also exhibit high sselectivity for CRF1 receptors.

The invention further comprises methods of treating patients suffering from certain diseases or disorders by administering to such patients an amount of a compound of Formula I effective to reduce signs or symptoms of the disease or disorder. These diseases and disorders include CNS disorders, particularly affective disorders, anxiety, stress, depression, and eating disorders and also include certain digestive disorders, particularly irritable bowel syndrome and Crohn's disease. These diseases or disorders further include cardiovascular or heart-related, digestive, degenerative, dermatological, and immunological, diseases and disorders such as hypertension, tachycardia and congestive heart failure, stroke, acne and osteoporosis, as well as premature birth, psychosocial dwarfism, stress-induced fever, ulcer, diarrhea, post-operative ileus and colonic hypersensitivity. The patient suffering from such diseases or disorders may be a human or other animal (preferably a mammal), such as a domesticated companion animal (pet) or a livestock animal.

According to yet another aspect, the present invention provides pharmaceutical compositions comprising a compound of Formula I or pharmaceutically acceptable salts or solvates thereof together with at least one pharmaceutically acceptable carrier or excipient, which compositions are useful for the treatment of the disorders recited above. The invention further provides methods of treating patients suffering from any of these disorders with an effective amount of a compound or composition of Formula I.

Additionally this invention relates to the use of labeled compounds of Formula I (particularly radiolabeled compounds of this invention) as probes for the localization of receptors in cells and tissues and as standards and reagents for use in determining the receptor-binding characteristics of test compounds.

Thus, in a first aspect, the invention is directed to compounds of Formula I

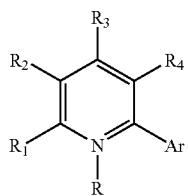

Formula I and the pharmaceutically acceptable salts thereof.

Ar is phenyl, 1-naphthyl or 2-naphthyl, each of which is mono-, di-, or tri-substituted, or Ar is mono-, di-, or tri-substituted heteroaryl, said heteroaryl having from 1 to 3 rings, 5 to 7 ring members in each ring and from 1 to about 3 heteroatoms in at least one of said rings.

R is oxygen or absent.

$R_2$ is optionally substituted alkyl, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono or dialkylcarboxamide, optionally substituted aryl or optionally substituted heteroaryl, said heteroaryl having from 1 to 3 rings, 5 to 7 ring members in each ring and from 1 to about 3 heteroatoms in at least one of said rings.

$R_1$, $R_3$, and $R_4$ are independently chosen from hydrogen, halogen, nitro, optionally substituted alkyl, optionally substituted alkenyl, optionally substituted alkynyl, optionally substituted alkoxy, optionally substituted mono- or di-alkylamino, optionally substituted cycloalkyl, optionally substituted (cycloalkyl)alkyl, optionally substituted (cycloalkyl)oxy, optionally substituted (cycloalkyl)alkoxy, optionally substituted alkylthio, optionally substituted alkylsulfinyl, optionally substituted alkylsulfonyl, and optionally substituted mono- or dialkylcarboxamide.

Not all of $R_1$, $R_2$, $R_3$, and $R_4$ in Formula I are unsubstituted alkyl and not all of $R_1$, $R_3$, and $R_4$ are hydrogen.

DETAILED DESCRIPTION OF THE INVENTION

Chemical Description and Terminology

Prior to setting forth the invention in detail, it may be helpful to provide definitions of certain terms to be used herein. Compounds of the present invention are generally described using standard nomenclature. Certain compounds are described herein using a general formula that includes variables. Unless otherwise specified, each variable within such a formula is defined independently of other variables.

In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms.

For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. Where a compound exists in various tautomeric forms, the invention is not limited to any one of the specific tautomers, but rather includes all tautomeric forms. In these situations, the single enantiomers, i.e., optically active forms, can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example a chiral HPLC column.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

When any variable occurs more than one time in any constituent or formula for a compound, its definition at each occurrence is independent of its definition at every other occurrence. Thus, for example, if a group is shown to be substituted with 0–2 R*, then said group may optionally be substituted with up to two R* groups and R* at each occurrence is selected independently from the definition of R*. Also, combinations of substituents and/or variables are permissible only if such combinations result in stable compounds.

The term "substituted", as used herein, means that any one or more hydrogens on the designated atom is replaced with a selection from the indicated group, provided that the designated atom's normal valence is not exceeded, and that the substitution results in a stable compound. When a substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a dihydropyridone.

As indicated above, various substituents of Formula I and Formula IA (described below) are "optionally substituted". The phrase "optionally substituted" indicates that such groups may either be unsubstituted or substituted at one or more of any of the available positions, typically 1, 2, 3, or 4 positions, by one or more suitable groups such as those disclosed herein.

When substituents such as Ar, $R_1$, $R_2$, $R_3$, and $R_4$, are further substituted, they may be so substituted at one or more available positions, typically 1 to 3 or 4 positions, by one or more suitable groups such as those disclosed herein. Suitable groups that may be present on a "substituted" Ar or other group include e.g., halogen; cyano; hydroxyl; nitro; azido; alkanoyl (such as a $C_1$–$C_6$ alkanoyl group such as acyl or the like); carboxamido; alkyl groups (including cycloalkyl groups, having 1 to about 8 carbon atoms, preferably 1, 2, 3, 4, 5, or 6 carbon atoms); alkenyl and alkynyl groups (including groups having one or more unsaturated linkages and from 2 to about 8, preferably 2, 3, 4, 5 or 6, carbon atoms); alkoxy groups having one or more oxygen linkages and from 1 to about 8, preferably 1, 2, 3, 4, 5 or 6 carbon atoms; aryloxy such as phenoxy; alkylthio groups including those having one or more thioether linkages and from 1 to about 8 carbon atoms, preferably 1, 2, 3, 4, 5 or 6 carbon atoms; alkylsulfinyl groups including those having one or more sulfinyl linkages and from 1 to about 8 carbon atoms, preferably 1, 2, 3, 4, 5, or 6 carbon atoms; alkylsulfonyl groups including those having one or more sulfonyl linkages and from 1 to about 8 carbon atoms, preferably 1, 2, 3, 4, 5, or 6 carbon atoms; aminoalkyl groups including groups having one or more N atoms and from 1 to about 8, preferably 1, 2, 3, 4, 5 or 6, carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being a preferred arylalkyl group; arylalkoxy having 1 to 3 separate or fused rings and from 6 to about 18 ring carbon atoms, with O-benzyl being a preferred arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent. For example, —$CONH_2$ is attached through the carbon atom.

As used herein, "alkyl" is intended to include both branched and straight-chain saturated aliphatic hydrocarbon groups, having the specified number of carbon atoms. Thus, the term $C_1$–$C_6$ alkyl as used herein includes alkyl groups consisting of 1 to 6 carbon atoms. When $C_0$–$C_n$alkyl is used herein in conjunction with another group, for example, aryl$C_0$–$C_4$alkyl, the indicated group, in this case aryl, is either directly bound by a single covalent bond, or attached by an alkyl chain having the specified number of carbon atoms, in this case from 1 to 4 carbon atoms. Examples of alkyl include, but are not limited to, methyl, ethyl, n-propyl, i-propyl, n-butyl, s-butyl, t-butyl, n-pentyl, and s-pentyl. Preferred alkyl groups are $C_1$–$C_8$ and $C_1$–$C_6$ alkyl groups. Especially preferred alkyl groups are methyl, ethyl, propyl, butyl, and 3-pentyl. "Carbhydryl" is intended to include both branched and straight-chain hydrocarbon groups, which are saturated or unsaturated, having the specified number of carbon atoms.

"Alkenyl" is intended to include hydrocarbon chains of either a straight or branched configuration comprising one or more unsaturated carbon-carbon bonds, which may occur in any stable point along the chain, such as ethenyl and propenyl.

"Alkynyl" is intended to include hydrocarbon chains of either a straight or branched configuration comprising one or more triple carbon-carbon bonds that may occur in any stable point along the chain, such as ethynyl and propynyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, iso-pentoxy, neopentoxy, n-hexoxy, 2-hexoxy, 3-hexoxy, and 3-methylpentoxy.

As used herein, the term "mono- or di-alkylamino" includes secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, methyl-propyl-amino.

As used herein, the term "alkylsulfinyl" includes those groups having one or more sulfoxide (SO) linkage groups and typically from 1 to about 8 carbon atoms, more typically 1 to about 6 carbon atoms.

As used herein, the term "alkylsulfonyl" includes those groups having one or more sulfonyl ($SO_2$) linkage groups and typically from 1 to about 8 carbon atoms, more typically 1 to about 6 carbon atoms.

As used herein, the term "alkylthio" includes those groups having one or more thioether linkages and preferably from 1 to about 8 carbon atoms, more typically 1 to about 6 carbon atoms.

As used herein, the term "aryl" indicates aromatic groups containing only carbon in the aromatic ring. Such aromatic groups may be further substituted with carbon or non-carbon atoms or groups. Typical aryl groups contain 1 to 3 separate, fused, or pendant rings and from 6 to about 18 ring atoms, without heteroatoms as ring members. Specifically preferred aryl groups include phenyl, naphthyl, including 1-naphthyl and 2-naphthyl, and biphenyl. The definition of the term "aryl" is not identical to that of the variable "Ar".

As used herein, "carbocyclic group" is intended to mean any stable 3- to 7-membered monocyclic group, which may be saturated, partially unsaturated, or aromatic. In addition to those exemplified elsewhere herein, examples of such carbocycles include, but are not limited to, cyclopropyl, cyclobutyl, cyclopentyl, cyclohexyl, cycloheptyl, cyclohexenyl, and phenyl.

"Cycloalkyl" is intended to include saturated hydrocarbon ring groups, having the specified number of carbon atoms, usually from 3 to about 8 ring carbon atoms. Preferred cycloalkyl groups have from 3 to 7 ring carbon atoms. Examples of cycloalkyl groups include cyclopropyl, cyclobutyl, cyclopentyl, or cyclohexyl and bridged or caged saturated ring groups such as norbornane or adamantane and the like.

In the term "(cycloalkyl)alkyl", cycloalkyl and alkyl are as defined above, and the point of attachment is on the alkyl group. This term encompasses, but is not limited to, cyclopropylmethyl, cyclohexylmethyl, and cyclohexylmethyl. Likewise, in the term "(cycloalkyl)alkoxy", cycloalkyl and alkoxy are as define above, and the point of attachment in the oxygen of the alkoxy group. The term "cycloalkyloxy" indicates a cycloalkyl group, as defined above, attached through an oxygen bridge.

"Cycloalkenyl" is intended to include hydrocarbon ring groups, having the specified number of carbon atoms, usually from 3 to about 8 ring carbon atoms, which have at least one carbon-carbon double bond. Preferred cycloalkyl groups have from 3 to 7 ring carbon atoms. Examples of cycloalkenyl groups include cyclopentenyl, and cyclohexenyl groups.

"Haloalkyl" is intended to include both branched and straight-chain saturated aliphatic hydrocarbon groups having the specified number of carbon atoms, substituted with 1 or more halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge.

"Halo" or "halogen" as used herein refers to fluoro, chloro, bromo, or iodo.

As used herein, the terms "heteroaryl" is intended to indicate a stable 5- to 7-membered monocyclic or bicyclic or 7- to 10-membered bicyclic heterocyclic ring which contains at least 1 aromatic ring that contains from 1 to 4 heteroatoms selected from N, O and S, with remaining ring atoms being carbon. When the total number of S and O atoms in the heteroaryl group exceeds 1, it is understood that these heteroatoms are not adjacent to one another. It is preferred that the total number of S and O atoms in the heterocycle is not more than 1, 2, or 3, more typically 1 or 2. It is particularly preferred that the total number of S and O atoms in the aromatic heterocycle is not more than 1. Examples of heteroaryl groups include pyridyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, and 5,6,7,8-tetrahydroisoquinoline.

The term "heterocycloalkyl" is used to indicate saturated cyclic groups containing from 1 to about 3 heteroatoms selected from N, O and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, and pyrrolidinyl groups.

As used herein, the term "heterocyclic group" is intended to include 3 to 7 membered saturated, partially unsaturated, or aromatic monocyclic groups having at least one atom selected from N, O or S. The remaining ring atoms are carbon. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen atom in the heterocycle may optionally be quaternized. It is preferred that the total number of heteroatoms in the heterocyclic groups is not more than 4 and that the total number of S and O atoms in the heterocyclic group is not more than 2, more preferably not more than 1.

Preferred heterocyclic groups include, but are not limited to, pyridinyl, pyrimidinyl, furanyl, thienyl, pyrrolyl, pyrazolyl, pyrrolidinyl, morpholinyl, piperidinyl, piperazinyl, and imidazolyl.

As used herein, "pharmaceutically acceptable salts" refer to derivatives of the disclosed compounds wherein the parent compound is modified by making non-toxic acid or base salts thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, dibesylic, sulfanilic, 2-acetoxybenzoic, fumaric, toluenesulfonic, methanesulfonic, ethane disulfonic, oxalic, isethionic, HOOC—$(CH_2)$n-COOH where n is 0–4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences,* 17th ed., Mack Publishing Company, Easton, Pa., p. 1418 (1985).

"Prodrugs" are intended to include any compounds that become compounds of Formula I when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of Formula I.

The term "therapeutically effective amount" of a compound of this invention means an amount effective, when administered to a human or non-human patient, to provide a therapeutic benefit such as an amelioration of symptoms, e.g., an amount effective to antagonize the effects of pathogenic levels of CRF or to treat the symptoms of stress disorders, affective disorder, anxiety or depression.

CRF1 Receptor Ligands

The present invention is based, in part, on the discovery that small molecules having the general Formula I, shown above (as well as pharmaceutically acceptable salts and prodrugs thereof) act as antagonists and/or inverse agonists of CRF1 receptors.

In addition to compounds and pharmaceutically acceptable salts of Formula I set forth above, the invention provides certain compounds of Formula I in which $R_1$, $R_3$, and $R_4$ carry the values set forth above for Formula I.

Ar, in this embodiment, is naphthyl, phenyl, pyridyl, pyrimidinyl, pyrazinyl, pyridizinyl, or thiophenyl, each of which is mono-, di-, or tri-substituted.

R is absent.

$R_2$ is optionally substituted alkyl, optionally substituted alkoxy, optionally substituted mono or dialkylamino, optionally substituted alkylthio, optionally substituted alkylsulfinyl, optionally substituted alkylsulfonyl, or optionally substituted mono or dialkylcarboxamide, or $R_2$ is selected from the group consisting of phenyl, naphthyl, pyridyl, pyrimidinyl, pyrazinyl, pyridizinyl, and thiophenyl, each of which is optionally mono-, di-, or tri-substituted.

The invention also provides compounds and pharmaceutically acceptable salts of Formula I in which $R_1$, $R_3$, and $R_4$ carry the values set forth above for Formula I.

Ar, in this embodiment of the invention, is phenyl or pyridyl, each of which is substituted in at least 1 position ortho to the point of attachment of Ar in Formula I, and optionally substituted with up to 4 additional substituents;

R is absent.

$R_2$ is selected from optionally substituted alkyl, optionally substituted alkoxy, and optionally substituted mono or di-alkylamino.

The invention also includes compounds and pharmaceutically acceptable salts of Formula I wherein Ar, R, $R_1$, $R_2$, $R_3$, and $R_4$ carry the following definitions.

Ar, in this embodiment, is selected from the group consisting of phenyl, naphthyl, pyridyl, pyrimidinyl, pyrazinyl, pyridizinyl, and thiophenyl, each of which is substituted with up to 5 $R_A$ groups.

R is oxygen or absent.

$R_1$, $R_3$, and $R_4$ are independently selected from hydrogen, halogen, hydroxy, amino, nitro, $C_1$–$C_6$carbhydryl$_1$, $C_1$–$C_6$carbhydryl$_1$-O—, mono- or di-$C_1$–$C_6$carbhydryl$_1$amino, $C_3$–$C_7$cycloalkyl$_2$($C_0$–$C_4$carbhydryl$_1$), $C_3$–$C_7$cycloalkenyl$_2$($C_0$–$C_4$carbhydryl$_1$), $C_3$–$C_7$cycloalkyl$_2$($C_0$–$C_4$carbhydryl$_1$)-O—, $C_3$–$C_7$cycloalkenyl$_2$($C_0$–$C_4$carbhydryl$_1$)-O—, halo$C_1$–$C_6$carbhydryl$_1$, halo$C_1$–$C_6$carbhydryl$_1$-O—, and —S(O)$_n$($C_1$–$C_6$carbhydryl$_1$), where each carbhydryl$_1$ is independently straight or branched, contains 0 or 1 or more double or triple bonds, and is unsubstituted or substituted with one or more substituents independently chosen from halogen, hydroxy, oxo, cyano, $C_1$–$C_4$alkoxy, amino, and mono- or di-($C_1$–$C_4$alkyl)amino, and where each $C_3$–$C_7$cycloalkyl$_2$ and $C_3$–$C_7$cycloalkenyl$_2$ is optionally substituted by one or more substituents independently chosen from halogen, hydroxy, oxo, cyano, $C_1$–$C_4$alkoxy, amino, and mono- or di-($C_1$–$C_4$)alkylamino.

$R_2$ is selected from the group consisting of —XR$_C$ and Y.

X is independently selected at each occurrence from the group consisting of —CH$_2$—, —CHR$_D$—, —O—, —C(=O)—, —C(=O)O—, —S(O)$_n$—, —NH—, —NR$_D$—, —C(=O)NH—, —C(=O)NR$_D$—, —S(O)$_n$NH—, —S(O)$_n$NR$_D$—, —OC(=S)S—, —NHC(=O)—, —NR$_D$C(=O)—, —NHS(O)$_n$—, and —NR$_D$S(O)$_n$—; n is 0, 1, or 2.

Y and Z are independently selected at each occurrence from: 3- to 7-membered carbocyclic or heterocyclic groups, which are saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, mono- or di-($C_1$–$C_4$alkyl)amino, and —S(O)$_n$(alkyl), wherein said 3- to 7-membered heterocyclic groups contain from 1 to 3 heteroatom(s) independently selected from N, O and S, with remaining ring members being carbon.

$R_A$ is independently selected at each occurrence from halogen, cyano, nitro, halo($C_1$–$C_6$)alkyl, halo($C_1$–$C_6$)alkoxy, hydroxy, amino, $C_1$–$C_6$alkyl substituted with 0–2 $R_B$, $C_2$–$C_6$alkenyl substituted with 0–2 $R_B$, $C_2$–$C_6$alkynyl substituted with 0–2 $R_B$, $C_3$–$C_7$cycloalkyl substituted with 0–2 $R_B$, ($C_3$–$C_7$cycloalkyl)$C_1$–$C_4$alkyl substituted with 0–2 $R_B$, $C_1$–$C_6$alkoxy substituted with 0–2 $R_B$, —NH($C_1$–$C_6$alkyl) substituted with 0–2 $R_B$, —N($C_1$–$C_6$alkyl)($C_1$–$C_6$alkyl) where each $C_1$–$C_6$alkyl is independently substituted with 0–2 $R_B$, —XR$_C$, and Y.

$R_B$ is independently selected at each occurrence from halogen, hydroxy, cyano, amino, $C_1$–$C_4$alkyl, $C_1$–$C_4$alkoxy, mono- or di-($C_1$–$C_4$alkyl)amino, —S(O)$_n$(alkyl), halo ($C_1$–$C_4$)alkyl, halo($C_1$–$C_4$)alkoxy, —CO($C_1$–$C_4$alkyl), —CONH($C_1$–$C_4$alkyl), —CON($C_1$–$C_4$alkyl)($C_1$–$C_4$alkyl), —XR$_C$, and Y.

$R_C$ and $R_D$, are the same or different, and are independently selected at each occurrence from hydrogen, and straight, branched, and cyclic alkyl groups, and (cycloalkyl) alkyl groups, having 1 to 8 carbon atoms, and containing zero or one or more double or triple bonds, each of which 1 to 8 carbon atoms may be further substituted with one or more substituent(s) independently selected from oxo, hydroxy, halogen, cyano, amino, $C_1$–$C_6$alkoxy, mono- or di-($C_1$–$C_4$alkyl)amino, —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$($C_1$–$C_6$alkyl)($C_1$–$C_6$alkyl), and Z; and n is independently selected at each occurrence from 0, 1, and 2;

Not all of $R_1$, $R_2$, $R_3$, and $R_4$ are unsubstituted alkyl and not all of $R_1$, $R_3$, and $R_4$ are hydrogen.

Such compounds will be referred to as compounds of Formula IA.

In certain embodiment the invention includes compounds and pharmaceutically acceptable salts of Formula IA in which R is absent and Ar is phenyl or pyridyl, each of which is substituted by $R_A$ in at least 1 position ortho to the point of attachment of Ar in Formula I, and optionally substituted with up to 2 additional $R_A$ groups.

Preferred compounds of this embodiment include those in which R is absent, and $R_1$, $R_3$, and $R_4$ are independently selected from the group consisting of i) hydrogen, ii) halogen, iii) $C_1$–$C_3$alkyl, iv) $C_1$–$C_3$alkoxy, v) ($C_3$–$C_7$cycloalkyl)$C_0$–$C_3$alkyl, vi) ($C_3$–$C_7$cycloalkyl)$C_0$–$C_3$alkoxy, vii) mono- or di-($C_1$–$C_3$alkyl)amino, viii)$C_1$–$C_3$haloalkyl, and ix) $C_1$–$C_3$haloalkoxy wherein each of iii, iv, v, vi, and vii is unsubstituted or substituted by 1–3 groups independently chosen from hydroxy, amino, cyano, and halogen.

The invention also includes certain compounds and pharmaceutically acceptable salts of Formula IA in which R is absent.

Ar, in this embodiment, is phenyl or pyridyl, each of which is substituted by $R_A$ in at least 1 position ortho to the point of attachment of Ar in Formula I, and optionally substituted with up to 2 additional $R_A$ groups; and $R_C$ and $R_D$, which may be the same or different, are independently selected at each occurrence from straight, branched, or cyclic alkyl groups having from 1 to 8 carbon atoms, which alkyl groups may contain one or more double or triple bonds.

Preferred compounds of this class includes those wherein $R_1$, $R_3$ and $R_4$ are independently selected from the group consisting of i) hydrogen, ii) halogen, iii) $C_1$–$C_3$alkyl, iv) $C_1$–$C_3$alkoxy, v) ($C_3$–$C_7$cycloalkyl)$C_0$–$C_3$alkyl, vi) ($C_3$–$C_7$cycloalkyl)$C_0$–$C_3$alkoxy, vii) mono- or di-($C_1$–$C_3$alkyl)amino, viii)$C_1$–$C_3$haloalkyl, and ix) $C_1$–$C_3$haloalkoxy, wherein each of iii, iv, v, vi, and vii is unsubstituted or substituted by 1–3 groups independently chosen from hydroxy, amino, cyano, and halogen.

The invention is also directed to compounds and pharmaceutically acceptable salts of Formula IA in which R is absent.

Ar, in this embodiment of the invention, is phenyl or pyridyl, each of which is substituted in at least one position ortho to the point of attachment of Ar in Formula I with a substituent selected from halogen, cyano, nitro, halo($C_1$–$C_6$) alkyl, halo($C_1$–$C_6$)alkoxy, hydroxy, amino, $C_1$–$C_6$alkyl, $C_2$–$C_6$alkenyl, $C_2$–$C_6$alkynyl, $C_3$–$C_7$cycloalkyl, ($C_3$–$C_7$cycloalkyl)$C_1$–$C_4$alkyl, $C_1$–$C_6$alkoxy, and mono- or di-($C_1$–$C_6$alkyl)amino and optionally substituted with up to 2 additional substituents independently selected from halogen, cyano, nitro, halo($C_1$–$C_6$)alkyl, halo($C_1$–$C_6$)alkoxy, hydroxy, amino, $C_1$–$C_6$alkyl, $C_2$–$C_6$alkenyl, $C_2$–$C_6$alkynyl, $C_3$–$C_7$cycloalkyl, ($C_3$–$C_7$cycloalkyl)$C_1$–$C_4$alkyl, $C_1$–$C_6$alkoxy, and mono- or di-($C_1$–$C_6$alkyl)amino.

$R_1$, $R_3$ and $R_4$ are independently selected from the group consisting of i) hydrogen, ii) halogen, iii) $C_1$–$C_3$alkyl, iv) $C_1$–$C_3$alkoxy, v) ($C_3$–$C_7$cycloalkyl)$C_0$–$C_3$alkyl, vi) ($C_3$–$C_7$cycloalkyl)$C_0$–$C_3$alkoxy, vii) mono- or di-($C_1$–$C_3$alkyl)amino, viii) $C_1$–$C_3$haloalkyl, and ix) $C_1$–$C_3$haloalkoxy, wherein each of iii, iv, v, vi, and vii is unsubstituted or substituted by 1–3 groups independently chosen from hydroxy, amino, cyano, and halogen.

Preferred compounds of this class are those wherein $R_2$ is —$XR_C$ and X is independently selected at each occurrence from the group consisting of —$CH_2$—, —$CHR_D$—, —O—, —C(=O)—, —NH—, —$NR_D$—, —C(=O)NH—, —C(=O)$NR_D$—, —NHC(=O)—, —$NR_D$C(=O)—.

It is also preferred that $R_C$ and $R_D$, are the same or different, and are independently selected at each occurrence from: hydrogen, and straight, branched, and cyclic alkyl groups, and (cycloalkyl)alkyl groups, having 1 to 8 carbon atoms, and containing zero or one or more double or triple bonds, each of which 1 to 8 carbon atoms may be further substituted with one or more substituent(s) independently selected from oxo, hydroxy, halogen, cyano, amino, $C_1$–$C_6$alkoxy, and mono- and di ($C_1$–$C_6$alkyl)amino.

More preferably, X is independently selected at each occurrence from the group consisting of —$CH_2$—, —$CHR_D$—, —O—, —NH—, —and $NR_D$—, and $R_C$ and $R_D$, are the same or different, and are independently selected at each occurrence from: hydrogen, and straight, branched, and cyclic alkyl groups, and (cycloalkyl)alkyl groups, having 1 to 8 carbon atoms, and containing zero or one or more double or triple bonds.

A particular aspect of the invention is directed to compounds of Formula II

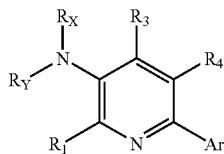

Formula II or a pharmaceutically acceptable salt thereof.

Ar, $R_1$, $R_3$, and $R_4$ carry the definitions set forth for compounds of Formula IA, above.

$R_X$ and $R_Y$ are the same or different and are independently selected from a) hydrogen, b) —(C=O)$C_1$–$C_8$alkyl; and c) straight or branched alkyl groups, cycloalkyl groups, or (cycloalkyl)alkyl groups, having 1 to 8 carbon atoms and containing zero or more double or triple bonds, each of which 1 to 8 carbon atoms may be further substituted with one or more substituent(s) independently selected from:

i) halogen, hydroxy, amino, cyano, $C_1$–$C_4$alkyl, $C_1$–$C_4$alkoxy, and mono- or di-($C_1$–$C_4$alkyl)amino, and ii) 3- to 7-membered carbocyclic or heterocyclic groups which are saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, and mono- or di-($C_1$–$C_4$alkyl)amino, wherein said 3- to 7-memberered heterocyclic groups contain from 1 to 3 heteroatom(s) independently selected from N, O, and S, with remaining ring members being carbon.

Preferred compounds of Formula II are those wherein $R_1$, $R_3$ and $R_4$ are independently selected from the group consisting of i) hydrogen, ii) halogen, iii) $C_1$–$C_4$alkyl, iv) $C_1$–$C_3$alkoxy, v) ($C_3$–$C_7$cycloalkyl)$C_0$–$C_3$alkyl, vi) ($C_3$–$C_7$cycloalkyl)$C_0$–$C_3$alkoxy, vii) mono- or di-($C_1$–$C_3$alkyl)amino, viii) $C_1$–$C_3$haloalkyl, and ix) $C_1$–$C_3$haloalkoxy, wherein each of iii, iv, v, vi, and vii is unsubstituted or substituted by 1–3 groups independently chosen from halogen, hydroxy, oxo, cyano, $C_1$–$C_4$alkoxy, amino, and mono- or di-($C_1$–$C_4$alkyl)amino.

An additional embodiment of the invention includes compounds and pharmaceutically acceptable salts of Formula II, wherein $R_1$, $R_3$, and $R_4$ carry the definitions set forth for Formula IA.

$R_X$ and $R_Y$, in this embodiment of the invention, are the same or different and are independently selected from: a) hydrogen, b) —(C=O)$C_1$–$C_8$alkyl, and c) straight or branched alkyl groups, cycloalkyl groups, or (cycloalkyl)alkyl groups, having 1 to 8 carbon atoms and containing zero or more double or triple bonds, each of which 1 to 8 carbon atoms may be further substituted with one or more substituent(s) independently selected from: halogen, hydroxy, amino, cyano, $C_1$–$C_4$alkyl, $C_1$–$C_4$alkoxy, and mono- or di-($C_1$–$C_4$alkyl)amino.

Ar is phenyl or pyridyl, each of which is mono-, di-, or tri-substituted with $R_4$, (which carries the definition set forth for compounds of Formula IA) with the proviso that at least one of the positions ortho to the point of attachment of Ar shown in Formula II is substituted.

X is independently selected at each occurrence from the group consisting of —$CH_2$—, —$CHR_D$—, —O—, —C(=O)—, —C(=O)O—, —NH—, —$NR_D$—, —C(=O)NH—, —C(=O)$NR_D$—, —NHC(=O)—, and —$NR_D$C(=O)—.

Y and Z are independently selected at each occurrence from: 3- to 7-membered carbocyclic or heterocyclic groups which are saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, mono- or di-($C_1$–$C_4$alkyl)amino, wherein said 3- to 7-memberered heterocyclic groups contain from 1 to 3 heteroatom(s) independently selected from N, O and S, with remaining ring members being carbon; and $R_C$ and $R_D$, are the same or different, and are independently selected at each occurrence from: hydrogen, and straight, branched, and cyclic alkyl groups, and (cycloalkyl)alkyl groups, having 1 to 8 carbon atoms, and containing zero or one or more double or triple bonds, each of which 1 to 8 carbon atoms may be further substituted with one or more substituent(s) independently selected from oxo, hydroxy, halogen, cyano, amino, $C_1$–$C_6$alkoxy, mono- or di-($C_1$–$C_4$alkyl)amino, —NHC(=O)($C_1$–$C_6$alkyl), —N($C_1$–$C_6$alkyl)C(=O)($C_1$–$C_6$alkyl), and Z.

Preferred compounds of this class are those wherein $R_X$ is a) hydrogen or b) a straight or branched alkyl group, a cycloalkyl groups, or (cycloalkyl)alkyl group, each of which groups having 1 to 8 carbon atoms and containing zero or more double or triple bonds, each of which 1 to 8 carbon atoms may be further substituted with one or more substituent(s) independently selected from halogen, hydroxy, amino, cyano, $C_1$–$C_4$alkyl, $C_1$–$C_4$alkoxy, and mono- or di-($C_1$–$C_4$)alkylamino.

$R_Y$, is preferably, a straight or branched alkyl group, a cycloalkyl groups, or (cycloalkyl)alkyl group, each of which groups having 1 to 8 carbon atoms and containing zero or more double or triple bonds, each of which 1 to 8 carbon atoms may be further substituted with one or more substituent(s) independently selected from halogen, hydroxy, amino, cyano, $C_1$–$C_4$alkyl, $C_1$–$C_4$alkoxy, and mono- or di-($C_1$–$C_4$)alkylamino.

Ar is phenyl or pyridyl, mono-, di-, or tri-substituted with substituents independently selected at each occurrence from halogen, cyano, nitro, halo($C_1$–$C_6$)alkyl, halo($C_1$–$C_6$)alkoxy, hydroxy, amino, $C_1$–$C_6$alkyl, $C_2$–$C_6$alkenyl, $C_2$–$C_6$alkynyl, $C_3$–$C_7$cycloalkyl, ($C_3$–$C_7$cycloalkyl)$C_1$–$C_4$alkyl, $C_1$–$C_6$alkoxy, and mono- or di-($C_1$–$C_6$alkyl)amino.

$R_1$, $R_3$ and $R_4$ are independently selected from the group consisting of hydrogen, halogen, $C_1$–$C_4$alkyl, $C_1$–$C_3$alkoxy, ($C_3$–$C_7$cycloalkyl)$C_0$–$C_3$alkyl, ($C_3$–$C_7$cycloalkyl)$C_0$–$C_3$alkoxy, mono- or di-($C_1$–$C_3$alkyl)amino, $C_1$–$C_3$haloalkyl, and $C_1$–$C_3$haloalkoxy.

Particularly preferred compounds of this class are those wherein $R_X$ is hydrogen, $C_1$–$C_6$alkyl, a $C_3$–$C_7$cycloalkyl, or ($C_3$–$C_7$cycloalkyl) $C_1$–$C_4$alkyl; $R_Y$ a $C_1$–$C_6$alkyl, a $C_3$–$C_7$cycloalkyl, or ($C_3$–$C_7$cycloalkyl) $C_1$–$C_4$alkyl.

Ar is phenyl or pyridyl, mono-, di-, or tri-substituted with substituents independently selected at each occurrence from halogen, halo($C_1$–$C_2$)alkyl, halo($C_1$–$C_2$)alkoxy, hydroxy, amino, $C_1$–$C_3$alkyl, $C_1$–$C_2$alkoxy, and mono- or di-($C_1$–$C_2$alkyl)amino.

$R_1$ and $R_4$ are independently selected from the group consisting of hydrogen, halogen, $C_1$–$C_3$alkyl, $C_1$–$C_3$alkoxy, mono- or di-($C_1$–$C_3$alkyl)amino, $C_1$–$C_3$haloalkyl, and $C_1$–$C_3$haloalkoxy; and $R_3$ is hydrogen, halogen, or methyl.

Other preferred values of $R_1$ for compounds and salts Formula II include methyl, methoxy, ethyl and ethoxy.

Preferred $R_X R_Y N$— combinations for compounds of Formula II include propyl-amino, dipropyl-amino, propyl-cyclopropylmethyl-amino, propyl-isopropyl-amino, propyl-(3-methylbutyl)-amino, propyl-benzyl-amino, propyl-(3-pyridylmethyl)-amino, propyl-ethyl-amino, and propyl-butyl-amino groups. $R_X R_Y N$— combinations in which $R_X$ is hydrogen and $R_Y$ is cyclopropylmethyl or a branched alkyl group having 3 to 6 carbon atoms are particularly preferred.

For compounds of Formula II it is also preferred that $R_3$ is hydrogen or chloro.

Preferred values of $R_4$ include methyl, ethyl, methoxy, ethoxy, and halogen. Methyl, ethyl and bromo are particularly preferred.

A further embodiment of the invention includes compounds of Formula III

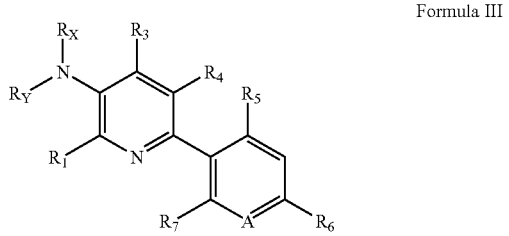

Formula III and the pharmaceutically acceptable salts thereof.

$R_X$, $R_Y$, $R_1$, $R_3$, and $R_4$ carry the definitions set forth for compounds of Formula II, above.

A is CH or N.

$R_5$, $R_6$, and $R_7$ are independently i) hydrogen, halogen, cyano, halo($C_1$–$C_4$)alkyl, halo($C_1$–$C_4$)alkoxy, hydroxy, amino, $C_1$–$C_6$alkyl, $C_1$–$C_6$alkoxy, ($C_1$–$C_4$alkoxy) $C_1$–$C_4$alkoxy, or mono- or di($C_1$–$C_4$alkyl)amino, or ii) $C_1$–$C_6$alkyl or $C_1$–$C_6$alkoxy, each of which is further substituted with a 3- to 7-membered carbocyclic or heterocyclic groups which is saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, and mono- or di-($C_1$–$C_4$alkyl)amino.

At least one of $R_5$ and $R_7$ is not hydrogen.

An embodiment of the invention is directed to compounds of Formula III wherein $R_X$ is a) hydrogen or b) a straight or branched alkyl group, a cycloalkyl group, or (cycloalkyl)alkyl group, having 1 to 8 carbon atoms and containing zero or more double or triple bonds, each of which 1 to 8 carbon atoms may be further substituted with one or more substituent(s) independently selected from halogen, hydroxy, amino, cyano, $C_1$–$C_4$alkyl, $C_1$–$C_4$alkoxy, and mono- or di-($C_1$–$C_4$)alkylamino.

$R_Y$ is a straight or branched alkyl group, a cycloalkyl group, or (cycloalkyl)alkyl group, each having 1 to 8 carbon atoms and containing zero or more double or triple bonds, each of which 1 to 8 carbon atoms may be further substituted with one or more substituent(s) independently selected from halogen, hydroxy, amino, cyano, $C_1$–$C_4$alkyl, $C_1$–$C_4$alkoxy, and mono- or di-($C_1$–$C_4$)alkylamino.

$R_1$ and $R_4$, in this embodiment of the invention, are independently selected from the group consisting of hydrogen, halogen, $C_1$–$C_4$alkoxy, halo($C_1$–$C_4$)alkyl, halo($C_1$–$C_4$)alkoxy, and $C_1$–$C_6$alkyl, which $C_1$–$C_6$alkyl is unsubstituted or substituted by one to three substituents independently selected from hydroxy, oxo, cyano, $C_1$–$C_4$alkoxy, amino, and mono- or di($C_1$–$C_4$)alkylamino.

$R_3$ is hydrogen, halogen, methyl, or methoxy.

$R_5$, $R_6$, and $R_7$ are independently selected from hydrogen, halogen, cyano, halo($C_1$–$C_4$)alkyl, halo($C_1$–$C_4$)alkoxy, hydroxy, amino, $C_1$–$C_6$alkyl, $C_1$–$C_6$alkoxy, ($C_1$–$C_4$alkoxy) $C_1$–$C_4$alkoxy, and mono- or di($C_1$–$C_4$alkyl)amino.

Additionally the invention includes compounds and pharmaceutically acceptable salts of Formula IV

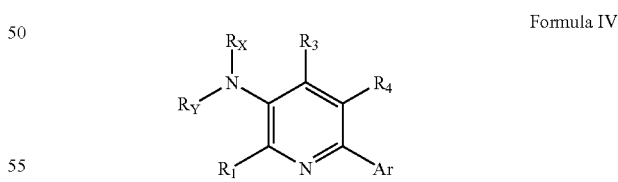

Formula IV

Ar, $R_1$, $R_3$, and $R_4$ carry the definitions set forth for Formula IA. $R_X$ and $R_Y$ are joined to form a saturated 5 to 7 membered heterocycloalkyl ring containing 0 or 1 additional heteroatom selected from N, O and S, wherein said saturated 5 to 7 membered heterocycloalkyl ring is optionally substituted with from 1 to 4 groups independently chosen from halogen, hydroxy, methyl and methoxy.

A further embodiment of the invention includes compounds and pharmaceutically acceptable salts of Formula V

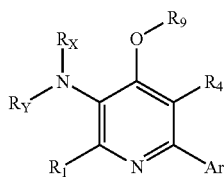

Formula V $R_X$ and $R_Y$ carry the definitions set forth for Formula II.

Ar, for compounds of Formula V, is phenyl or pyridyl, each of which is mono-, di-, or tri-substituted with $R_A$ (which carries the definition set forth for Formula IA), with the proviso that at least one of the positions ortho to the point of attachment of Ar shown in Formula V is substituted.

$R_1$ and $R_4$ are independently selected from the group consisting of hydrogen, halogen, $C_1$–$C_4$alkoxy, halo($C_1$–$C_4$) alkyl, halo($C_1$–$C_4$)alkoxy, $C_1$–$C_6$alkyl, and mono- and di-($C_1$–$C_4$alkyl)amino.

$R_9$ is selected from straight or branched alkyl groups, cycloalkyl groups, and (cycloalkyl)alkyl groups, having 1 to 8 carbon atoms and containing zero or more double or triple bonds, each of which 1 to 8 carbon atoms may be further substituted with one or more substituent(s) independently selected from oxo, hydroxy, halogen, cyano, $C_1$–$C_4$alkoxy, amino, and mono- or di-($C_1$–$C_4$)alkylamino.

A particular subset of compounds of Formula V which are included in the invention, is described by Formula VI:

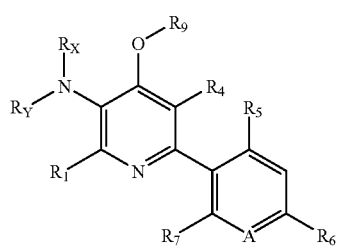

Formula VI

In the embodiment of the invention described by Formula VI, the variables $R_X$ and $R_Y$ carry the definitions set forth for Formula II, and $R_1$, $R_4$, and $R_9$ carry the definitions set forth for Formula V.

A is CH or N.

$R_5$, $R_6$, and $R_7$, in this embodiment of the invention, are independently i) hydrogen, halogen, cyano, halo($C_1$–$C_4$) alkyl, halo($C_1$–$C_4$)alkoxy, hydroxy, amino, $C_1$–$C_6$alkyl, $C_1$–$C_6$alkoxy, ($C_1$–$C_4$alkoxy)$C_1$–$C_4$alkoxy, or mono- or di($C_1$–$C_4$alkyl)amino, or ii) $C_1$–$C_6$alkyl or $C_1$–$C_6$alkoxy, each of which is further substituted with a 3- to 7-membered carbocyclic or heterocyclic groups which is saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, and mono- or di-($C_1$–$C_4$alkyl) amino.

In this embodiment at least one of $R_5$ and $R_7$ is not hydrogen.

Another subset of compounds of Formula V which are included in the invention, is described by Formula VII:

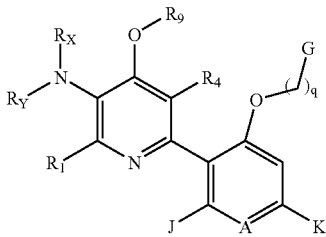

Formula VII

In this embodiment of the invention $R_X$ and $R_Y$ carry the definitions set forth for Formula II and $R_1$, $R_3$, and $R_4$ carry the definitions set forth for compounds of Formula V.

A is CH or N and q is an integer from 1 to 4.

G is hydrogen, hydroxy, $C_1$–$C_4$alkoxy, mono- or di($C_1$–$C_4$alkyl)amino, or a 3- to 7-membered carbocyclic or heterocyclic group which is saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, mono- or di-($C_1$–$C_4$alkyl)amino and —S(O)$_n$(alkyl), wherein said 3- to 7-memberered heterocyclic group contains from 1 to 3 heteroatom(s) independently selected from N, O and S, with remaining ring members being carbon, and n is 0, 1, or 2.

J and K are independently selected from hydrogen, halogen, cyano, halo($C_1$–$C_4$)alkyl, halo($C_1$–$C_4$)alkoxy, hydroxy, amino, $C_1$–$C_6$alkyl, $C_1$–$C_6$alkoxy, ($C_1$–$C_4$alkoxy) $C_1$–$C_4$alkoxy, and mono- or di($C_1$–$C_4$alkyl)amino.

The invention further includes compounds of Formula VIII

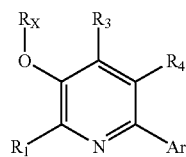

Formula VIII and the pharmaceutically acceptable salt thereof. In this embodiment of the invention, the variables Ar, $R_1$, $R_3$, and $R_4$ carry the definitions set forth for Formula IA.

$R_X$ is a straight or branched alkyl group, cycloalkyl group, or (cycloalkyl)alkyl group, having 1 to 8 carbon atoms and containing zero or more double or triple bonds, each of which 1 to 8 carbon atoms may be further substituted with one or more substituent(s) independently selected from: i) halogen, hydroxy, amino, cyano, $C_1$–$C_4$alkyl, $C_1$–$C_4$alkoxy, and mono- or di-($C_1$–$C_4$alkyl)amino, ii) 3- to 7-membered carbocyclic or heterocyclic groups which are saturated, partially unsaturated, or aromatic, which may be further substituted with one or more substituents independently selected from halogen, hydroxy, amino, cyano, $C_1$–$C_4$alkyl, $C_1$–$C_4$alkoxy, and mono- or di-($C_1$–$C_4$alkyl)amino, wherein said 3- to 7-memberered heterocyclic groups contain from 1 to 3 heteroatom(s) independently selected from N, O, and S, with remaining ring members being carbon.

Preferred compounds and salts of Formula VIII in those wherein:

Ar is phenyl or pyridyl, each of which is mono-, di-, or tri-substituted with $R_A$ (which carries the definitions set forth for Formula IA), with the proviso that at least one of the positions ortho to the point of attachment of Ar shown in Formula VIII is substituted.

X is independently selected at each occurrence from the group consisting of —CH$_2$—, —CHR$_D$—, —O—, —C(=O)—, —C(=O)O—, —NH—, —NR$_D$—, —C(=O)NH—, —C(=O)NR$_D$—, —NHC(=O)—, and —NR$_D$C(=O)—.

Y and Z are independently selected at each occurrence from: 3- to 7-membered carbocyclic or heterocyclic groups which are saturated, partially unsaturated, or aromatic, which may be further substituted with one or more substituents independently selected from halogen, oxo, hydroxy, amino, cyano, C$_1$–C$_4$alkyl, —O(C$_1$–C$_4$alkyl), and —NH(C$_1$–C$_4$alkyl), —N(C$_1$–C$_4$alkyl)(C$_1$–C$_4$alkyl), wherein said 3- to 7-memberered heterocyclic groups contain from 1 to 3 heteroatom(s) independently selected from N, O and S, with remaining ring members being carbon; and R$_C$ and R$_D$, are the same or different, and are independently selected at each occurrence from: hydrogen, and straight, branched, and cyclic alkyl groups, and (cycloalkyl)alkyl groups, having 1 to 8 carbon atoms, and containing zero or one or more double or triple bonds, each of which 1 to 8 carbon atoms may be further substituted with one or more substituent(s) independently selected from oxo, hydroxy, halogen, cyano, amino, C$_1$–C$_6$alkoxy, mono- or di-(C$_1$–C$_4$alkyl)amino, —NHC(=O)(C$_1$–C$_6$alkyl), —N(C$_1$–C$_6$alkyl)C(=O)(C$_1$–C$_6$alkyl), and Z.

Preferred values of R$_1$, R$_3$ and R$_4$ for compounds and salts of Formula IA include i) hydrogen, ii)halogen, iii) C$_1$–C$_4$alkyl, iv) C$_1$–C$_3$alkoxy, v) (C$_3$–C$_7$cycloalkyl)C$_0$–C$_3$alkyl, vi) (C$_3$–C$_7$cycloalkyl)C$_0$–C$_3$alkoxy, vii) mono- or di-(C$_1$–C$_3$alkyl)amino, viii)C$_1$–C$_3$haloalkyl, and ix) C$_1$–C$_3$haloalkoxy, wherein each of iii, iv, v, vi, and vii is unsubstituted or substituted by 1–3 groups independently chosen from halogen, hydroxy, oxo, cyano, C$_1$–C$_4$alkoxy, amino, and mono- or di-(C$_1$–C$_4$alkyl)amino.

The invention also includes preferred compounds and salts of Formula VIII in which:

R$_X$ is a straight or branched alkyl group, a cycloalkyl groups, or (cycloalkyl)alkyl group, having 1 to 8 carbon atoms and containing zero or more double or triple bonds, each of which 1 to 8 carbon atoms may be further substituted with one or more substituent(s) independently selected from halogen, hydroxy, amino, cyano, C$_1$–C$_4$alkyl, C$_1$–C$_4$alkoxy, and mono- or di-(C$_1$–C$_4$)alkylamino.

Ar is phenyl or pyridyl, mono-, di-, or tri-substituted with substituents independently selected at each occurrence from halogen, cyano, nitro, halo(C$_1$–C$_6$)alkyl, halo(C$_1$–C$_6$)alkoxy, hydroxy, amino, C$_1$–C$_6$alkyl, C$_2$–C$_6$alkenyl, C$_2$–C$_6$alkynyl, C$_3$–C$_7$cycloalkyl, (C$_3$–C$_7$cycloalkyl)C$_1$–C$_4$alkyl, C$_1$–C$_6$alkoxy, and mono- or di-(C$_1$–C$_6$alkyl)amino.

R$_1$, R$_3$ and R$_4$ are independently selected from the group consisting of hydrogen, halogen, C$_1$–C$_4$alkyl, C$_1$–C$_3$alkoxy, (C$_3$–C$_7$cycloalkyl)C$_0$–C$_3$alkyl, (C$_3$–C$_7$cycloalkyl)C$_0$–C$_3$alkoxy, mono- or di-(C$_1$–C$_3$alkyl)amino, C$_1$–C$_3$haloalkyl, and C$_1$–C$_3$haloalkoxy.

Particularly preferred compounds of this class include those wherein:

R$_X$ is a C$_1$–C$_6$alkyl, C$_3$–C$_7$cycloalkyl, or (C$_3$–C$_7$cycloalkyl) C$_1$–C$_4$alkyl group.

Ar is phenyl or pyridyl, mono-, di-, or tri-substituted with substituents independently selected at each occurrence from halogen, halo(C$_1$–C$_2$)alkyl, halo(C$_1$–C$_2$)alkoxy, hydroxy, amino, C$_1$–C$_3$alkyl, C$_1$–C$_2$alkoxy, and mono- or di-(C$_1$–C$_2$alkyl)amino.

R$_1$ and R$_4$ are independently selected from the group consisting of hydrogen, halogen, C$_1$–C$_3$alkyl, C$_1$–C$_3$alkoxy, mono- or di-(C$_1$–C$_3$alkyl)amino, C$_1$–C$_3$haloalkyl, and C$_1$–C$_3$haloalkoxy; and R$_3$ is hydrogen, halogen, or methyl.

In yet another embodiment, the invention includes a subset of compounds of Formula VIII, which are described by Formula IX:

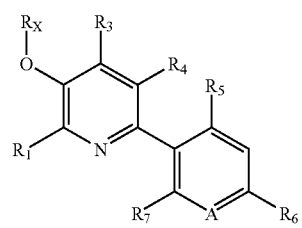

Formula IX

In this embodiment, R$_X$ carries the definition set forth for Formula VIII, and R$_1$, R$_3$, and R$_4$ carry the definitions set forth for Formula IA.

A is CH or N.

R$_5$, R$_6$, and R$_7$ are independently i) hydrogen, halogen, cyano, halo(C$_1$–C$_4$)alkyl, halo(C$_1$–C$_4$)alkoxy, hydroxy, amino, C$_1$–C$_6$alkyl, C$_1$–C$_6$alkoxy, (C$_1$–C$_4$alkoxy) C$_1$–C$_4$alkoxy, or mono- or di-(C$_1$–C$_4$alkyl)amino, or ii) C$_1$–C$_6$alkyl or C$_1$–C$_6$alkoxy, each of which is further substituted with a 3- to 7-membered carbocyclic or heterocyclic groups which is saturated, partially unsaturated, or aromatic, which may be further substituted with one or more substituents independently selected from halogen, oxo, hydroxy, amino, cyano, C$_1$–C$_4$alkyl, C$_1$–C$_4$alkoxy, and mono- or di-(C$_1$–C$_4$alkyl)amino, wherein said 3- to 7-memberered heterocyclic group contains from 1 to 3 heteroatom(s) independently selected from N, O and S, with remaining ring members being carbon. At least one of R$_5$ and R$_7$ is not hydrogen.

Preferred compounds and salts of Formula IX include those wherein:

R$_X$ is a straight or branched alkyl group, a cycloalkyl group, or (cycloalkyl)alkyl group, having 1 to 8 carbon atoms and containing zero or more double or triple bonds, each of which 1 to 8 carbon atoms may be further substituted with one or more substituent(s) independently selected from halogen, hydroxy, amino, cyano, C$_1$–C$_4$alkyl, C$_1$–C$_4$alkoxy, and mono- or di-(C$_1$–C$_4$)alkylamino.

R$_1$ and R$_4$ are independently selected from the group consisting of hydrogen, halogen, C$_1$–C$_4$alkoxy, halo(C$_1$–C$_4$) alkyl, halo(C$_1$–C$_4$)alkoxy, and C$_1$–C$_6$alkyl, which C$_1$–C$_6$alkyl is unsubstituted or substituted by one to three substituents independently selected from hydroxy, oxo, cyano, C$_1$–C$_4$alkoxy, amino, and mono- or di(C$_1$–C$_4$)alkylamino.

R$_3$ is hydrogen, halogen, methyl, or methoxy.

R$_5$, R$_6$, and R$_7$ are independently selected from hydrogen, halogen, cyano, halo(C$_1$–C$_4$)alkyl, halo(C$_1$–C$_4$)alkoxy, hydroxy, amino, C$_1$–C$_6$alkyl, C$_1$–C$_6$alkoxy, (C$_1$–C$_4$alkoxy) C$_1$–C$_4$alkoxy, and mono- or di(C$_1$–C$_4$alkyl)amino.

Other preferred values of R$_1$ for compounds and salts Formula IX, include hydrogen, halogen, methyl, ethyl, methoxy, ethoxy, and mono-and di-(C$_1$–C$_2$alkyl)amino. Particularly preferred values of R$_1$ for compounds and salts of Formula IX are methyl, ethyl, methylamino, methyl-ethyl-amino, methoxy and chloro.

Preferred $R_X$ groups for Formula IX include straight or branched chain alkyl groups having 3 to 6 carbon atoms, particularly 1-ethyl-propyl.

For compounds of Formula IX it is also preferred that $R_3$ is hydrogen or chloro.

Preferred values of $R_4$ include methyl, ethyl, methoxy, ethoxy, and halogen. Methyl, ethyl and bromo are particularly preferred.

In another preferred embodiment the invention includes compounds of Formula IX in which $R_1$ is methylamino, $R_X$ is -ethyl-propyl, $R_3$ is hydrogen or methyl, $R_4$ is methyl, ethyl or bromo, A is CH, $R_5$ and $R_6$ are selected from halogen, methoxy, ethoxy, methyl, ethyl, and trifluoromethoxy, and $R_7$ is hydrogen or methyl.

In addition to compounds and salts of Formulae I–IX, above, the invention provides compounds and pharmaceutically acceptable salts of Formula X

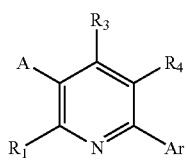

Formula X

A is a tetrahydropyridyl group or a piperidinyl group of Formula X-a, Formula X-b, or Formula X-c:

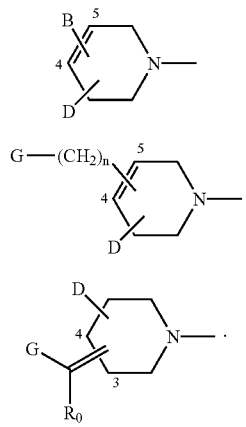

Formula X-a

Formula X-b

Formula X-c

The position of substitution by the B group in the group represented by Formula X-a is the 4-position or 5-position, the position of substitution by the G-(CH$_2$)$_n$— group in the group represented by Formula X-b is the 4-position or 5-position, and the position of substitution the G-C(R$_0$)= group in the group represented by Formula X-c is the 3-position or 4-position.

In Formula X-a, B represents phenyl, pyridyl, pyrimidinyl, furanyl, or thiophenyl, each of which is unsubstituted or substituted by up to 3 substituents independently selected from halogen, hydroxy, amino, cyano, alkyl, alkoxy, haloalkyl, and haloalkoxy.

D represents from 0 to 3 groups independently chosen from halogen, methyl, ethyl, methoxy, and ethoxy.

In Formula X-b, n is an integer of 0 to 5.

$R_0$, in Formula X-c, represents hydrogen, alkyl, cycloalkyl, or (cycloalkyl)alkyl.

G represents i) cyano, ii) a group of the formula —CONR$_{11}$R$_{12}$ wherein R$_{11}$ and R$_{12}$ are independently selected from hydrogen, alkyl, cycloalkyl, (cycloalkyl)alkyl, alkoxyalkyl, cycloalkyloxyalkyl, and phenyl, or R$_{11}$ and R$_{12}$ are taken together with the nitrogen atom to which they are attached to form a 5- to 8-membered saturated heterocyclic group of the formula:

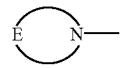

wherein E is CH$_2$, NH, N-alkyl, N-cycloalkyl, N-alkyl (cycloalkyl), O, or S, or iii) a group of the formula —CO$_2$R$_{13}$, wherein R$_{13}$ represents hydrogen, alkyl, cycloalkyl, (cycloalkyl)alkyl, alkoxyalkyl(cycloalkyloxy) alkyl, or phenyl.

The variables Ar, $R_1$, $R_3$, and $R_4$ in Formula X carry the definitions set forth for Formula IA.

Preferred substituents of the Ar group, for compounds of Formula I, Formula IA and the subformulae thereof, including, for example, compounds of Formula II, Formula III, Formula VIII and Formula IX are chloro, methyl, methoxy, ethyl, ethoxy, trifluoromethoxy, difluoromethoxy, trifluoromethyl, difluoromethyl, 1-ethyl-propoxy, isopropoxy, isopropyl, and isopropyl amino. Particularly preferred Ar groups, include, but are not limited to, 2,4-dimethoxyphenyl, 2-methoxy-4-ethylphenyl, 2-methyl-4-methoxyphenyl, 2-methoxy-4-trifluoromethoxyphenyl, 2,4-dichlorophenyl, 2-chloro-4-methoxyphenyl, 2-methoxy-4-isopropoxyphenyl, 2-chloro-4-isopropoxyphenyl, 2-methoxy-4-difluoromethoxyphenyl, 2-methoxy-4-isopropylphenyl, 2-difluoromethoxy-4-methoxyphenyl, 2-methoxy-4-trifluoromethoxyphenyl, 2-methoxy-4-ethoxyphenyl, 2-methoxy-4-trifluoromethylphenyl, 2-trifluoromethoxy-4-methoxyphenyl, 2-methyl-4-isopropyl-3-pyridyl, 2-methoxy-4-isopropyl-3-pyridyl, 2-methoxy-4-isopropoxy-3-pyridyl, 2-methoxy-4-dimethylamino-3-pyridyl, 4-isopropyl-6-methoxy-3-pyridyl, 4-isopropoxy-6-methoxy-3-pyridyl, 4-isopropyl-6-methoxy-2-pyridyl, 2-ethyl-4-isopropylmethoxy-3-pyridyl, 2-methyl-4-isopropylamino-5-methoxy-3-pyridyl, 2-hydroxymethyl-4-isopropyl-3-pyridyl, 2-ethoxy-4-isopropyl-3-pyridyl, 2,4,6-trimethyl-5-(4-methyl-oxazol-2-yl)-3-pyridyl, 2-ethyl-4-isopropyl-3-pyridyl, and 2-ethyl-4-isopropylaminophenyl.

Additional preferred Ar groups are given in the table entitled "Ar Matrix" provided herein.

Preferred compounds of Formula I exhibit an IC$_{50}$ value of 1 micromolar or less in a standard in vitro CRF receptor binding assay. More preferred compounds exhibit an IC$_{50}$ value of 100 nanomolar or less in a standard in vitro CRF receptor binding assay. Particularly preferred compounds of Formula I exhibit an IC$_{50}$ value of 10 nanomolar or less in a standard in vitro CRF receptor binding assay. A standard in vitro CRF1 receptor binding assay is disclosed in Example 11, below.

The invention further provides intermediates useful in the preparation of compounds of Formula I, Formula IA, any the particular embodiments thereof (e.g., Formula II–Formula X), or any of the compounds of Formula I specifically disclosed herein. Intermediates useful in the synthesis of compounds in the invention are described in Schemes 1–3 below, and further illustrated in Examples 1–7. For example, useful intermediates provided by the invention include aryl metallo compounds and aryl boronic acids useful for coupling to the pyridine core of Formula I. Particular examples of such intermediates include, for example 4-methoxy-2-methylbenzeneboronic acid, 2-Methoxy-6-isopropyl-3-pyridylboronic acid (step 3, example 4), and 4-Trifluoromethoxy-2-methoxy-phenylboronic acid (see step 6, example 5).

The invention also provides pharmaceutical compositions comprising a compound, pharmaceutically acceptable salt, or prodrug of Formula I, Formula IA, any the particular embodiments thereof (e.g., Formula II–Formula X), or any of the compounds of Formula I specifically disclosed herein, together with a pharmaceutically acceptable carrier or excipient. Pharmaceutically acceptable carriers suitable for use in a composition provided by the invention may be inert, or may modulate the bioavailability or stability of the active compound. Representative carriers include, for example, molecules such as albumin, polylysine, polyamidoamines, peptides, proteins, polystyrene, polyacrylamide, lipids, ceramide and biotin, solid support materials such as beads and microparticles comprising, for example, polyacetate, polyglycolate, poly(lactide-co-glycolide), polyacrylate, starch, cellulose or dextran. The pharmaceutical composition, may be prepared in a variety of forms, for example, as an injectable fluid, an aerosol, a cream, a gel, a pill, a capsule, a syrup, or a transdermal patch.

The invention also provides packages comprising a pharmaceutical composition as described immediately above in a container and instructions for using the composition to treat a patient suffering from anxiety, or instructions for using the composition to treat a patient suffering from stress, or instructions for using the composition to treat a patient suffering from depression, or instructions for using the composition to treat a patient suffering from irritable bowel syndrome or instructions for using the composition to treat a patient suffering from Crohn's disease.

The CRF binding compounds provided by this invention and labeled derivatives thereof are also useful as standards and reagents in determining the ability of other compounds (e.g., a potential pharmaceutical agent) to bind to the CRF receptor.

The invention provides a method for demonstrating the presence of CRF receptors (preferably CRF1 receptors) in a biological sample (e.g., a tissue section or homogenate), said method comprising contacting the biological sample with a labeled compound of Formula I under conditions that permit binding of the labeled compound to a CRF receptor and detecting the labeled compound in the biological sample. Unbound labeled compound is preferably at least partially removed from the biological sample prior to detecting the bound labeled compound in the sample.

For detection purposes the compound may be labeled, for example, with a fluorescent, isotopic, or radiolabel. Radiolabeled and isotopically labeled compounds of Formula I–X, which are also included in the invention, are identical to the compounds recited in Formulae I–X, with one or more atoms replaced by an atom having an atomic mass or mass number different from the most highly abundant isotope of that atom. Examples of isotopes that can be incorporated into compounds of Formula I in accordance with this aspect of the invention includes isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$. Preparation of such radiolabeled compounds of Formula I is described below in Example 12. The labeled compound may be detected if radiolabeled, e.g., autoradiographically, and if otherwise isotopically labeled, e.g., by NMR. Labeled derivatives of the CRF antagonist compounds of Formula I are also useful as radiotracers for positron emission tomography (PET) imaging or for single photon emission computerized tomography (SPECT).

The present invention also pertains to methods of inhibiting the binding of CRF to CRF receptors which methods involve contacting a solution containing a compound of Formula I with at least one cell (e.g., a neuronal cell) expressing CRF receptors (e.g., preferably CRF1 receptors), wherein the compound is present in the solution at a concentration sufficient to inhibit CRF binding to CRF receptors in vitro. This method includes inhibiting the binding of CRF to CRF receptors in vivo in an animal (e.g., preferably a human patient). The animal is given an amount of a compound of Formula I that results in a concentration in a relevant body fluid (e.g., blood, plasma, serum, CSF, interstitial fluid) of the animal, which concentration is at least sufficient to inhibit the binding of CRF to CRF receptors in vitro.

The present invention also pertains to methods of altering (i.e. increasing or decreasing) the CRF-stimulated activity of CRF receptors, which methods involve contacting a solution containing a compound Formula I with at least one cell (e.g., a neuronal cell) expressing CRF receptors (e.g., preferably CRF1 receptors), wherein the compound is present in the solution at a concentration sufficient to alter the CRF-stimulated signal transduction activity of CRF receptors in cells expressing CRF receptors (preferably cells expressing such receptors at levels above those found in naturally occurring CRF receptor-expressing cells) in vitro. This method includes altering the CRF-stimulated activity of CRF receptors in vivo in an animal (e.g., preferably a human patient). The animal is given an amount of a compound of Formula I that results in compound a concentration in a relevant body fluid (e.g., blood, plasma, serum, CSF, interstitial fluid) of the animal, which concentration is at least sufficient to alter the CRF-stimulated activity of CRF receptors in vitro.

In one embodiment, such methods are useful in treating physiological disorders associated with excess concentrations of CRF in a patient (e.g., in a body fluid of the patient). The amount of a compound that would be sufficient to inhibit the binding of a CRF to a CRF receptor or to alter the CRF-stimulated activity of CRF receptors may be readily determined via a CRF receptor binding assay (see Example 11), or from the $EC_{50}$ of a CRF receptor functional assay. CRF receptors that may be used to determine in vitro binding are found in a variety of sources, for example in cells that autologously express CRF receptors, e.g. IMR32 cells, or in a cell expressing a CRF receptor as a result of the expression of an exogenous CRF receptor-encoding polynucleotide comprised by the cell.

Methods of Treatment

Compounds of Formula I are useful in treating a variety of conditions including affective disorders, anxiety disorders, stress disorders, eating disorders, digestive disorders, and drug addiction.

Affective disorders include all types of depression, bipolar disorder, cyclothymia, and dysthymia.

Anxiety disorders include generalized anxiety disorder, panic, phobias and obsessive-compulsive disorder.

Stress, includes, for example, post-traumatic stress disorder, hemorrhagic stress, stress-induced psychotic episodes, psychosocial dwarfism, stress headaches, stress-induced immune systems disorders such as stress-induced fever, and stress-related sleep disorders.

Eating disorders include anorexia nervosa, bulimia nervosa, and obesity.

Digestive disorders include, but are not limited to, irritable bowel syndrome and Crohn's disease.

Modulators of the CRF receptors may also be useful in the treatment of a variety of neurological disorders including supranuclear palsy, AIDS related dementias, multiinfarct dementia, neurodegenerative disorders such as Alzheimer's disease, Parkinson's disease, and Huntington's disease, head trauma, spinal cord trauma, ischemic neuronal damage, amyotrophic lateral sclerosis, disorders of pain perception such as fibromyalgia and epilepsy.

Additionally compounds of Formula I are useful as modulators of the CRF receptor in the treatment of a number of gastrointestinal, cardiovascular, hormonal, autoimmune and inflammatory conditions. Such conditions include ulcers, spastic colon, diarrhea, post operative ilius and colonic hypersensitivity associated with psychopathological disturbances or stress, hypertension, tachycardia, congestive heart failure, infertility, euthyroid sick syndrome, inflammatory conditions effected by rheumatoid arthritis and osteoarthritis, pain, asthma, psoriasis and allergies.

Compounds of Formula I are also useful as modulators of the CRF1 receptor in the treatment of animal disorders associated with aberrant CRF levels. These conditions include porcine stress syndrome, bovine shipping fever, equine paroxysmal fibrillation, and dysfunctions induced by confinement in chickens, sheering stress in sheep or human-animal interaction related stress in dogs, psychosocial dwarfism and hypoglycemia.

Typical subjects to which compounds of Formula I may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

Pharmaceutical Preparations

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrathecal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired, other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, or flavoring or coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile an injectable solution or suspension in a non-toxic parentally acceptable dilutent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most CNS disorders, a dosage regimen of 4 times daily or less is preferred. For the treatment of stress and depression a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of Formula I will have certain pharmacological properties. Such properties include, but are not limited to oral bioavailability, optimal volume of distribution, low toxicity, low serum protein binding, and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120–1127).

As discussed above, preferred arylpyridines of Formula I exhibit activity in standard in vitro CRF receptor binding assays, specifically the assay as specified in Example 11, which follows. References herein to "standard in vitro receptor binding assay" are intended to refer to that protocol as defined in Example 11 which follows. Generally preferred arylpyridines of Formula I have an $IC_{50}$ of about 1 micromolar or less, still more preferably and $IC_{50}$ of about 100 nanomolar or less even more preferably an $IC_{50}$ of about 10 nanomolar or less or even 1 nanomolar or less in such a defined standard in vitro CRF receptor binding assay as exemplified by Example 11 which follows.

EXAMPLES

Preparation of 5-substituted-2-arylpyridines

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference for their teaching regarding the synthesis of arylpyridine compounds. Preferred methods for the preparation of compounds of the present invention include, but are not limited to, those described in Scheme I to Scheme V. Those who are skilled in the art will recognize that the starting materials may be varied and additional steps employed to produce compounds encompassed by the present invention. The following abbreviations are used herein:

| | |
|---|---|
| Bz | benzyl |
| Cmp# | Compound number |
| DPPA | diphenylphosphoryl azide |
| DME | dimethyl ethane |
| DMF | dimethyl formamide |
| EtOAc | Ethyl Acetate |
| Fe(acac)$_3$ | Iron tri-acetylacetonate |
| M-CPA | m-chloroperoxybenzoic acid |
| NaBH(OAc)$_3$ | Sodium triacetoxyborohydride |
| NMP | N-methyl pyrrolidinone |
| Pd/C | Palladium carbon catalyst |
| Pd$_2$dba$_3$ | Tris(dibenzylideneacetone)-dipalladium(0) |
| Pd(PPh$_3$)$_4$ | tetrakis(triphenylphosphine)palladium |
| P(t-Bu)$_3$ | tri-t-butyl phosphate |
| SPE Column | Solid-phase extraction column |
| t-BuOK | Potassium tertiary butoxide |

Tf$_2$O-Triflic anhydride

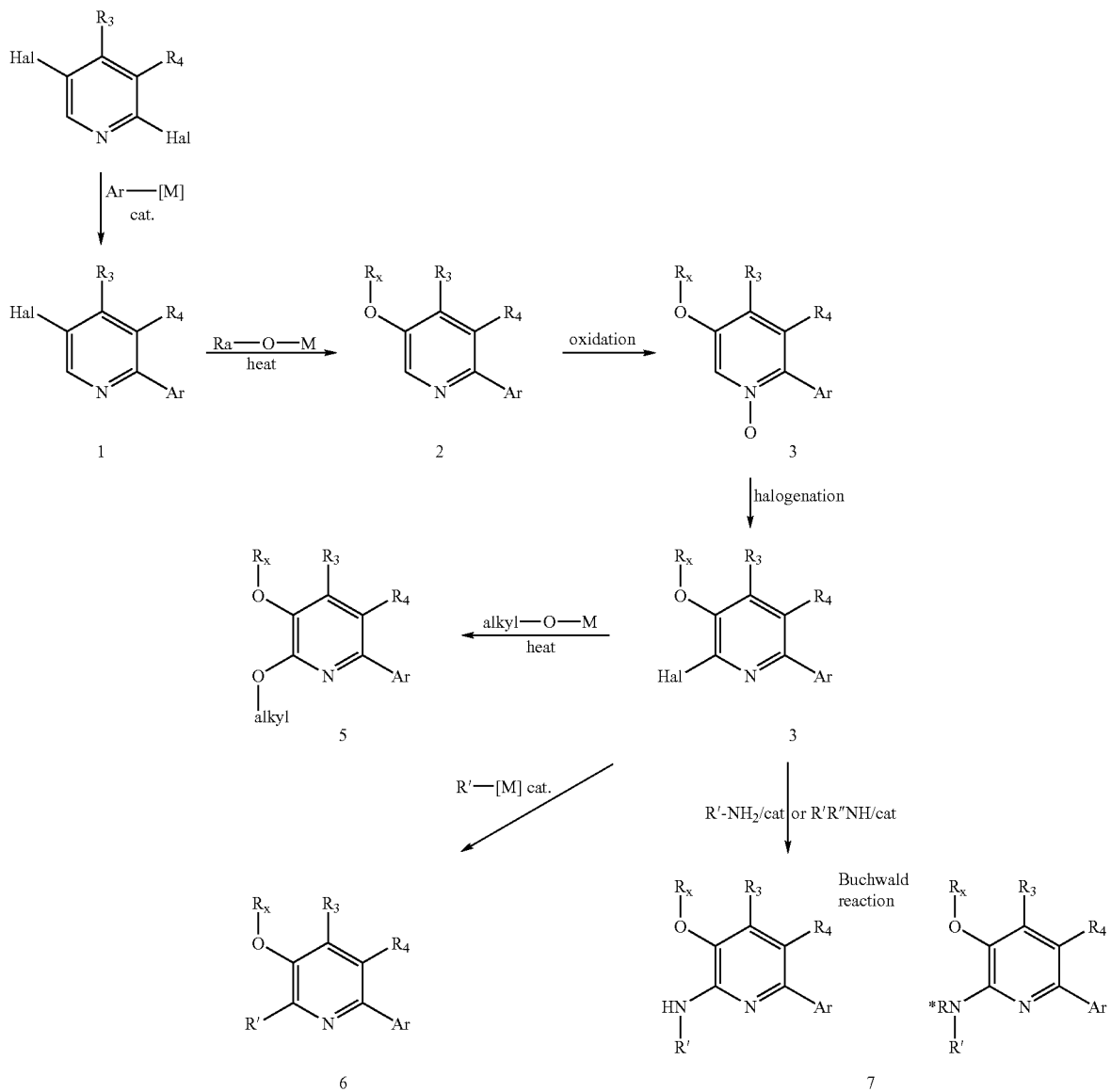

Scheme I

Selective metal catalyzed cross couplings of the 2,5-dihalopyridine afford 5-halo-2-arylpyridines 1. The desired 3-alkoxy-6-arylpyridine 2 is obtained by heating the 5-halo-2-arylpyridines with alkoxide. The 3-alkoxy-6-arylpyridine 2 is converted to the N-oxide in m-CPBA at room temperature. The intermediate, 2-halo-3-alkoxy-6-arylpyridine 4, is then obtained from the N-oxide 3 by heating in POCl$_3$. Conversion of the 2-halopyridne provides the compounds, for example 2,3-dialkoxy-6-arylpyridine 5 by nucleophilic substitution, 2-alkyl-3-alkoxy-6-arylpyridine 6 by cross coupling and 2-amino-3-alkoxy-6-arylpyridine 7 by amination.

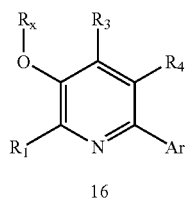

3-Alkoxypyridines are also synthesized by alkylation of 3-pyridinols by the method shown in Scheme II. Starting with 2-aminopyridine 8, nitration of the 5-position, followed by hydroxy dediazatization yields 2-pyridinol 9 which is further converted to 2-chloropyridine 10 Cross coupling of the resulting chloride gives the appropriate 6-arylpyridine 12, which is reduced to 5-aminopyridine 13 by hydrogenation. Hydroxy dediazatization gives the desired 3-pyridinol 14. Alkylation of 14 provides the target 3-alkoxy-6-arylpyridine compounds 16.

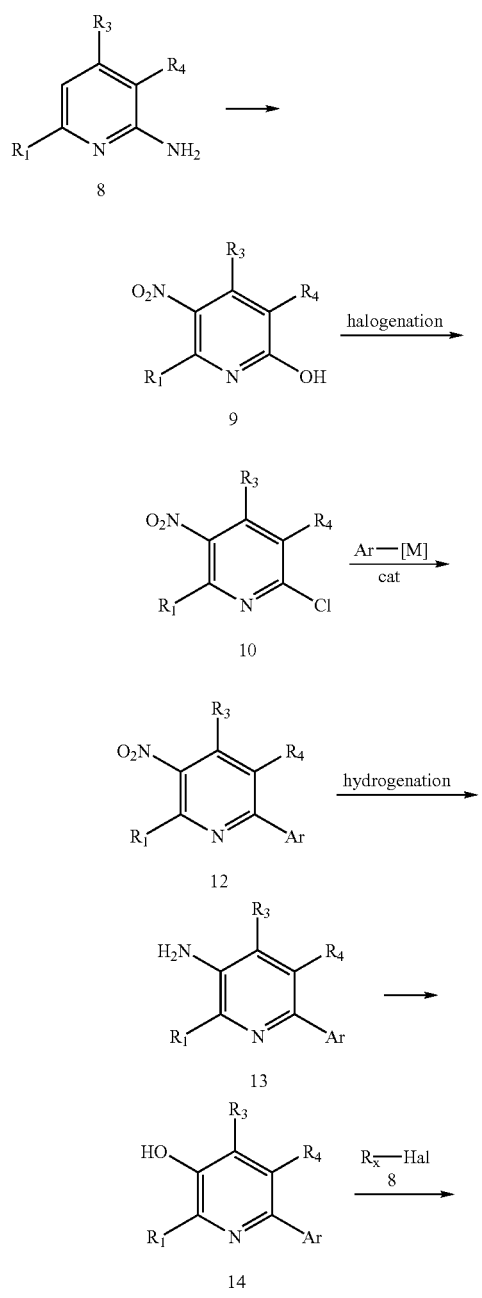

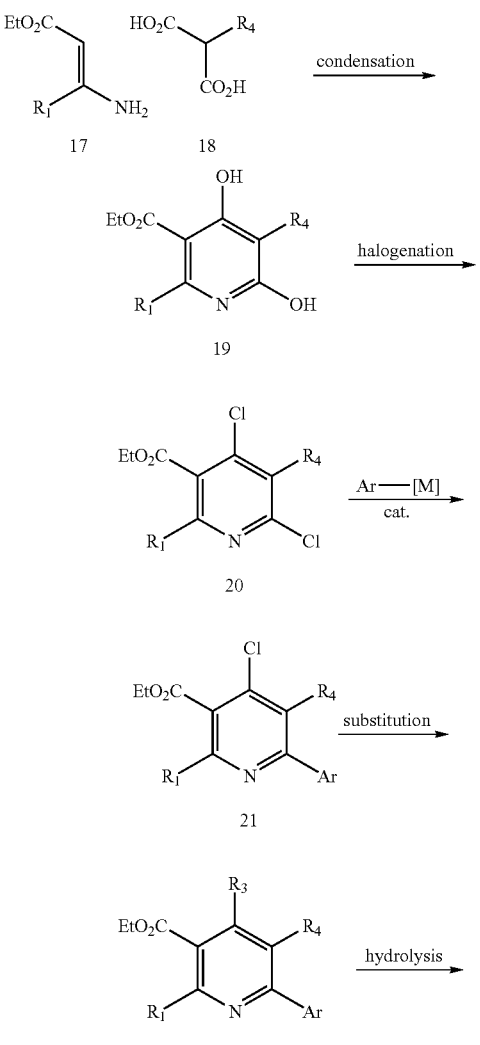

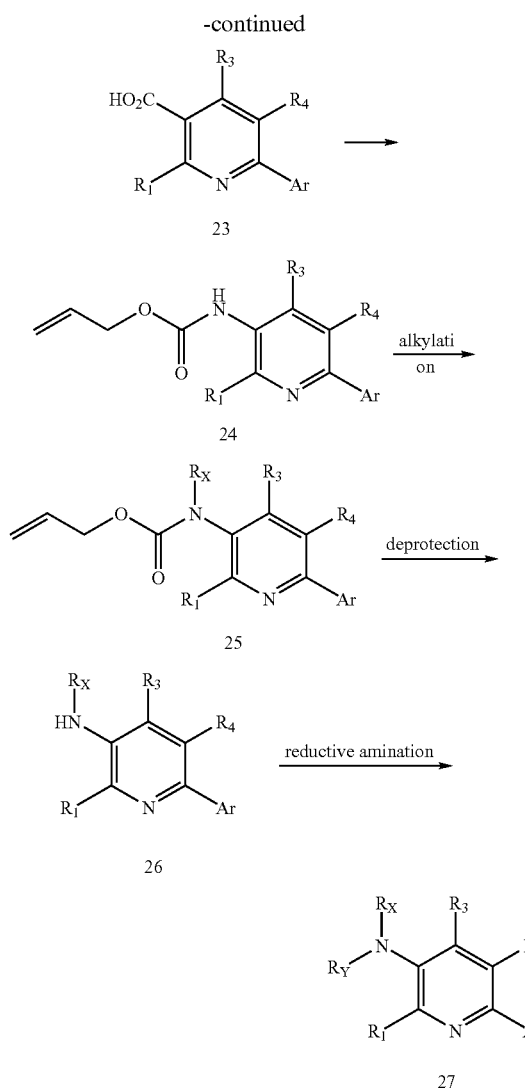

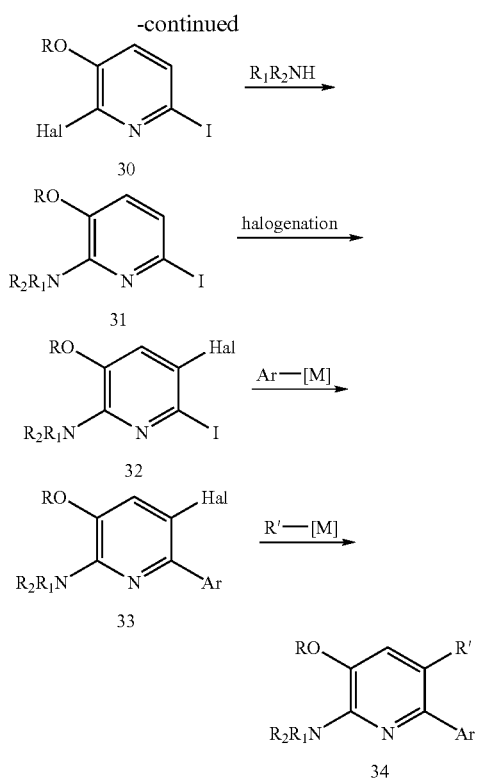

Arylpyridines may also be synthesized by construction of the pyridine ring as shown in Scheme III. Condensation of malonic acids with amines gives dihydroxypyridine 19 which is easily converted into 2,4-dichloropyridine 20. Selective cross coupling is achieved to afford 2-aryl-4-chloropyridine 21. $R_3$ is introduced by simple substitution to give 22 which is then hydrolyzed to afford the acid 23. Curtius rearrangement, followed by protection of the aniline gives arylpyridine 24. Alkylation of the amide is followed by deprotection and reductive alkylation to give the target compounds 27.

Alternatively, 2-amino-3-alkoxy-6-arylpyridines are synthesized from 2-halo-3-pyridinols as shown in Scheme IV. Iodination of 2-halo-3-pyridinol 28 gives 2–5 halo-6-iodo-3-pyridinol, which is easily alkylated to afford the corresponding 3-alkoxypyridines. By carefully applying chemoselectivity between 2-halo and 6-iodo, amination is achieved exclusively at the 2-position of the pyridine to afford 2-amino-3-alkoxy-6-iodopyridine 31. Further halogenation introduces 5-halo substituted pyridines 32. By metal catalyzed cross coupling, aryl substitutents are regioselectively introduced at the 6-position of the pyridine. Another step of cross coupling yields the target compounds 34.

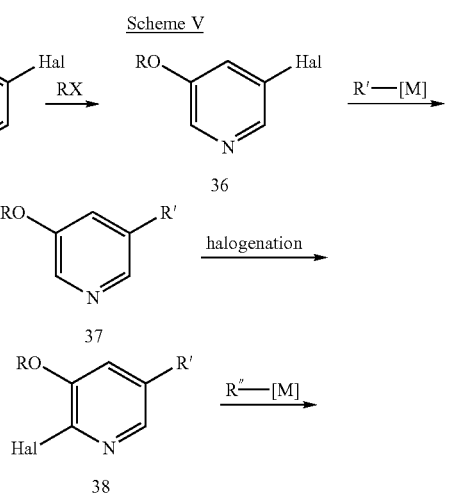

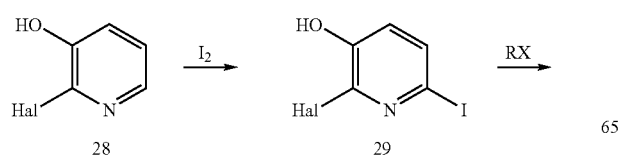

-continued

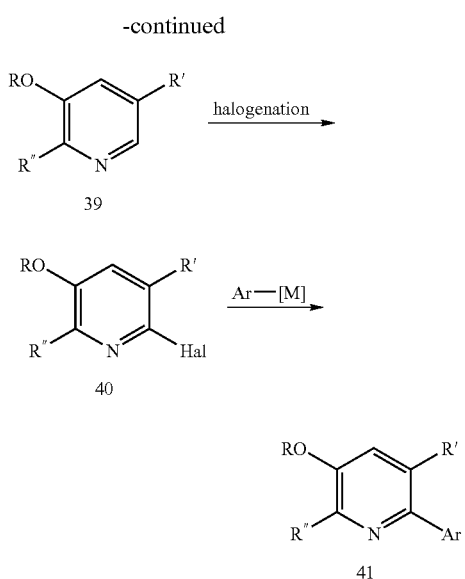

Furthermore, as shown in Scheme V, starting from 3-halo-5-pyridinol, 2,5–15 dialkyl-3-alkoxy-6-arylpyridines are synthesized in six steps. Alkylation of the pyridinol 35 gives 3-halo-5-alkoxypyridines 36, which undergo metal catalyzed cross coupling to give 3-alkoxy-5-alkylpyridine 37. Halogenation of the 2-position of pyridine ring give 2-halo-3-alkoxy-5-alkylpyrine. Cross coupling of the resulting 2-halo-3-alkoxy-5-alkylpyrine 38 yields 2,3,5-trisubstituted pyridine 39. Halogenation of 39, followed by metal catalyzed cross coupling give target pyridine derivative 41.

The preparation of the compounds of the present invention is illustrated further by the following examples, which are not to be construed as limiting the invention in scope or to the specific procedures and compounds described in them.

Commercial reagents are used without further purification. Room or ambient temperature refers to 20 to 25° C. Concentration in vacuo implies the use of a rotary evaporator. TLC refers to thin layer chromatography. Silica gel is used for purification of reaction products by column chromatography. Proton nuclear magnetic resonance ($^1$H NMR) spectral data are obtained at 300 or 400 MHz in CDCl$_3$, and reported as ppm, unless otherwise stated. Mass spectral data are obtained either by CI or APCI methods.

Example 1

Preparation of 3-methyl-5-(1-ethyl-propoxy)-2-(2-methoxy-4-trifluoromethoxy-phenyl)-6-ethyl-pyridine and 3-methyl-5-(1-ethyl-propoxy)-2-(2-methoxy-4-trifluoromethoxy-phenyl)-6-methylamino-pyridine

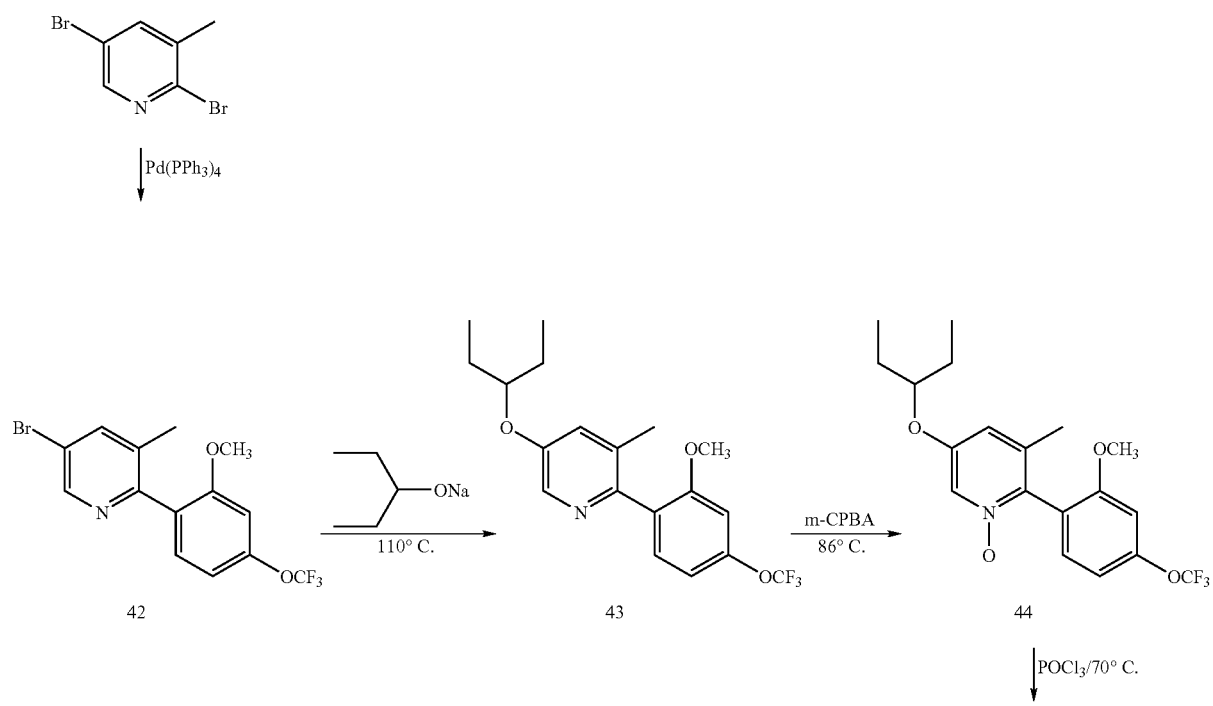

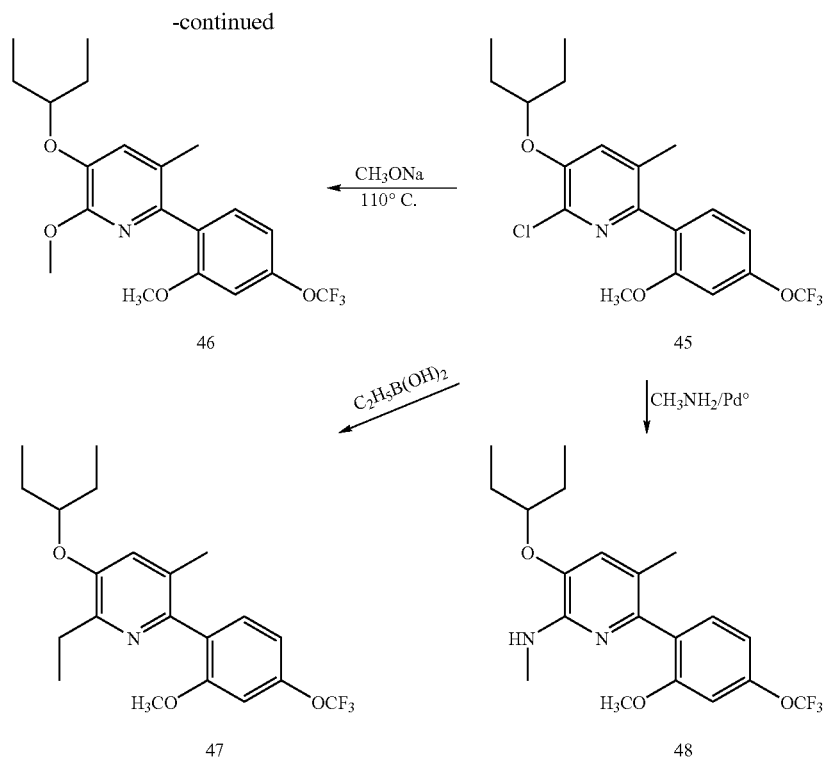

Step 1. 5-Bromo-2-(2-methoxy4-trifluoromethoxyphenyl)-3-methylpyridine (42).

Pd(PPh₃)₄ (1.15 g, 0.996 mmol) is added to a solution of 2,5-dibromo-3-methylpyridine (10 g, 39.85 mmol) in toluene (100 ml), followed by the addition of 2-methoxy-4-trifluorormethoxyphenylboronic acid (9.6 g, 39.85 mmol) and Na₂CO₃ (1M, 50 ml, 50 mmol). The resulting mixture is heated to reflux overnight, and then cooled to room temperature. The toluene layer is separated. The aqueous layer is extracted with EtOAc. The organic layers are combined, washed with water, brine, dried, filtered, and evaporated. The crude product is purified by chromatography (eluted with 6% EtOAc in hexane) to give the product as colorless oil. ¹H NMR (CDCl₃) δ 2.14 (s, 3H), 3.77 (s, 3H), 6.81(s, 1H), 6.92 (dd, 1H), 7.27 (d, J=8.4 Hz, 1H), 7.72 (s, 1H), 8.56 (s, 1H). LCMS 362, 364 (M+1).

Step 2. 5-(1-Ethylpropoxy)-2-(2-methoxy-4-trifluoromethoxyphenyl)-3-methylpyridine (43)

Compound 42 (3.62 g, 10 mmol) is added to a solution of sodium 3-pentoxide in NMP (1M, 30 ml, 30 mmol). The resulting mixture is heated to 120° C. for 2.5 h, and then cooled to room temperature, diluted with 50% EtOAc in hexane, washed with water, brine, dried, filtered and evaporated. The crude product is purified by chromatography (eluted with 6% EtOAc in hexane) to give the product as colorless oil. ¹H NMR (CDCl₃) δ 0.98 (t, J=7.6 Hz, 6H), 1.72 (m, 4H), 2.15 (s, 3H), 3.77 (s, 3H), 4.17 (m, 1H), 6.79 (s, 1H), 6.91 (dd, 1H), 7.07 (d, J=1.6 Hz, 1H), 7.27 (d, J=8.4 Hz, 1H), 8.18 (d, J=1.6 Hz, 1H). LCMS 370.2 (M+1).

Step 3. 5-(1-Ethylpropoxy)-2-(2-methoxy-4-trifluoromethoxyphenyl)-3-methylpyridine-1-oxide (44)

M-CPBA (314 mg, 77%, 1.4 mmol) is added to a solution of compound 43 (410 mg, 1.11 mmol) in CH₂Cl₂ (5 ml). The resulting solution is stirred at room temperature for 3 hours, and then evaporated to dryness. The residue is dissolved in EtOAc, washed with Na₂CO₃ (1M), water, brine, dried, filtered and evaporated. The crude product is purified by chromatography (eluted with EtOAc) to give the product as a white crystalline solid. ¹H NMR (CDCl₃) δ 0.97 (t, J=7.6 Hz, 6H), 1.71 (m, 4H), 2.02 (s, 3H), 3.79 (s, 3H), 4.09 (m, 1H), 6.78 (d, J=1.2 Hz, 1H), 6.84 (s, 1H), 6.92 (dd, 1H), 7.21 (d, J=8.4 Hz, 1H), 7.95 (d, J=1.2 Hz, 1H). LCMS 386 (M+1).

Step 4. Preparation of 2-Chloro-3-(1-ethylpropoxy)-6-(2-methoxy-4-trifluoromethoxyphenyl)-5-methylpyridine (45)

A solution of compound 44 (340 mg, 0.88 mmol) in POCl₃ (0.4 ml) is stirred at 65° C. for 1 hour, then cooled to room temperature and poured onto ice (10 g). The resulting solution is neutralized with Na₂CO₃, and extracted with 50% EtOAc in hexane. The combined extracts are washed with water, brine, dried, filtered and evaporated. The crude product is purified by chromatography (eluted with 6% EtOAc in hexane) to give the product as a white crystalline solid. ¹H NMR (CDCl₃) δ 1.01 (t, J=7.6 Hz, 6H), 1.76 (m, 4H), 2.12 (s, 3H), 3.78 (s, 3H), 4.19 (m, 1H), 6.78 (s, 1H), 6.89 (dd, 1H), 7.05 (s, 1H), 7.26 (s, 1H), 7.27 (d, J=8.4 Hz, 1H). LCMS 404.27 (M+1).

Step 5. 2-Methoxy-3-(1-ethylpropoxy)-6-(2-methoxy-4-trifluoromethoxyphenyl)-5-methylpyridine (46)

Sodium methoxide in methanol (25 w/w %, 0.5 ml) is added to a solution of compound 45 (50 mg, 0.124 mmol) in NMP (0.5 ml). The resulting mixture is heated to 100° C. overnight, then cooled to room temperature, diluted with 50% EtOAc in hexane, washed with water, brine, dried, filtered and evaporated. The crude product is purified by chromatography (eluted with 6% EtOAc in hexane) to give the product as colorless oil. ¹H NMR (CDCl₃) δ 1.00 (t, J=7.6 Hz, 6H), 1.75 (m, 4H), 2.04 (s, 3H), 3.80 (s, 3H), 3.94

(s, 3H), 4.12 (m. 1H), 6.78 (s, 1H), 6.89 (dd, 1H), 6.92 (s, 1H), 7.30 (d, J=8.4 Hz, 1H). LCMS 400.4 (M+1).

Step 6. 2-Ethyl-3-(1-ethylpropoxy)-6-(2-methoxy-4-trifluoromethoxyphenyl)-5-methylpyridine (47)

Pd(PPh$_3$)$_4$ (12 mg, 0.01 mmol) is added to a solution of compound 45 (41 mg, 0.1 mmol) in toluene (0.6 ml), followed by ethylboronic acid (73 mg, 1 mmol) and Na$_2$CO$_3$ (1M, 0.2 ml, 0.2 mmol). The resulting mixture is heated to reflux overnight, and then cooled to room temperature. The toluene layer is separated. The aqueous layer is extracted with EtOAc. The combined organic layers are combined, washed with water, brine, dried, filtered and evaporated. The crude product is purified by chromatography (eluted with 6% EtOAc in hexane) to give the product as a white crystalline solid. $^1$H NMR (CDCl$_3$) δ 1.00 (t, J=7.6 Hz, 6H), 1.23 (t, J=7.6 Hz, 3H), 1.73 (m, 4H), 2.09 (s, 3H), 2.84 (q, J=7.6 Hz, 2H), 3.87 (s, 3H), 4.16 (m, 1H), 6.78 (s, 1H), 6.89 (dd, 1H), 6.92 (s, 1H), 7.27 (d, J=8.4 Hz, 1H). LCMS 398.34 (M+1).

Step 7. [3-(1-Ethylpropoxy)-6-(2-methoxy-4-trifluoromethoxyphenyl)-5-methylpyridin-2-yl]-methylamine (48)

Pd$_2$dba$_3$ (4 mg) is added to a solution of compound 45 (70 mg, 0.173 mmol) in toluene (1 ml), followed by the addition of P(t-Bu)$_3$ (1.4 mg), methylamine (2M in THF, 0.17 ml, 0.347 mmol) and t-BuOK (1M in THF, 0.26 ml, 0.26 mmol). The resulting mixture is sealed and heated to 55° C. overnight, then cooled to room temperature. The reaction mixture is diluted with 30% EtOAc in hexane, washed with water, brine, dried, filtered and evaporated. The crude product is purified by chromatograph (eluted with 6% EtOAc in hexane) to give the product 48 as a light yellow solid. $^1$H NMR (CDCl$_3$) δ 0.97 (t, J=7.6 Hz, 6H), 1.71 (m, 4H), 1.98 (s, 3H), 2.99 (s, 3H), 3.79 (s, 3H), 4.13 (m, 1H), 4.77 (brs, 1H), 6.67 (s, 1H), 6.77 (s, 1H), 6.87 (dd, 1H), 7.32 (d, J=8.4 Hz, 1H). LCMS 399.4 (M+1).

Example 2

Preparation of 3-ethyl-5-(1-ethyl-propoxy)-2-(2-methoxy-4-trifluoromethoxy-phenyl)-6-methyl-pyridine

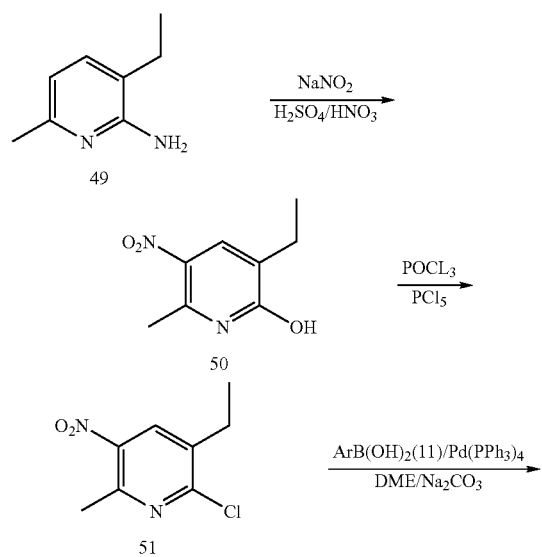

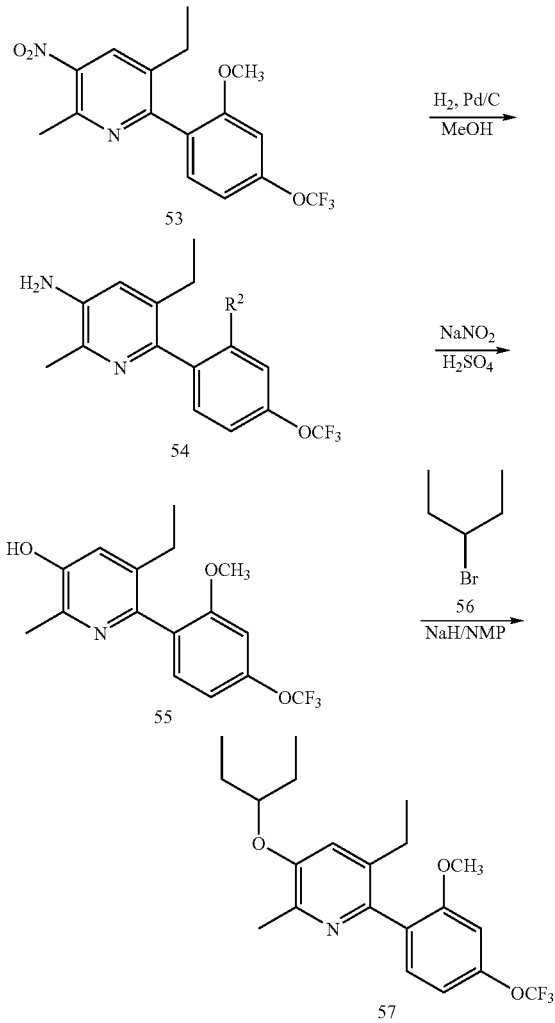

A solution of NaNO$_2$ (2.1 g) in water (3.8 ml) is added drop-wise over 3 hours, at 30 degrees C., to a mixture containing compound 49 (4.2 g) dissolved in concentrated sulfuric acid (7.6 ml), or alternatively concentrated nitric acid, and water (5.7 ml). The mixture is then heated to 80 degrees C. for 1 hour, cooled to room temperature, diluted with water (about 20 ml) and filtered to give pale yellow solid, 50. MS, 181 (M–H).

A mixture of POCl$_3$ (3.8 ml), PCl$_5$ (7.5 g) and compound 50 (4.3 g) is heated to 110 degrees C. for 5 hours. After cooling to room temperature, the mixture is poured into ice-water. Solids are filtered and the aqueous filtrate is extracted with ether. The ether extract is concentrated and purified by flash chromatography to give yellow oil, 51. NMR, 8.19(s, 1H), 2.82(s, 3H), 2.81(q, 2H), 1.30(t, 3H).

Compound 51 (201 mg) is combined with 2-methoxy-4-trifluoromethoxybenzeneboronic acid (248 mg) and aqueous sodium carbonate (1M, 2.8 ml) in DME (5.6 ml). The mixture is degassed by bubbling in nitrogen gas for 1 minute. Fresh Pd(PPh$_3$)$_4$ (48 mg) is added. The mixture is heated to 80 degrees C. for 6 hours, then poured into water and extracted with toluene. The extract is concentrated and purified by flash chromatography, with 10% ethyl acetate in hexanes as eluant, to give yellow oil, 53 (200 mg). NMR, 8.22(s, 1H), 7.27(d, 1H), 6.95(d, 1H), 6.83 (s, 1H), 3.78(s, 3H), 2.86(s, 3H), 2.51(b, 2H), 1.14(t, 3H).

Compound 53 (180 mg) is dissolved in methanol (10 ml) containing 10% Pd/C (10 mg) and hydrogenated at 40 psi with a Parr shaker. The solution is filtered and concentrated to give 54, which can be subsequently used without further purification. MS, 327 (M+1).

Compound 54 (203 mg) is dissolved in a solution of concentrated sulfuric acid (70 microliters) and water (0.6 ml), cooled to 0 degrees C., and treated by drop-wise addition of NaNO$_2$ (59 mg) in water (0.5 ml). The mixture is stirred for 8 hours at room temperature, basified with NaHCO$_3$ (5 ml) and extracted with ethyl acetate. The extract is concentrated to give yellow solid, 55. MS, 328 (M+1).

NaH (60%, 57 mg) is added to compound 55 (200 mg) dissolved in NMP (2.5 ml). After gas evolution ceases, 3-bromopentane (56) is added and the mixture is stirred at 85 degrees C. for 5 hours. The mixture is into water and extracted with ethyl acetate. The product is purified and concentrated by preparative TLC using 20% ethyl acetate in hexanes as eluant to give compound 57. MS, 398 (M+H); NMR, 7.24(d, 1H), 6.95(s, 1H), 6.89(d, 1H), 6.77(s, 1H), 4.16(m, 1H), 3.76(s, 3H), 2.43(s, 3H), 2.39(m, 2H), 2.74(m, 4H), 1.06(t, 3H), 0.99(t, 6H).

Example 3

Preparation of [5-ethyl-6-(2-methyl-4-methoxy-phenyl)-2-methyl-pyridin-3-yl]-dipropyl-amine

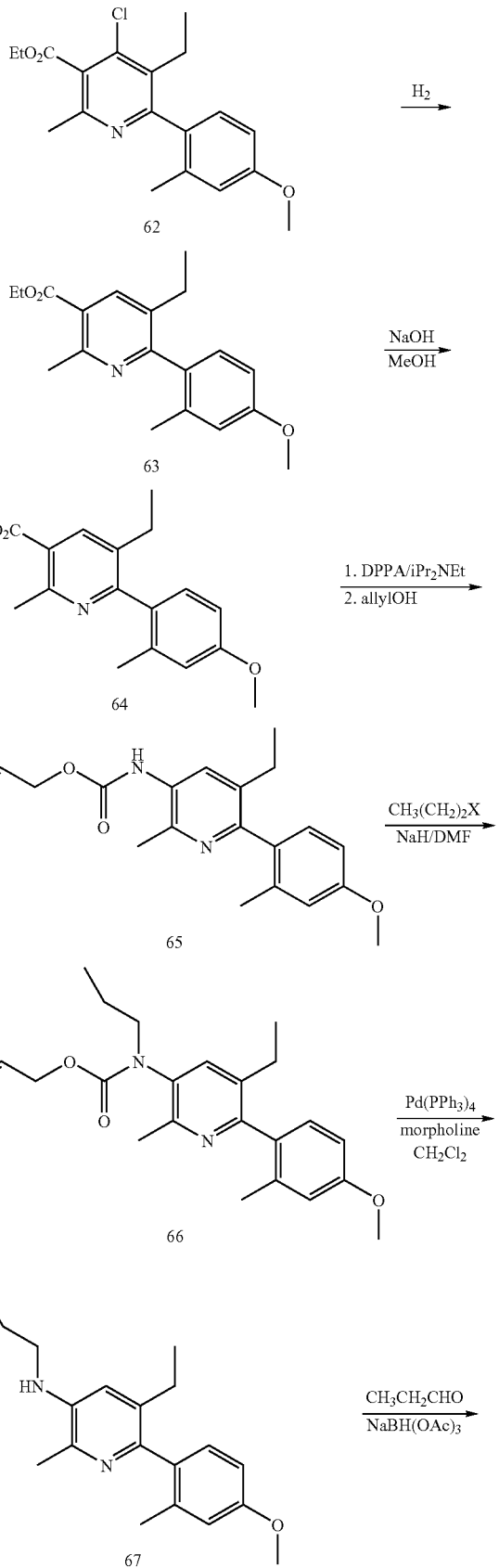

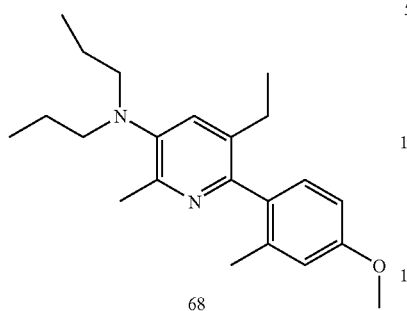

68

A mixture of compounds 58 (2.6 g) and 59 is heated to 105 degrees C. for 1.5 hours in acetic anhydride (30 ml) (Procedure given in J. Prakt. Chem., 82, 619). The mixture is concentrated, dissolved in NaOH (4N, 100 ml), heated to 100 degrees C. for 1.5 hours, cooled and acidified to pH 4. The precipitate is filtered and dried to give 60.

Compound 60 (4 g) is heated to 100 degrees C. for 8 hours in $POCl_3$ (20 ml) and $Me_4NCl$ (4 g). The mixture is concentrated, diluted with water and extracted with ether/hexanes. The extract is concentrated to give 61 as a colorless oil.

Compound 61 (200 mg), 4-methoxy-2-methylbenzeneboronic acid, and aqueous sodium carbonate (1M, 2.5 ml) in DME (5.5 ml) are combined. The mixture is degassed by bubbling in nitrogen gas for 1 minute followed by addition of fresh $Pd(PPh_3)_4$ (30 mg). The mixture is heated to 80 degrees C. for 1 hour, poured into water, and extracted with toluene. The extract is concentrated and purified by flash chromatography, with 20% ethyl acetate in hexanes as eluant, to give compound 62 (200 mg).

A mixture of compound 62 (200 mg), $HCO_2^-NH_4^+$ (400 mg) and 10% Pd/C (20 mg) is refluxed in methanol (5 ml) for 2 hours. The mixture is filtered and concentrated to give compound 63.

Compound 63 (0.5 g) is dissolved in NaOH (1M, 5 ml) and methanol (5 ml), and heated to reflux for 8 hours. After cooling, the solution is diluted with water, acidified to pH 3 and extracted with dichloromethane. The extract is concentrated to give compound 64.

Compound 64 (150 mg) is dissolved in a mixture of toluene (2 ml) containing diisopropylethylamine (0.2 ml) and DPPA (0.17 ml). The solution is stirred for 1.5 hours at room temperature, then heated to 100 degrees C. for 10 minutes to purge nitrogen. Allyl alcohol (0.2 ml) is then added and the heating continued for 0.5 hour. The reaction mixture is cooled, diluted with water, extracted with toluene, concentrated and purified by flash chromatography to give compound 65.

Sodium hydride (60%, 50 mg) is added to a solution of compound 65 (140 mg) in dimethylformamide (2 ml). After stirring at room temperature for 5 minutes, iodopropane (60 microliters) is added. Stirring is continued for 0.5 hour. The mixture is diluted with water, extracted with toluene, concentrated and purified through an SPE column with hexanes/ether to give compound 66.

$Pd(PPh_3)_4$ (25 mg) is added to a solution of compound 66 (180 mg) in dichloromethane (2 ml) and morpholine (100 microliter). The mixture is stirred at room temperature for 0.5 hour and filtered through an SPE column to give compound 67 as a colorless oil.

A mixture of compound 67 (0.07 mmole), propanal (0.14 mmole) and $NaBH(OAc)_3$ (0.21 mmole) in dichloroethane (1 ml) is heated to 40 degrees C. for 24 hours. The mixture is quenched with sodium hydroxide (1N, 2 drops), stirred vigorously and filtered though an SPE column to give compound 68 MS 341 M(M+H). NMR 7.24(s, 1H), 7.11(d, 1H), 6.79(s, 1H), 6.77(d, 1H), 3.82(s, 3H), 2.96(q, 4H), 2.51 (s, 3H), 2.35(q, 2H), 2.08(s, 3H), 1.49(m, 4H), 1.03(t, 3H), 0.90(t, 6H).

Example 4

Preparation of [3,2'-diethyl-5-(1-ethyl-propoxy)-6'-isopropyl-[2,3']bipyridinyl-6-yl]-methyl-amine (36) and [2'-ethoxy-3-ethyl-5-(1-ethyl-propoxy)-6'-isopropyl-1',2'-dihydro-[2,3']bipyridinyl-6-yl]-methyl-amine (34)

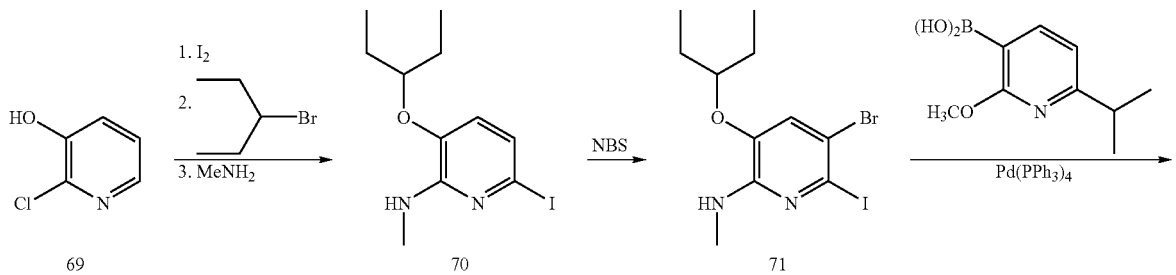

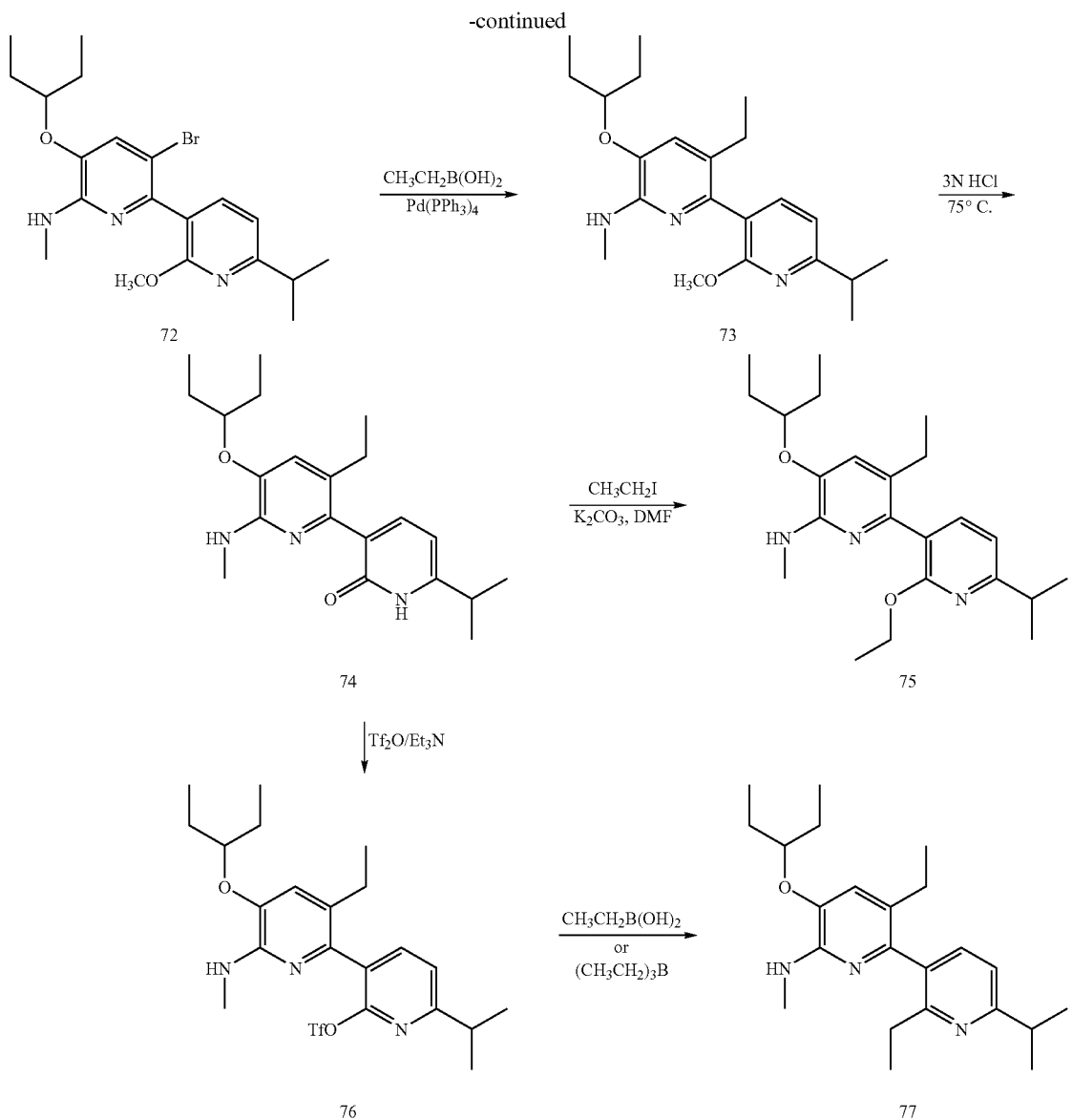

Step 1. Preparation of [3-(1-ethyl-propoxy)-6-iodo-pyridin-2-yl]-methyl-amine

I$_2$ (45.8 g, 0.18 mol) is added to a solution of 2-chloro-3-pyridinol (69, 23.4 g, 0.18 mol) in Na$_2$CO$_3$ (225 ml, 1.0M aqueous solution, 0.225 mol). The I$_2$ initially remains in the bottom of the flask but dissolves with stirring overnight. The solution becomes lighter in color dark and a white solid precipitates. The mixture is then diluted with EtOAc and acidified with concentrated HCl to pH 2–3. The solution is extracted with EtOAc. The combined extracts are washed with H$_2$O, dried, evaporated to give the 2-chloro-5-iodo-3-pyridinol as a yellow solid.

The solid is dissolved in DMF (300 ml). Solid K$_2$CO$_3$ (40 g) and 3-bromopentane (44.8 ml, 2 eq) are added to this solution. The resulting mixture is heated to 90° C. with gentle reflux for 2–4 hrs, then cooled to room temperature., poured into 5% EtOAc/hexane, washed with H$_2$O several times, and dried. The solvent is removed to give an oil which is used without further purification in the next step.

The above oil (40 g) is dissolved in CH$_3$NH$_2$ (4N in NMP, 85 ml, 3 eq), sealed, and heated to 100° C. for 2 days. The mixture is then diluted with 5% EtOAc in hexane, washed with H$_2$O several times and dried. Solvent is removed to give a dark green oil. Crystals formed on cooling. The mixture of oil and crystals is filtered. The solid is washed with hexane and dried to give compound 70 as light green crystalline solid. The filtrate was collected to give an oil which is purified by column chromatography (3% EtOAc/hexane) to give additional solid product ([3-(1-ethyl-propoxy)-6-iodo-pyridin-2-yl]-methyl-amine). MS 321.2 (M+1). $^1$H NMR (CDCl$_3$) δ ppm 0.92 (t, 6H), 1.65 (m, 4H), 2.98 (d, 3H), 4.04 (m, 1H), 4.94 (brs, 1H), 6.43 (d, 1H), 6.82 (d, 1H).

Step 2. Preparation of [3-(1-ethyl-propoxy)-5-bromo-6-iodo-pyridin-2-yl]-methyl-amine NBS (11.67 g, 65.59 mmol) is added to a solution of 70 (20 g, 62.47 mmol) in CHCl$_3$ (240 ml) at 0° C., warmed to room temperature, stirred for 20 minutes, and then evaporated to remove the CHCl$_3$. 6% EtOAc in hexane is added to the residue and washed with saturated NaHCO$_3$, H$_2$O, dried, and evaporated. The crystals which form are collected by filtration. The solid is washed with hexane and dried to give compound 71 as light brown solid. The filtrate is then purified by column (1% EtOAc in hexane) to provide additional product. MS 399.2, 401.2 (M+1). $^1$H NMR (CDCl$_3$) δ ppm 0.92 (t, 6H), 1.67 (m, 4H), 2.98 (d, 3H), 4.06 (m, 1H), 4.94 (brs, 1H), 6.84 (s, 1H).

Step 3. Preparation of [3-bromo-5-(1-ethyl-propoxy)-2'-Methoxy-6'-isopropyl-[2,3']bipyridinyl-6-yl]-methyl-amine Pd(PPh$_3$)$_4$ (2.5 Mol %) is added to a solution of compounds 71 in DME. The mixture is stirred at room temperature for 20 minutes. 2-Methoxy-6-isopropyl-3-pyridylboronic acid (1.9 g, 9.74 mmol) is added, followed by Na$_2$CO$_3$ (17.7 ml, 1M, 17.7 mmol). The resulting mixture is heated to reflux overnight. After cooling to room temperature, the mixture is diluted with 30% EtOAc in hexane, and then washed with H$_2$O and brine. The crude is purified by column chromatography (eluted with 4% EtOAc in hexane) to give compound 72 as white crystalline solid. MS 422.3, 424.3 (M+1). $^1$H NMR (CDCl$_3$) δ ppm 0.96 (t, 6H), 1.30 (d, 6H), 1.71 (m, 4H), 2.97 (m, 1H), 2.98 (d, 3H), 3.96 (s, 3H), 4.12 (m, 1H), 4.94 (brs, 1H), 6.80 (d, 1H), 6.96 (s, 1H), 7.50 (d, 1H).

Step 4. Preparation of [3-ethyl-5-(1-ethyl-propoxy)-2'-Methoxy-6'-isopropyl-[2,3']bipyridinyl-6-yl]-methyl-amine Pd(PPh$_3$)$_4$ (2.5 Mol %) is added to a solution of the above compound 72 (1.7 g, 4 mmol) in toluene (25 ml) and stirred at room temperature for 20 minutes. Ethylboronic acid (3.0 g, 40 mmol) is added, followed by Na$_2$CO$_3$ (8 ml, 1M, 8 mmol). The resulting mixture is heated to reflux for 2 hours. After cooling to room temperature, the mixture is diluted with 30% EtOAc in hexane, and then washed with H$_2$O and brine. The crude product is purified by column chromatography (eluted with 5% EtOAc in hexane) to give compound 73 as white crystalline solid. MS 372.4 (M+1). $^1$H NMR (CDCl$_3$) δ ppm 0.97 (t, 6H), 1.04 (t, 3H), 1.30 (d, 6H), 1.71 (m, 4H), 2.32 (q, 2H), 2.95 (m, 1H), 2.98 (d, 3H), 3.92 (s, 3H), 4.15 (m, 1H), 4.78 (m, 1H), 6.72 (s, 1H), 6.80 (d, 1H), 7.51 (d, 1H).

Step 5. Preparation of 3-Ethyl-5-(1-ethyl-propoxy)-6'-isopropyl-6-methylamino-1'H-[2,3']bipyridinyl-2'-one A mixture of the above compound 73 (600 mg, 1.6 mmol) in HCl (3.3 N, 3 ml) is heated to 75° C. for 10 hours. After cooling to room temperature, the mixture is basified with NaOH (10N) at 0° C. The resulting precipitate is collected by filtration. The solid is washed with H$_2$O and 5% EtOAc/hexane, and dried to give compound 74 as white crystalline solid (560 mg). MS 358.3 (M+1). $^1$H NMR (CDCl$_3$) δ ppm 0.97 (t, 6H), 1.10 (t, 3H), 1.28 (d, 6H), 1.71 (m, 4H), 2.52 (q, 2H), 2.80 (m, 1H), 2.99 (d, 3H), 4.13 (m, 1H), 4.80 (m, 1H), 6.16 (d, 1H), 6.73 (s, 1H), 7.51 (d, 1H).

Step 6. Preparation of [2'-Ethoxy-3-ethyl-5-(1-ethyl-propoxy)-6'-isopropyl-1',2'-dihydro-[2,3']bipyridinyl-6-yl]-methyl-amine K$_2$CO$_3$ (30 mg) is added a mixture of the above compound 74 (50 mg, 0.14 mmol) in DMF (1 ml), followed by the addition of EtI (0.017 ml). The mixture was stirred at room temperature for 8 hours, then diluted with H$_2$O, and extracted with 33% EtOAc/hexane. The combined extracts are washed with H$_2$O and brine, dried, and purified by column chromatography (eluted with 8% EtOAc/hexane) to give compound 75 as colorless oil. MS 386.3 (M+1). $^1$H NMR (CDCl$_3$) δ ppm 0.97 (t, 6H), 1.10 (t, 3H), 1.29 (d, 6H), 1.31 (t, 3H), 1.71 (m, 4H), 2.35 (q, 2H), 2.95 (m, 1H), 2.99 (d, 3H), 4.15 (m, 1H), 4.42 (q, 2H), 4.77 (m, 1H), 6.72 (s, 1H), 6.76 (d, 1H), 7.50 (d, 1H).

Step 7. Preparation of Trifluoro-acetic acid 3-ethyl-5-(1-ethyl-propoxy)-6'-isopropyl-6-methylamino-[2,3']bipyridinyl-2'-yl ester Tf$_2$O (0.009 ml, 0.05 mmol) is added to a solution of the above compound 74 (17 mg, 0.05 mmol) in CH$_2$Cl$_2$ (1 ml) at 0° C., followed by Et$_3$N (0.014 ml, 0.1 mmol). The mixture is stirred for 30 minutes, evaporated, diluted with H$_2$O, and extracted with 33% EtOAc/hexane. The combined extracts are washed with H$_2$O and brine, dried, and evaporated to give compound 76 as a light yellow crystalline solid (21 mg). MS 490.4 (M+1). $^1$H NMR (CDCl$_3$) δ ppm 0.97 (t, 6H), 1.06 (t, 3H), 1.30 (d, 6H), 1.71 (m, 4H), 2.35 (q, 2H), 2.98 (d, 3H), 3.06 (m, 1H), 4.17 (m, 1H), 4.87 (m, 1H), 6.71 (s, 1H), 7.22 (d, 1H), 7.75 (d, 1H).

Step 8. Preparation of [3,2'-Diethyl-5-(1-ethyl-propoxy)-6'-isopropyl-[2,3']bipyridinyl-6-yl]-methyl-amine Pd(PPh$_3$)$_4$ (2.5 Mol %) is added to a solution of the above compound 76 (15 mg, 0.03 mmol) in toluene (0.5 ml), and the mixture is stirred at room temperature. for 20 minutes. Triethylborane (1N in hexane, 0.09 ml, 0.09 mmol) is added, followed by Na$_2$CO$_3$ (0.06 ml, 1M, 0.06 mmol). Optionally, triethyl boronic acid (30 mmol) may be substituted for triethylborane. The resulting mixture is heated to 100° C. for 4 hours. After cooling to room temperature, the mixture is diluted with 30% EtOAc in hexane, and washed with H$_2$O and brine. The crude is purified by column chromatography (eluted with 10% EtOAc in hexane) to give compound 77 as white crystalline solid. MS 370.4 (M+1). $^1$H NMR (CDCl$_3$) δ ppm 0.99 (t, 6H), 1.01 (t, 3H), 1.18 (t, 3H), 1.32 (d, 6H), 1.72 (m, 4H), 2.25 (m, 2H), 2.64 (q, 2H), 2.96 (d, 3H), 3.08 (m, 1H), 4.17 (m, 1H), 4.81 (m, 1H), 6.72 (s, 1H), 7.02 (d, 1H), 7.40 (d, 1H).

Example 5

Preparation of 2,5-diethyl-3-(1-ethyl-propoxy)-6-(2-methoxy-4-trifluoromethoxy-phenyl)-pyridine

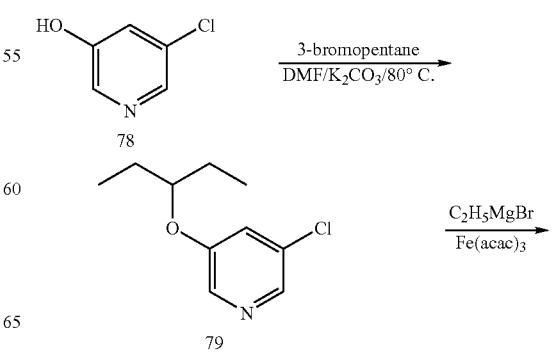

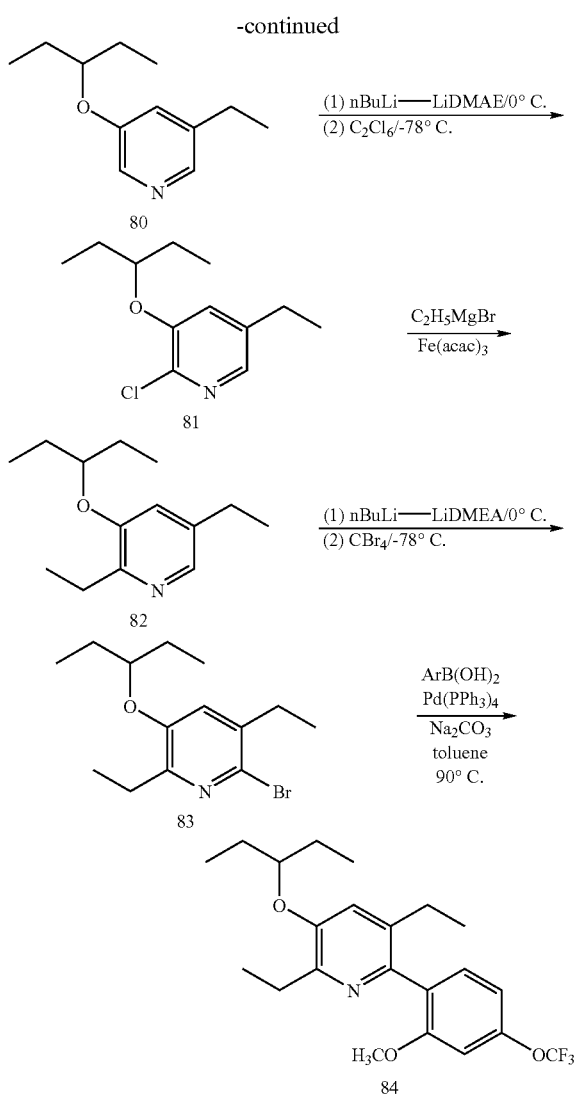

Step 1. Preparation of 3-Chloro-5-(1-ethyl-propoxy)-pyridine 5-chloro-3-pyridinol (10 g, 0.077 mol) (78) is dissolved in anhydrous DMF (200 ml). 3-bromopentane (14.0 g, 0.093 mol) and potassium carbonate (16.0 g, 0.115 mol) are added to the solution at room temperature. The resulting mixture is heated at 80° C. under N₂ atmosphere for 15 hours. The reaction mixture is cooled to room temperature, diluted with water (~200 ml) and extracted with ethyl acetate (150 ml, 3 extractions). The combined organic layers are washed with brine (150 ml) and dried with anhydrous sodium sulfate. Purification by flash column with 5% ethyl acetate in hexanes gives the product (79) as a slightly yellow liquid. ¹HNMR δ(ppm, CDCl₃) 8.17(d, J=2.4 Hz, 1H), 8.14 (d, J=1.6 Hz, 1H), 7.17(t, J=2.2 Hz, 1H), 4.13(1H, m, —CHEt₂), 1.69(m, 4H, 2X(—CH₂CH₃)), 0.95(t, J=7.2 Hz, 6H, 2X(—CH₂CH₃))

Step 2. Preparation of 3-Ethyl-5-(1-ethyl-propoxy)-pyridine

3-Chloro-5-(1-ethyl-propoxy)-pyridine (5.17 g, 0.026 mol) is dissolved in anhydrous THF/1-methyl-2-pyrrolidinone (NMP) (100 ml/10 ml). Fe(acac)₃ (457 mg, 5% mol) is added at room temperature. C₂H₅MgBr (3.0M in ether, 10.4 ml) is added dropwise at room temperature and stirred for 20 minutes. The reaction mixture was quenched with water (100 ml) and extracted with ethyl acetate (150 ml, 3 extractions), the combined organic layers are washed with brine (150) and dried with anhydrous sodium acetate. Purification by flash column chromatography with 10% ethyl acetate in hexanes yields product 80 as a slightly yellow liquid. ¹HNMR δ(ppm, CDCl₃): 8.11(d, J=2.7Hz,1H), 8.04(s, 1H), 7.01(s, 1H), 4.14(1H, m, —CHEt₂), 2.62(q, J=7.8 Hz, —CH₂CH₃), 1.64–1.73(m, 4H, 2X(—CH₂CH₃)), 1.24(t, J=7.8 Hz, 3H —CH₂CH₃), 0.96(t, J=7.5H, 6H, 2X(—CH₂CH₃))

Step 3. Preparation of 3-Ethyl-5-(1-ethyl-propoxy)-6-chloro-pyridine

A solution of 2-(dimethylamino)ethanol (3.48 ml, 0.035 mol) in anhydrous hexanes (40 ml) is treated with n-BuLi (43 ml, 1.6M in hexanes) at 0° C. and stirred at 0° C. for 30 minutes. 3-Ethyl-5-(1-ethyl-propoxy)-pyridine (80) (3.35 g, 0.017 mol) is added and stirred at 0° C. for 45 minutes. The resulting reaction mixture is cooled to −78° C. Hexachloroethane (10.26 g, 0.043 mol) is added as a solution in hexanes (60 ml). The resulting mixture is allowed to warm to 0° C. over a period of 1.5 hours. The reaction is quenched with water (80 ml) and extracted with ethyl acetate (100 ml) and dichloromethane (60 ml, 2 extractions). The combined organic layers are washed with brine (150 ml) and dried with anhydrous sodium sulfate. Purification by column choromatography with hexanes/ethyl acetate (1/20) gives product (81) as a colorless liquid. ¹HNMR δ(ppm, CDCl₃): 7.79(s, 1H), 7.00(s, 1H), 4.16(1H, m, —CHEt₂), 2.61(q, J=7.8 Hz, 2H —CH₂CH₃), 1.67–1.77(m, 4H, 2X(—CH₂CH₃)), 1.24(t, J=7.8 Hz, 3H, —CH₂CH₃), 0.98(t, J=7.2 Hz, 6H, 2X(—CH₂CH₃))

Step 4. Preparation of 3,6-Diethyl-5-(1-ethyl-propoxy)-pyridine

3-Ethyl-5-(1-ethyl-propoxy)-6-chloro-pyridine (81) (2.27 g, 0.01 mol) is dissolved in anhydrous THF/1-methyl-2-pyrrolidinone (NMP) (60 ml/5.5 ml). Fe(acac)₃ (177 mg, 5% mol) is added at room temperature. C₂H₅MgBr (3.0 M in ether, 4.0 ml) was added dropwise at room temperature and stirred for 20 minutes. Another 2.0 ml of C₂H₅MgBr (3.0 M in ether) is added at room temperature. The reaction mixture is quenched with water (100 ml) and extracted with ethyl acetate (100 ml 3 extractions). The combined organic layers are washed with brine (100 ml) and dried with anhydrous sodium acetate. Purification by flash column with 10% ethyl acetate in hexanes gives product (82) as a slightly yellow liquid. ¹HNMR (δ ppm, CDCl₃): 7.92(d, J=0.9 Hz, 1H), 6.88(s, 1H), 4.14(1H, m, —CHEt₂), 2.80(q, J=7.8 Hz, —CH₂CH₃), 2.60(q, J=7.8 Hz, —CH₂CH₃), 1.65–1.74(m, 4H, 2X(—CH₂CH₃)), 1.24(t, J=7.8 Hz, 6H, 2X(—CH₂CH₃)), 0.98(t, J=7.2H, 2X(—CH₂CH₃))

Step 5. Preparation of 2-Bromo-3,6-diethyl-5-(1-ethyl-propoxy)-pyridine

A solution of 2-(dimethylamino)ethanol (2.13 ml, 0.021 mol) in anhydrous hexanes (20 ml) is treated with n-BuLi (26.5 ml, 1.6M in hexanes) at 0° C. and stirred at 0° C. for 40 minutes. 3,6-Diethyl-5-(1-ethyl-propoxy)-pyridine (2.35 g, 0.01 mol) is added and stirred at 0° C. for 1.5 hours. The resulting reaction mixture is cooled to −78° C. Carbon tetrabromide (8.80 g, 0.027 mol) is added as a solution in hexanes (50 ml). The resulting mixture is stirred at −78° C. for 1 hour and 0° C. for 1 hour. The reaction is quenched with water (80 ml) and extracted with ethyl acetate (100 ml) and dichloromethane (60 ml, 2 extractions). The combined organic layers are washed with brine (150 mlX1) and dried with anhydrous sodium sulfate. Purification by column chromatography with hexanes/ethyl acetate (1/20) gave product (83) as a brown liquid. $^1$HNMR (δ ppm, $CDCl_3$) 6.91(s, 1H), 4.10(1H, m, —CHEt$_2$), 2.76(q, J=7.6H, —CH$_2$CH$_3$), 2.66(q, J=7.6 Hz, —CH$_2$CH$_3$), 1.64–1.71(m, 4H, 2X(—CH$_2$CH$_3$)), 1.15–1.26(m, 2X(—CH$_2$CH$_3$)), 0.92–1.01(m, 2X(—CH$_2$CH$_3$))

Step 6. Preparation of 2,5-Diethyl-3-(1-ethyl-propoxy)-6-(2-methoxy-4-trifluoromethoxy-phenyl)-pyridine 2-Bromo-3,6-diethyl-5-(1-ethyl-propoxy)-pyridine (83) (90 mg, 0.3 mmol) is dissolved in toluene (3 ml) followed by the addition of Tetrakis(triphenylphosphine)palladium (O) (Pd(PPh$_3$)$_4$)(34 mg), 4-trifluoromethoxy-2-methoxy-phenylboronic acid (120 mg, 0.5 mmol) and aqueous sodium carbonate (0.6 ml, 1.0M in water). The resulting mixture is heated at 90° C. for 15 hours. The reaction mixture is cooled to room temperature and diluted with water (20 ml), extracted with ethyl acetate (15 ml, 3 extractions). The combined organic layers are washed with brine and dried with anhydrous sodium sulfate. Purification by column chromatography, eluting with 4% ethyl acetate in hexanes provides the product (84). $^1$HNMR δ(ppm, $CDCl_3$) 7.25(d, J=8.4 Hz, 1H, phenyl-H), 6.97(s, 1H, pyridyl-H), 6.89(d, J=7.6 Hz, 1H, phenyl-H), 6.78(s, 1H, phenyl-H), 4.19(1H, m, —CHEt$_2$), 3.76(s, 3H, —OCH$_3$), 2.85(br, —CH$_2$CH$_3$), 2.39(br, —CH$_2$CH$_3$), 1.72–1.78(m, 4H, 2X(—CH$_2$CH$_3$) on pentyl group), 1.23(t, J=7.2 Hz, 3H, —CH$_2$CH$_3$), 1.07(t, J=7.2 Hz, 3H, —CH$_2$CH$_3$), 1.00(t, J=7.2 Hz, 6H, 2X(—CH$_2$CH$_3$) on pentyl group) LC-MC data [M+1]$^+$ 412.25, RT 2.75 min.

Example 6

Preparation of Diethyl-[2-ethyl-6-(2-methoxy-4-trifluoromethoxy-phenyl)-5-methyl-pyridin-3-yl]-amine Step 1. Preparation of 2-Ethyl-6-(2-methoxy-4-trifluoromethoxy-phenyl)-5-methyl-3-nitro-pyridine (85)

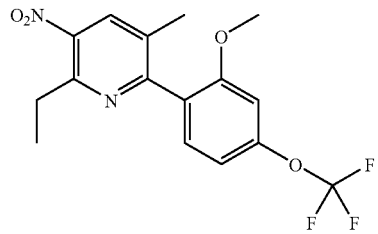

Tetrakistriphenylphosphinepalladium(0) (0.03 g, 0.03 mmol) is added to 2-chloro-6-(2-methoxy-4-trifluoromethoxy-phenyl)-5-methyl-3-nitro-pyridine (0.10 g, 0.27 mmol) in toluene (5 mL). Ethyl boronic acid (0.1 g, 1.1 mmol) and potassium carbonate (0.07 g, 0.55 mmol)) are added to this solution, and the reaction is heated to reflux for 17 hours. The product is extracted with ethyl acetate (20 mL). Combined extracts are washed with brine (20 mL), dried over sodium sulfate, and concentrated in vacuo. Purification by flash column chromatography (5% EtOAC-hexane) yields 2-ethyl-6-(2-methoxy-4-trifluoromethoxy-phenyl)-5-methyl-3-nitro-pyridine as a yellow solid TLC R$_f$ 0.55 (elution with 10% ethyl acetate-hexane)

Step 2. Preparation of 2-Ethyl-6-(2-methoxy-4-trifluoromethoxy-phenyl)-5-methyl-pyridin-3-yl-amine (86)

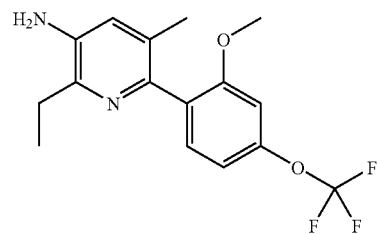

10% Pd/C (0.1 g) is added to a solution of 2-ethyl-6-(2-methoxy-4-trifluoromethoxy-phenyl)-5-methyl-3-nitro-pyridine (0.3 g, 0.84 mmol) in ethanol (10 mL). The mixture is hydrogenated at a pressure of 50 psi for 4 hours. The mixture is filtered through celite and evaporated to dryness under reduced pressure to give 2-ethyl-6-(2-methoxy-4-trifluoromethoxy-phenyl)-5-methyl-pyridin-3-ylamine as a yellow solid which is used without further purification TLC R$_f$ 0.30 (elution with 5% methanol-methylene chloride).

Step 3. Preparation of 2-Ethyl-6-(2-methoxy-4-trifluoromethoxy-phenyl)-5-methyl-3-nitro-pyridine (87)

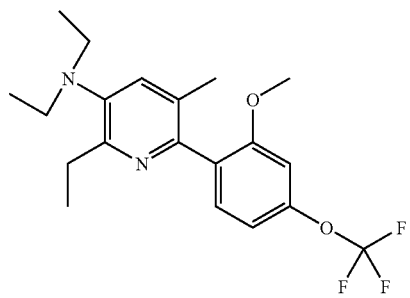

A solution of 2-ethyl-6-(2-methoxy-4-trifluoromethoxy-phenyl)-5-methyl-pyridin-3-yl amine (0.07 g, 0.21 mmol), 3-pentanone (0.02 mL, 0.21 mmol) and acetic acid (0.01 mL, 0.21 mmol) in dry dichloroethane (3 mL) is treated with sodium triacetoxyborohydride (0.06 g, 0.30 mmol) and stirred at room temperature overnight. The resulting mixture is diluted with $CH_2Cl_2$ (20 mL) and washed with saturated aqueous NaCl (50 mL). The organic portion is dried over $Na_2SO_4$, filtered and concentrated under reduced pressure. Purification by preparative TLC (5% methanol-$CH_2Cl_2$) gives Diethyl-[2-ethyl-6-(2-methoxy-4-trifluoromethoxy-phenyl)-5-methyl-pyridin-3-yl]-amine (87) as a yellow solid TLC R$_f$ 0.45 (elution with 5% methanol-methylene chloride)

Example 6A

Preparation of 2-ethyl-6-[2-methoxy-4-(trifluoromethoxy)phenyl]-5-methyl-N,N-dipropylpyridin-3-amine (88)

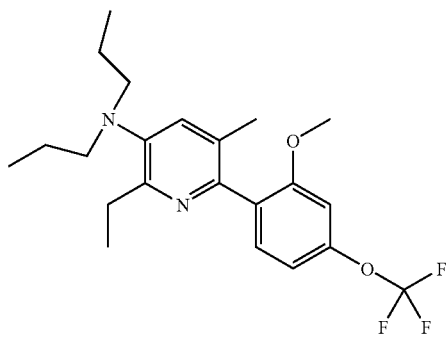

2-ethyl-6-[2-methoxy-4-(trifluoromethoxy)phenyl]-5-methyl-N,N-dipropylpyridin-3-amine (88) is prepared by a method analogous to that given in Example 6. TLC R$_f$ 0.4 (elution with 5% methanol-methylene chloride).

Example 6B

Preparation of 2-Ethyl-6-(2-methoxy-4trifluoromethoxy-phenyl)-5-methyl-pyridin-3-yl]-propyl-amine (89)

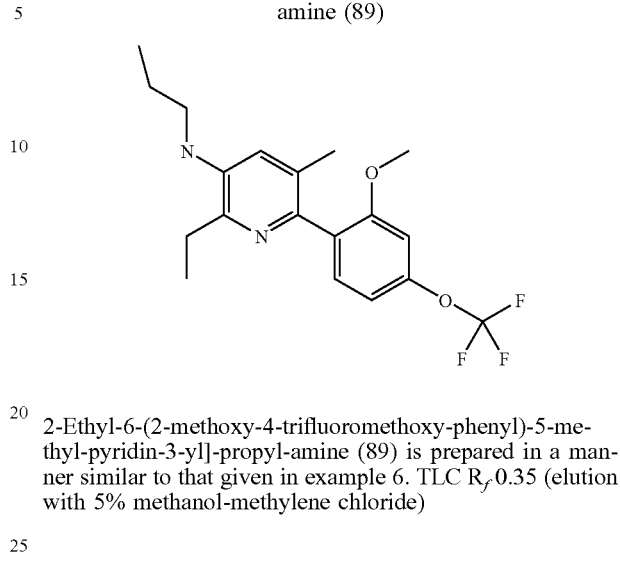

2-Ethyl-6-(2-methoxy-4-trifluoromethoxy-phenyl)-5-methyl-pyridin-3-yl]-propyl-amine (89) is prepared in a manner similar to that given in example 6. TLC R$_f$ 0.35 (elution with 5% methanol-methylene chloride)

Example 7

Preparation of [2-methoxy-6-(2-methoxy-4-trifluoromethoxy-phenyl)-5-methyl-pyridin-3-yl]-dipropyl-amine and [2-methoxy-6-(2-methoxy-4-trifluoromethoxy-phenyl)-5-methyl-pyridin-3-yl]-propyl-amine

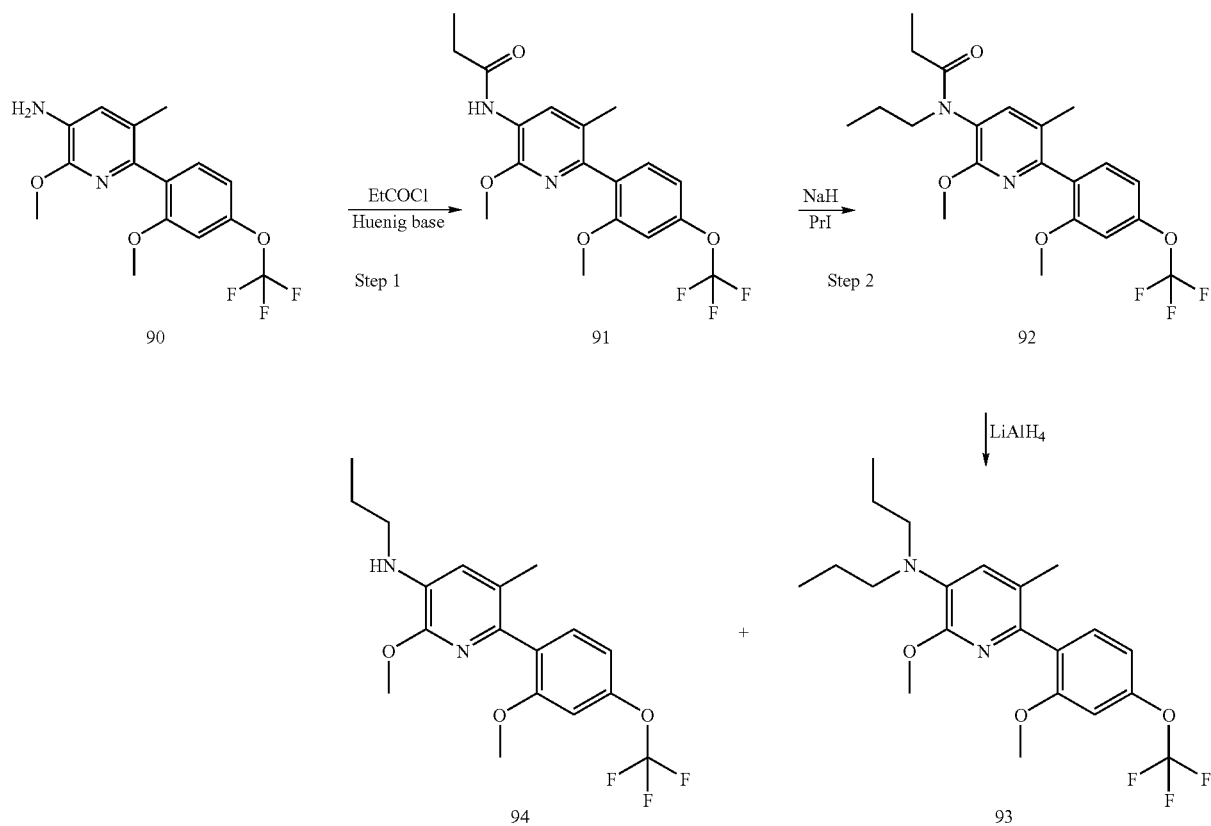

Step 1. Preparation of N-[2-methoxy-6-(2-methoxy-4-trifluoromethoxy-phenyl)-5-methyl-pyridin-3-yl]-propionamide (91).

Propionyl chloride (0.058 ml, 0.67 mmol) is added to a solution of 2-methoxy-6-(2-methoxy-4-trifluoromethoxy-phenyl)-5-methyl-pyridin-3-ylamine (0.2 g, 0.61 mmol) and diisopropylethylamine (0.13 ml, 0.73 mmol) in CH$_2$Cl$_2$ (1.5 ml) at room temperature. The mixture is kept at room temperature for 3 hours, and is then diluted with EtOAc The mixture is washed with 1N NaOH and brine. After drying over Na$_2$SO$_4$, the solvent is removed under reduced pressure and the residue is purified by flash column chromatography (hexane/EtOAc=4:1) to give the N-[2-methoxy-6-(2-methoxy-4-trifluoromethoxy-phenyl)-5-methyl-pyridin-3-yl]-propionamide. Rf (hexane/EtOAc=4:1)=0.2.

Step 2. Preparation of N-[2-methoxy-6-(2-methoxy-4-trifluoromethoxy-phenyl)-5-methyl-pyridin-3-yl]-N-propyl-propionamide (92)

60% NaH (23 mg, 0.58 mmol) is added to a solution of N-[2-methoxy-6-(2-methoxy-4-trifluoromethoxy-phenyl)-5-methyl-pyridin-3-yl]-propionamide (0.15 g, 0.39 mmol) in DMF (1 ml) at room temperature. After stirring at room temperature for 20 minutes, iodo propane (0.058 ml, 0.58 mmol) is added. The mixture is stirred at room temperature for 3 days. 20 ml of water is added and the mixture is extracted with EtOAc. The combined extracts are washed with brine and dried over Na$_2$SO$_4$. The solvent is removed under reduced pressure and the residue is purified by flash column chromatography to give N-[2-methoxy-6-(2-methoxy-4-trifluoromethoxy-phenyl)-5-methyl-pyridin-3-yl]-N-propyl-propionamide. Rf (hexane/EtOAc=2:1)=0.42.

Step 3. Preparation of [2-Methoxy-6-(2-methoxy-4-trifluoromethoxy-phenyl)-5-methyl-pyridin-3-yl]-dipropyl-amine (93) and [2-Methoxy-6-(2-methoxy-4-trifluoromethoxy-phenyl)-5-methyl-pyridin-3-yl]-propyl-amine (94)

A 1M solution of LiAlH$_4$ in THF (0.52 ml, 0.52 mmol) at 0° C. is added to a solution of N-[2-methoxy-6-(2-methoxy-4-trifluoromethoxy-phenyl)-5-methyl-pyridin-3-yl]-N-propyl-propionamide (94) (0.11 g, 0.26 mmol) in THF (1 ml). The mixture is stirred at 0° C. for 30 minutes and at room temperature for 15 hours. The reaction is quenched by ether containing water (5 ml) at 0° C. Water (1 ml) and EtOAc (20 ml) are added to the mixture and the suspension is stirred at room temperature for 20 minutes. MgSO$_4$ (2 g) and Celite (2 g) are added and the mixture is stirred at room temperature for 40 minutes. The inorganic salts are removed and washed with EtOAc. The combined filtrates are concentrated under reduced pressure and the residue is purified by flash column chromatography to give [2-methoxy-6-(2-methoxy-4-trifluoromethoxy-phenyl)-5-methyl-pyridin-3-yl]-dipropyl-amine (93); Rf (hexane/EtOAc=9:1)=0.39, MS m/z 413.4 (M+H) and [2-methoxy-6-(2-methoxy-4-trifluoromethoxy-phenyl)-5-methyl-pyridin-3-yl]-propyl-amine; Rf (hexane/EtOAc=9:1)=0.35, MS m/z 371.3 (M+H) (94)

Example 8

Additional 3-Alkoxy Compounds of Formula I

The following compounds were prepared using the methods shown in above Schemes I and II and further illustrated by Examples 1 and 2.

TABLE I

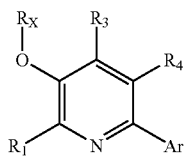

| Cpd. # | R$_X$ | R$_1$ | R$_3$ | R$_4$ | Ar | Name | Analytical Data MS (M + 1) or NMR (ppm) |
|---|---|---|---|---|---|---|---|
| 100 | 1-ethyl-propyl | H | H | methyl | 2,4-dichloro-phenyl | 2-(2,4-Dichloro-phenyl)-5-(1-ethyl-propoxy)-3-methyl-pyridine | 0.98(t, 6H), 1.75(m, 4H), 2.15(s, 3H), 4.20(m, 1H), 7.05 (s, 1H), 7.22(d, 1H), 7.35(d, 1H), 7.43(s, 1H), 8.20(s, 1H) |
| 101 | 1-ethyl-propyl | Cl | H | methyl | 2,4-dichloro-phenyl | 2-(2,4-Dichloro-phenyl)-5-(1-ethyl-propoxy)-3-methyl-6-chloro-pyridine | 1.02(t, 6H), 1.78(m, 4H), 2.15(s, 3H), 4.22(m, 1H), 7.05 (s, 1H), 7.22(d, 1H), 7.30(d, 1H), 7.44(s, 1H) |
| 102 | 1-ethyl-propyl | H | Cl | methyl | 2,4-dichloro-phenyl | 2-(2,4-Dichloro-phenyl)-5-(1-ethyl-propoxy)-3-methyl-4-chloro-pyridine | 1.02(t, 6H), 1.80(m, 4H), 2.18(s, 3H), 4.30(m, 1H), 7.22 (d, 1H), 7.34(d, 1H), 7.48(s, 1H), 8.20(s, 1H) |
| 103 | 1-ethyl-propyl | H | H | methyl | 2-methoxy-4-trifluoromethoxy-phenyl | 2-(2-methoxy-4-trifluoromethoxy-phenyl)-5-(1-ethyl-propoxy)-3-methyl-pyridine | 370.2 (M + 1) |
| 104 | 1-ethyl-propyl | Cl | H | methyl | 2-methoxy-4-trifluoromethoxy-phenyl | 2-(2-methoxy-4-trifluoromethoxy-phenyl)-5-(1-ethyl-propoxy)-3-methyl-6-chloro-pyridine | 1.02(t, 6H), 1.78(m, 4H), 2.16(s, 3H), 3.78(s, 3H), 4.20 (m, 1H), 6.78(s, 1H), 6.90(d, 1H), 7.02(s, 1H), 7.22(d, 1H). |
| 105 | 1-ethyl-propyl | methoxy | H | methyl | 2-methoxy-4-trifluoromethoxy-phenyl | 2-(2-methoxy-4-trifluoromethoxy-phenyl)-5-(1-ethyl-propoxy)-3-methoxy-6-methyl-pyridine | 400.39 (M + 1) |

TABLE I-continued

| Cpd. # | R$_X$ | R$_1$ | R$_3$ | R$_4$ | Ar | Name | Analytical Data MS (M + 1) or NMR (ppm) |
|---|---|---|---|---|---|---|---|
| 106 | 1-ethyl-propyl | ethyl | H | methyl | 2-methoxy-4-trifluoromethoxy-phenyl | 2-(2-methoxy-4-trifluoromethoxy-phenyl)-5-(1-ethyl-propoxy)-3-6-ethyl-pyridine | 0.98(t, 6H), 1.22(t, 3H), 1.75 (m, 4H), 2.06(s, 3H), 2.82(q, 2H), 3.78(s, 3H), 4.18 (m, 1H), 6.78(d, 1H), 6.90 (dd, 1H), 6.92(s, 1H), 7.22(d, 1H) |
| 107 | 1-ethyl-propyl | CH$_3$NH | H | methyl | 4-isopropyl-6-methoxy-2-pyridyl | [3-Methyl-5-(1-ethyl-propoxy)-5'-isopropyl-3'-methoxy-[2,2']bipyridinyl-6-yl]-methyl-amine | |
| 108 | 1-ethyl-propyl | CH$_3$NH | H | ethyl | 4-isopropyl-6-methoxy-2-pyridyl | [3-Ethyl-5-(1-ethyl-propoxy)-5'-isopropyl-3'-methoxy-[2,2']bipyridinyl-6-yl]-methyl-amine | |
| 109 | 1-ethyl-propyl | CH$_3$O | H | methyl | 4-isopropyl-6-methoxy-2-pyridyl | 3-Methyl-5-(1-ethyl-propoxy)-5'-isopropyl-6,3'-dimethoxy-[2,2']bipyridinyl | |
| 110 | 1-ethyl-propyl | CH$_3$O | H | ethyl | 4-isopropyl-6-methoxy-2-pyridyl | 3-Ethyl-5-(1-ethyl-propoxy)-5'-isopropyl-6,3'-dimethoxy-[2,2']bipyridinyl | |
| 111 | 1-ethyl-propyl | CH$_3$NH | H | methyl | 2-ethyl-4-isopropyl-5-methoxy-3-pyridyl | [2-Ethyl-5-(1-ethyl-propoxy)-6'-isopropyl-5'-methoxy-3-methyl-[2,3']bipyridinyl-6-yl]-methyl-amine | |
| 112 | 1-ethyl-propyl | CH$_3$NH | H | ethyl | 2-ethyl-4-isopropyl-5-methoxy-3-pyridyl | [3,2'-Diethyl-5-(1-ethyl-propoxy)-6'-isopropyl-5'-methoxy-3-methyl-yl]-methyl-amine | |
| 113 | 1-ethyl-propyl | ethyl | H | methyl | 2-ethyl-4-isopropyl-5-methoxy-3-pyridyl | 6,2'-Diethyl-5-(1-ethyl-propoxy)-6'-isopropyl-5'-methoxy-3-methyl-[2,3']bipyridinyl | |
| 114 | 1-ethyl-propyl | ethyl | H | ethyl | 2-ethyl-4-isopropyl-5-methoxy-3-pyridyl | 3,6,2'-Triethyl-5-(1-ethyl-propoxy)-6'-isopropyl-5'-methoxy-[2,3']bipyridinyl | |
| 115 | 1-ethyl-propyl | CH$_3$NH | H | methyl | 2-methyl-4-isopropylamino-5-methoxy-3-pyridyl | 5-(1-Ethyl-propoxy)-N6'-isopropyl-5'-methoxy-3,2',N6-trimethyl [2,3']bipyridinyl-6,6'-diamine | |
| 116 | 1-ethyl-propyl | CH$_3$NH | H | ethyl | 2-methyl-4-isopropylamino-5-methoxy-3-pyridyl | 3-Ethyl-5-(1-ethyl-propoxy)-N6'-isopropyl-5'-methoxy-2',N6-dimethyl-[2,3']bipyridinyl-6,6'-diamine | |
| 117 | 1-ethyl-propyl | ethyl | H | methyl | 2-methyl-4-isopropylamino-5-methoxy-3-pyridyl | [6-Ethyl-5-(1-ethyl-propoxy)-5'-methoxy-3,2'-dimethyl-[2,3']bipyridinyl-6'-yl]-isopropyl-amine | |
| 118 | 1-ethyl-propyl | ethyl | H | ethyl | 2-methyl-4-isopropylamino-5-methoxy-3-pyridyl | [3,6-Diethyl-5-(1-ethyl-propoxy)-5'-methoxy-2'-methyl-[2,3']bipyridinyl-6'-yl]-isopropyl-amine | |
| 119 | 1-ethyl-propyl | CH$_3$NH | H | methyl | 2,4,6-trimethyl-5-(4-methyl-oxazol-2-yl) | [3-Methyl-5-(1-ethyl-propoxy)-2',4',6'-trimethyl-5'-(4-methyl-oxazol-2-yl)-[2,3']bipyridinyl-6-yl]-methyl-amine | |
| 120 | 1-ethyl-propyl | CH$_3$NH | H | ethyl | 2,4,6-trimethyl-5-(4-methyl-oxazol-2-yl) | [3-Ethyl-5-(1-ethyl-propoxy)-2',4',6'-trimethyl-5'-(4-methyl-oxazol-2-yl)-[2,3']bipyridinyl-6-yl]-methyl-amine | |
| 121 | 1-ethyl-propyl | Ethyl | H | methyl | 2,4,6-trimethyl-5-(4-methyl-oxazol-2-yl) | 3-Methyl-6-ethyl-5-(1-ethyl-propoxy)-2',3',6'-trimethyl-5'-(4-methyl-oxazol-2-yl)-[2,3']bipyridinyl | |

TABLE I-continued

| Cpd. # | Rx | R1 | R3 | R4 | Ar | Name | Analytical Data MS (M + 1) or NMR (ppm) |
|---|---|---|---|---|---|---|---|
| 122 | 1-ethyl-propyl | Ethyl | H | ethyl | 2,4,6-trimethyl-5-(4-methyl-oxazol-2-yl) | 3,6-Dimethyl-5-(1-ethyl-propoxy)-2',4',6'-trimethyl-5'-(4-methyl-oxazol-2-yl)-[2,3']bipyridinyl | |
| 123 | 1-ethyl-propyl | $CH_3NH$ | H | methyl | 4-isopropoxy-6-methoxy-3-pyridiyl | [3-Methyl-5-(1-ethyl-propoxy)-6'-isopropoxy-4'-methoxy-[2,3']bipyridinyl-6-yl]-methyl-amine | |
| 124 | 1-ethyl-propyl | $CH_3NH$ | H | ethyl | 4-isopropoxy-6-methoxy-3-pyridiyl | [3-Ethyl-5-(1-ethyl-propoxy)-6'-isopropoxy-4'-methoxy-[2,3']bipyridinyl-6-yl]-methyl-amine | |
| 125 | 1-ethyl-propyl | Ethyl | H | methyl | 4-isopropoxy-6-methoxy-3-pyridyl | 3-Methyl-6-ethyl-5-(1-ethyl-propoxy)-6'-isopropoxy-4'-methoxy-[2,3']bipyridinyl | |
| 126 | 1-ethyl-propyl | Ethyl | H | ethyl | 4-isopropoxy-6-methoxy-3-pyridyl | 3,6-Diethyl-5-(1-ethyl-propoxy)-6'-isopropoxy-4'-methoxy-[2,3']bipyridinyl | |

The compounds shown in Table II were prepared using the methods in above Schemes I, II, IV, and V and further illustrated by Examples 1, 2, 4, and 5.

TABLE II

| Cmp # | R1 | R3 | R4 | R5 | R6 | A | IUPAC Name | Analytical Data MS (M + 1) |
|---|---|---|---|---|---|---|---|---|
| 127 | $CH_3NH$ | H | $CH_3$ | $CH_3O$ | $CF_3O$ | CH | 3-(1-ethylpropoxy)-6-[2-methoxy-4-(trifluoromethoxy)phenyl]-N,5-dimethylpyridin-2-amine | 399.4 |
| 128 | $CH_3NH$ | H | $CH_3CH_2$ | $CH_3O$ | $CF_3O$ | CH | 5-ethyl-3-(1-ethylpropoxy)-6-[2-methoxy-4-(trifluoromethoxy)phenyl]-N-methylpyridin-2-amine | 413.4 |
| 129 | $CH_3NH$ | H | Br | $CH_3O$ | $CF_3O$ | CH | 5-bromo-3-(1-ethylpropoxy)-6-[2-methoxy-4-(trifluoromethoxy)phenyl]-N-methylpyridin-2-amine | 463.3, 465.3 |
| 130 | $CH_3NH$ | H | $CH_3CH_2$ | Cl | $CH_3O$ | CH | 6-(2-chloro-4-methoxyphenyl)-5-ethyl-3-(1-ethylpropoxy)-N-methylpyridin-2-amine | 363.3, 365.3 |
| 131 | $CH_3NH$ | H | $CH_3$ | Cl | $CH_3O$ | CH | 6-(2-chloro-4-methoxyphenyl)-3-(1-ethylpropoxy)-N,5-dimethylpyridin-2-amine | 349.4, 351.4 |
| 132 | $CH_3NH$ | H | Br | $CH_3O$ | $(CH_3)_2CHO$ | CH | 5-bromo-3-(1-ethylpropoxy)-6-(4-isopropoxy-2-methoxyphenyl)-N-methylpyridin-2-amine | 437.3, 439.3 |

TABLE II-continued

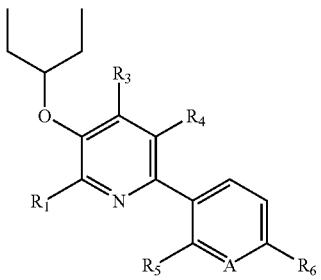

| Cmp # | $R_1$ | $R_3$ | $R_4$ | $R_5$ | $R_6$ | A | IUPAC Name | Analytical Data MS (M + 1) |
|---|---|---|---|---|---|---|---|---|
| 133 | $CH_3NH$ | H | $CH_3$ | Cl | $(CH_3)_2CHO$ | CH | 6-(2-chloro-4-isopropoxyphenyl)-3-(1-ethylpropoxy)-N,5-dimethylpyridin-2-amine | 377.4, 379.4 |
| 134 | $CH_3NH$ | H | Br | Cl | $(CH_3)_2CHO$ | CH | 5-bromo-6-(2-chloro-4-isopropoxyphenyl)-3-(1-ethylpropoxy)-N-methylpyridin-2-amine | 441.2, 443.2, 445.2 |
| 135 | $CH_3NH$ | H | Cl | $CH_3O$ | $CHF_2O$ | CH | 5-chloro-6-[4-(difluoromethoxy)-2-methoxyphenyl]-3-(1-ethylpropoxy)-N-methylpyridin-2-amine | 401.4, 403.4 |
| 136 | $CH_3NH$ | H | Br | $CH_3O$ | $CHF_2O$ | CH | 5-bromo-6-[4-(difluoromethoxy)-2-methoxyphenyl]-3-(1-ethylpropoxy)-N-methylpyridin-2-amine | 445.2, 447.2 |
| 137 | $CH_3NH$ | H | $CH_3$ | $CH_3O$ | $(CH_3)_2CHO$ | CH | 3-(1-ethylpropoxy)-6-(4-isopropoxy-2-methoxyphenyl)-N,5-dimethylpyridin-2-amine | 373.4 |
| 138 | $CH_3NH$ | H | $CH_3CH_2$ | $CH_3O$ | $CHF_2O$ | CH | 6-[4-difluoromethoxy)-2-methoxyphenyl]-5-ethyl-3-(1-ethylpropoxy)-N-methylpyridin-2-amine | 395.5 |
| 139 | $CH_3NH$ | H | $CH_3$ | $CH_3O$ | $(CH_3)_2CH$ | CH | 3-(1-ethylpropoxy)-6-(4-isopropyl-2-methoxyphenyl)-N,5-dimethylpyridin-2-amine | 357.5 |
| 140 | $CH_3NH$ | H | $CH_3CH_2$ | $CH_3O$ | $(CH_3)_2CH$ | CH | 5-ethyl-3-(1-ethylpropoxy)-6-(4-isopropyl-2-methoxyphenyl)-N-methylpyridin-2-amine | 371.4 |
| 141 | $CH_3NH$ | H | Br | $CH_3O$ | $(CH_3)_2CH$ | CH | 5-bromo-3-(1-ethylpropoxy)-6-(4-isopropyl-2-methoxyphenyl)-N-methylpyridin-2-amine | 421.4, 423.4 |
| 142 | $CH_3NH$ | H | Br | Cl | $CH_3O$ | CH | 5-bromo-6-(2-chloro-4-methoxyphenyl)-3-(1-ethylpropoxy)-N-methylpyridin-2-amine | 413.2, 415.2, 417.2 |
| 143 | $CH_3NH$ | H | H | Cl | $CH_3O$ | CH | 6-(2-chloro-4-methoxyphenyl)-3-(1-ethylpropoxy)-N-methylpyridin-2-amine | 335.2, 337.2 |
| 144 | $CH_3NH$ | H | Br | $CF_3O$ | $CH_3O$ | CH | 5-bromo-3-(1-ethylpropoxy)-6-[4-methoxy-2-(trifluoromethoxy)phenyl]-N-methylpyridin-2-amine | 463.1, 465.1 |
| 145 | $CH_3NH$ | H | H | $CF_3O$ | $CH_3O$ | CH | 3-(1-ethylpropoxy)-6-[4-methoxy-2-(trifluoromethoxy)phenyl]-N-methylpyridin-2-amine | 385.2 |
| 146 | $CH_3NH$ | H | $CH_3CH_2$ | $CF_3O$ | $CH_3O$ | CH | 5-ethyl-3-(1-ethylpropoxy)-6-[4-methoxy-2-(trifluoromethoxy)phenyl]-N-methylpyridin-2-amine | 413.3 |
| 147 | $CH_3NH$ | H | $CH_3$ | $CF_3O$ | $CH_3O$ | CH | 3-(1-ethylpropoxy)-6-[4-methoxy-2-(trifluoromethoxy)phenyl]-N,5-dimethylpyridin-2-amine | 399.3 |
| 148 | $CH_3NH$ | H | $CH_3$ | $CH_3O$ | $CF_3$ | CH | 3-(1-ethylpropoxy)-6-[2-methoxy-4-(trifluoromethyl)phenyl]-N,5-dimethylpyridin-2-amine | 383.3 |
| 149 | H | Cl | $CH_3$ | $CH_3O$ | $CF_3$ | CH | 4-chloro-5-(1-ethylpropoxy)-2-[2-methoxy-4-(trifluoromethyl)phenyl]-3-methylpyridine | 388.2, 390.2 |
| 150 | Cl | H | $CH_3$ | $CH_3O$ | $CF_3$ | CH | 2-chloro-3-(1-ethylpropoxy)-6-[2-methoxy-4-(trifluoromethyl)phenyl]-5-methylpyridine | 388.2, 390.2 |
| 151 | H | H | $CH_3$ | $CH_3O$ | $CF_3$ | CH | 5-(1-ethylpropoxy)-2-[2-methoxy-4-(trifluoromethyl)phenyl]-3-methylpyridine | 354.2 |
| 152 | $CH_3CH_2$ | H | $CH_3CH_2$ | $CF_3O$ | $CH_3O$ | CH | '2,5-diethyl-3-(1-ethylpropoxy)-6-[4-methoxy-2-(trifluoromethoxy)phenyl]pyridine | 412.25 |
| 153 | $CH_3CH_2$ | H | $CH_3CH_2$ | $CH_2O$ | $(CH_3)_2CHO$ | CH | 2,5-diethyl-3-(1-ethylpropoxy)-6-(4-isopropoxy-2-methoxyphenyl)pyridine | 386.30 |

TABLE II-continued

| Cmp # | R₁ | R₃ | R₄ | R₅ | R₆ | A | IUPAC Name | Analytical Data MS (M + 1) |
|---|---|---|---|---|---|---|---|---|
| 154 | CH₃CH₂ | H | CH₃CH₂ | CH₃O | CH₃CH₂O | CH | 2-(4-ethoxy-2-methoxyphenyl)-3,6-diethyl-5-(1-ethylpropoxy)pyridine | 372.27 |
| 155 | CH₃CH₂ | H | CH₃CH₂ | CH₃O | (CH₃)₂CH | CH | 2,5-diethyl-3-(1-ethylpropoxy)-6-(4-isopropyl-2-methoxyphenyl)pyridine | 370.33 |
| 156 | CH₃CH₂ | H | CH₃CH₂ | CH₃O | CHF₂O | CH | 2-[4-(difluromethoxy)-2-methoxyphenyl]-3,6-diethyl-5-(1-ethylpropoxy)pyridine | 394.25 |
| 157 | CH₃CH₂ | H | CH₃CH₂ | CH₃O | CF₃O | CH | 2,5-diethyl-3-(1-ethylpropoxy)-6-[2-methoxy-4-(trifluromethoxy)phenyl]pyridine | 412.25 |
| 158 | CH₃CH₂ | H | CH₃CH₂ | CH₃CH₂ | (CH₃)₂CHNH | N | 2',3,6-triethyl-5-(1-ethylpropoxy)-N-isopropyl-2,3'-bipyridin-6'-amine | 384.27 |
| 159 | CH₃NH | H | CH₃ | CH₃O | (CH₃)₂CH | N | 5-(1-ethylpropoxy)-6'-isopropyl-2'-methoxy-N,3-dimethyl-2,3'-bipyridin-6-amine | 358.4 |
| 160 | CH₃NH | H | CH₃CH₂ | CH₃O | (CH₃)₂CH | N | 3-ethyl-5-(1-ethylpropoxy)-6'-isopropyl-2'-methoxy-N-methyl-2,3'-bipyridin-6-amine | 372.5 |
| 161 | CH₃CH₂ | H | CH₃CH₂ | CH₃O | (CH₃)₂CH | N | 3,6-diethyl-5-(1-ethylpropoxy)-6'-isopropyl-2'-methoxy-2,3'-bipyridine | 371.33 |
| 162 | CH₃NH | H | Br | CH₃O | (CH₃)₂CH | N | 3-bromo-5-(1-ethylpropoxy)-6'-isopropyl-2'-methoxy-N-methyl-2,3'-bipyridin-6-amine | 422.3, 424.3 |
| 163 | CH₃NH | H | H | CH₃O | (CH₃)₂CH | N | 5-(1-ethylpropoxy)-6'-isopropyl-2'-methoxy-N-methyl-2,3'-bipyridin-6-amine | 344.3 |
| 164 | CH₃NH | H | CH₃CH₂ | CH₃CH₂O | (CH₃)₂CH | N | 2'-ethoxy-3-ethyl-5-(1-ethylpropoxy)-6'-isopropyl-N-methyl-2,3'-bipyridin-6-amine | 386.3 |
| 165 | (CH₃CH₂)(CH₃)N— | H | CH₃CH₂ | CH₃O | (CH₃)₂CH | N | 2'-ethoxy-N,3-diethyl-5-(1-ethylpropoxy)-6'-isopropyl-N-methyl-2,3'-bipyridin-6-amine | 414.4 |
| 166 | CH₃NH | H | Cl | CH₃O | (CH₃)₂CH | N | 3-chloro-5-(1-ethylpropoxy)-6'-isopropyl-2'-methoxy-N-methyl-2,3'-bipyridin-6-amine | 378.3, 380.3 |
| 167 | CH₃NH | H | CH₃CH₂ | CH₃CH₂ | (CH₃)₂CH | N | 2',3-diethyl-5-(1-ethylpropoxy)-6'-isopropyl-N-methyl-2,3'-bipyridin-6-amine | 370.4 |
| 168 | CH₃NH | H | CH₃CH₂ | CH₃CH₂O | (CH₃)₂CH | N | [2'-Ethoxy-3-ethyl-5-(1-ethyl-propoxy)-6'-isopropyl-[2,3']bipyridinyl-6-yl]-methyl-amine | |
| 169 | CH₃NH | H | CH₃CH₂ | CH₃ | (CH₃)₂CH | N | [2'-Methyl-3-ethyl-5-(1-ethyl-propoxy)-6'-isopropyl-[2,3']bipyridinyl-6-yl]-methyl-amine | |
| 170 | CH₃NH | H | CH₃CH₂ | CH₃ | (CH₃)₂CH—O | N | [2'-Methyl-3-ethyl-5-(1-ethyl-propoxy)-6'-isopropoxy-[2,3']bipyridinyl-6-yl]-methyl-amine | |
| 171 | CH₃NH | H | CH₃CH₂ | CH₃ | (CH₃)₂N | N | 3-Ethyl-5-(1-ethyl-propoxy)-2',N6, N6', N6'-tetramethyl-[2,3']bipyridinyl-6,6'-diamine | |
| 172 | CH₃NH | H | CH₃ | HOCH₂ | (CH₃)₂CH | N | [2'-Hydroxymethyl-3-methyl-5-(1-ethyl-propoxy)-6'-isopropyl-[2,3'bipyridinyl-6-yl]-methyl-amine | |
| 173 | CH₃NH | H | CH₃CH₂ | HOCH₂ | (CH₃)₂CH | N | [2'-Hydroxymethyl-3-ethyl-5-(1-ethyl-propoxy)-6'-isopropyl-[2,3']bipyridinyl-6-yl]-methyl-amine | |
| 174 | CH₃O | H | CH₃CH₂ | HOCH₂ | (CH₃)₂CH | N | [5-(1-Ethyl-propoxy)-6'isopropyl-6-methoxy-3-methyl-[2,3']bipyridinyl-2'-yl]-methanol | |

TABLE II-continued

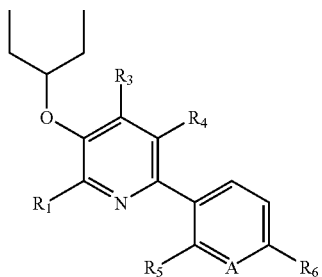

| Cmp # | R₁ | R₃ | R₄ | R₅ | R₆ | A | IUPAC Name | Analytical Data MS (M + 1) |
|---|---|---|---|---|---|---|---|---|
| 175 | CH₃O | H | CH₃CH₂ | HOCH₂ | (CH₃)₂CH | N | [5-(1-Ethyl-propoxy)-6'-isopropyl-6-methoxy-3-ethyl-[2,3']bipyridinyl-2'-yl]-methanol | |
| 176 | CH₃NH | H | CN | CH₃O | (CH₃)₂CH—O | CH | 5-(1-Ethyl-propoxy)-2-(4-isopropoxy-2-methoxy-phenyl)-6-methylamino-nicotinonitrile | |
| 177 | NH₂CH₂ | H | CH₃CH₂ | CH₃O | (CH₃)₂CH—O | CH | C-[5-Ethyl-3-(1-ethyl-propoxy)-6-(4-isopropoxy-2-methoxy-phenyl)-pyridin-2-yl]-methylamine | |
| 178 | CH₃NH | H | CH₃CH₂ | CH₃CH₂ | (CH₃)₂CH | N | [3,2'-Diethyl-5-(1-ethyl-propoxy)-6'-isopropyl-[2,3']bipyridinyl-6-yl]-methyl-amine | |
| 179 | CH₃CH₂ | H | CH₃CH₂ | CH₃O | CF₃ | N | 3,6-Diethyl-5-(1-ethyl-propoxy)-2'-methoxy-6'-trifluoromethyl-[2,3']bipyridinyl | |
| 180 | CH₃NH | H | CH₃CH₂ | CH₃ | (CH₃)₂CH | N | [3ethyl-2'-methyl-5-(1-ethyl-propoxy)-6'-isopropyl-[2,3']bipyridinyl-6-yl]-methyl-amine | |
| 181 | CH₃NH | H | CH₃CH₂ | (CH₃)₂CH—O | (CH₃)₂CH | N | [3-Ethyl-5-(1-ethyl-propoxy)-2'-isopropoxy-6'-isopropyl-[2,3']bipyridinyl-6-yl]-methyl-amine | |
| 182 | CH₃CH₂ | H | CH₃CH₂ | Cl | CH₃O | CH | 2-(2-Chloro-4-methoxy-phenyl)-3,6-diethyl-5-(1-ethyl-propoxy)-pyridine | |
| 183 | CH₃CH₂ | H | CH₃CH₂ | Cl | CH₃CH₂O | CH | 2-(2-Chloro-4-ethoxy-phenyl)-3,6-diethyl-5-(1-ethyl-propoxy)-pyridine | |
| 184 | CH₃NH | H | CH₃ | CH₃CH₂O | (CH₃)₂CH | N | [2'-Ethoxy-5-(1-ethyl-propoxy)-6'-isopropyl-3-methyl-[2,3']bipyridinyl-6-yl]-methyl-amine | |
| 185 | CH₃NH | H | CH₃ | CH₃CH₂ | (CH₃)₂CH | N | [2'-Ethyl-5-(1-ethyl-propoxy)-6'-isopropyl-3-methyl-[2,3']bipyridinyl-6-yl]-methyl-amine | |
| 186 | CH₃NH | H | CH₃CH₂ | Cl | (CH₃)₂CH | CH | 2-(2-Chloro-4-isopropoxy-phenyl)-3,6-diethyl-5-(1-ethyl-propoxy)-pyridine | |

Other alkoxy pyridinyl compounds of Formula I:

187. (2,4-dichlorophenyl)-5-(1-ethyl-propoxy)-3-methyl-pyridin-2-yl-1-N-oxide MS (M + 1): 340.1, 342.1, 344.1
188. (2-methoxy, 4-trifluoromethoxyphenyl)-5-(1-ethyl-propoxy)-3-methyl-pyridin-2-yl-1-N-oxide MS (M + 1) 340.1, 342.1, 344.1
189. 5-(1-ethylpropoxy)-2-[2-methoxy-4-(trifluoromethyl)phenyl]-3-methylpyridine 1-oxide MS 370.4
190. 3-Ethyl-5-(1-ethyl-propoxy)6,6'-diisopropyl-4'-methoxy-[2,3']bipyridinyl

Example 9

Additional 3-amino Compounds of Formula I

The following compounds were prepared using the methods shown in above Schemes III and further illustrated by Examples 3, 6 and 7.

TABLE III

| Cmp # | R$_X$ | R$_Y$ | R$_3$ | Ar | Name | Analytical Data MS (M + 1) or NMR (ppm) |
|---|---|---|---|---|---|---|
| 191 | propyl | propyl | chloro | 2-methoxy-4,6-dimethyl-phenyl | [5-Ethyl-6-(2-methoxy-4,6-dimethyl-phenyl)-2-methyl-4-chloro-pyridin-3-yl]-dipropyl amine | 389.3, 391.3 |
| 192 | propyl | cyclopropyl methyl | H | 2-methyl-4-methoxy-phenyl | Cyclopropylmethyl-[5-ethyl-6-(2-methyl-4-methoxy-phenyl)-2-methyl-pyridin-3-yl]-propyl-amine | MS 353 (M + H), NMR 7.30(s, 1H), 7.11(d, 1H), 6.80(s, 1H), 6.78(d, 1H), 3.83(s, 3H), 3.11(t, 2H), 2.83(d, 2H), 2.57(s, 3H), 2.37(q, 2H), 2.04(s, 3H), 1.48(m, 2H), 1.01(t, 3H), 0.90(t, 3H), 0.80(m, 1H), 0.42(m, 2H), 0.01(m, 2H). |
| 193 | propyl | isopropyl | H | 2-methyl-4-methoxy-phenyl | Isopropylmethyl-[5-ethyl-6-(2-methyl-4-methoxy-phenyl)-2-methyl-pyridin-3-yl]-propyl-amine | MS 355 (M + H), NMR 7.26(d, 1H), 7.11(d, 1H), 6.80(s, 1H), 6.78(d, 1H), 3.83(s, 3H), 2.90(t, 2H), 2.80(d, 2H), 2.57(s, 3H), 2.37(q, 2H), 2.08(s, 3H), 1.73(m, 1H), 1.49(m, 2H), 1.02(t, 3H), 0.94(d, 6H), 0.89(t, 3H). |
| 194 | propyl | 3-methyl-butyl | H | 2-methyl-4-methoxy-phenyl | 3-Methyl-butyl-[5-ethyl-6-(2-methyl-4-methoxy-phenyl)-2-methyl-pyridin-3-yl]-propyl-amine | MS 369 (M + H), NMR 7.24(s, 1H), 7.12(d, 1H), 6.80(s, 1H), 6.78(d, 1H), 3.83(s, 3H), 3.00(q, 2H), 2.93(q, 2H), 2.52(s, 3H), 2.37(q, 2H), 2.07(s, 3H), 1.59(m, 1H), 1.50(m, 2H), 1.37(m, 2H), 1.02(t, 3H), 0.90(m, 9H). |
| 195 | propyl | benzyl | H | 2-methyl-4-methoxy-phenyl | Benzyl-[5-ethyl-6-(2-methyl-4-methoxy-phenyl)-2-methyl-pyridin-3-yl]-propyl-amine | 389.2 |
| 196 | propyl | pyridin-2-yl-methyl | H | 2-methyl-4-methoxy-phenyl | Pyridin-2-ylmethyl-[5-ethyl-6-(2-methyl-4-methoxy-phenyl)-2-methyl-pyridin-3-yl]-propyl-amine | 390.3 |
| 197 | propyl | ethyl | H | 2-methyl-4-methoxy-phenyl | [5-ethyl-6-(2-methyl-4-methoxy-phenyl)-2-methyl-pyridin-3-yl]-ethyl-propyl-amine | MS 327 (M + H), NMR 7.25(s, 1H), 7.11(d, 1H), 6.80(s, 1H), 6.75(d, 2H), 3.81(s, 3H), 3.05(q, 2H), 2.96(t, 2H), 2.52(s, 3H), 2.36(q, 2H), 2.06(s, 3H), 2.48(m, 2H), 1.01(t, 3H), 1.00(t, 3H), 0.89(t, 3H). |
| 198 | propyl | propyl | H | 2,4-dimethoxyphenyl | [5-Ethyl-6-(2,4-dimethoxy-phenyl)-2-methyl-pyridin-3-yl]-dipropyl-amine | MS 357 (M + H), NMR 7.24(s, 1H), 7.15(d, 1H), 6.55(d, 1H), 6.51(s, 1H), 3.84(s, 3H), 3.72(s, 3H), 2.92(t, 4H), 2.51(s, 3H), 2.40(q, 2H), 1.48(m, 4H), 1.06(t, 3H), 0.88(t, 6H). |
| 199 | propyl | cyclopropyl methyl | H | 2,4-dimethoxyphenyl | Cyclopropylmethyl-[5-Ethyl-6-(2,4-dimethoxy-phenyl)-2-methyl-pyridin-3-yl]-propyl-amine | MS 369 (M + H), NMR 7.28(s, 1H), 7.16(d, 1H), 6.56(d, 1H), 6.50(s, 1H), 3.84(s, 3H), 3.72(s, 3H), 3.09(t, 2H), 2.83(d, 2H), 2.54(s, 3H), 2.39(q, 2H), 1.48(m, 2H), 1.05(t, 3H), 0.89(t, 3H), 0.88(m, 1H), 0.44(m, 2H), 0.06(m, 2H). |
| 200 | propyl | 3-methyl-butyl | H | 2,4-dimethoxyphenyl | 3-Methyl-butyl-]5-Ethyl-6-(2,4-dimethoxy-phenyl)-2-methyl-pyridin-3-yl]-propyl-amine | MS (M + H), NMR 7.22(s, 1H), 7.18(d, 1H), 6.56(d, 1H), 6.50(s, 1H), 3.87(s, 3H), 3.72(s, 3H), 2.98(t, 2H), 2.91(t, 2H), 2.52(s, 3H), 2.41(q, 2H), 1.59(m, 1H), 1.49(m, 2H), 1.38(m, 2H), 1.06(t, 3H), 0.90(d, 6H), 0.88(t, 3H). |
| 201 | propyl | benzyl | H | 2,4-dimethoxyphenyl | Benzyl-[5-Ethyl-6-(2,4-dimethoxy-phenyl)-2-methyl-pyridin-3-yl]-propyl-amine | 405.4 |

TABLE III-continued

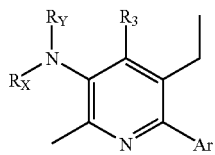

| Cmp # | $R_X$ | $R_Y$ | $R_3$ | Ar | Name | Analytical Data MS (M + 1) or NMR (ppm) |
|---|---|---|---|---|---|---|
| 202 | propyl | ethyl | H | 2,4-dimethoxyphenyl | [5-ethyl-6-(2,4-dimethoxy-phenyl)-2-methyl-pyridin-3-yl]-ethyl-propyl-amine | MS 343 (M + H), NMR 7.22(s, 1H), 7.18(d, 1H), 6.55(d, 1H), 6.50(s, 1H), 3.86(s, 3H), 3.74(s, 3H), 3.02(q, 2H), 2.94(t, 2H), 2.53(s, 3H), 2.39(q, 2H), 1.49(m, 2H), 1.04(m, 6H), 0.90(t, 3H). |
| 203 | propyl | butyl | Cl | 2,4-dimethoxyphenyl | [5-ethyl-4-chloro-6-(2,4-dimethoxy-phenyl)-2-methyl-pyridin-3-yl]-propyl-butyl-amine | MS 390 (M + H), NMR 7.12(d, 1H), 6.56(d, 1H), 6.50(s, 1H), 3.86(s, 3H), 3.74(s, 3H), 3.07(t, 4H), 2.58(s, 3H), 2.50(m, 2H), 1.49(m, 4H), 0.99(t, 3H), 0.90(t, 6H), |
| 204 | 3-methyl-butyl | propyl | methoxy | 2,4-dimethoxyphenyl | 3-Methyl-butyl[5-ethyl-4-methoxy-6-(2,4-dimethoxy-phenyl)-2-methyl-pyridin-3-yl]-propyl-amine | MS (M + H), NMR 7.15(d, 1H), 6.54(d, 1H), 6.51(s, 1H), 3.89(s, 3H), 3.86(s, 3H), 3.72(s, 3H), 3.04(m, 4H), 2.52(s, 3H), 2.49(m, 2H), 1.52(m, 3H), 1.40(m, 2H), 0.90(m, 12H). |

TABLE IV

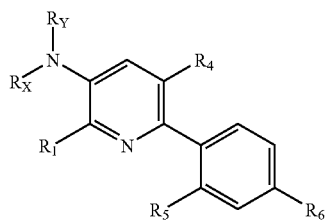

| Cmp # | $R_X$ | $R_Y$ | $R_1$ | $R_4$ | $R_5$ | $R_6$ | IUPAC Name | Analytical Data MS (M + 1) |
|---|---|---|---|---|---|---|---|---|
| 205 | H | 1-ethyl-propyl | $CH_3O$ | $CH_3$ | $CH_3O$ | $CF_3O$ | N-(1-ethylpropyl-2-methoxy-6-[2-methoxy-4-(trifluoromethoxy)phenyl]-5-methylpyridin-3-amine | 399.3 |
| 206 | H | 1-ethyl-propyl | $CH_3CH_2O-$ | $CH_3$ | $CH_3O$ | $CF_3O$ | 2-ethoxy-N-(1-ethylpropyl)-6-[2-methoxy-4-(trifluoromethoxy)phenyl]-5-methylpyridin-3-amine | 413.4 |
| 207 | propyl | propyl | $CH_3CH_2$ | $CH_3$ | $CH_3O$ | $CF_3O$ | 2-ethyl-6-[2-methoxy-4-(trifluoromethoxy)phenyl]-5-methyl-N,N-dipropylpyridin-3-amine | 411 |
| 208 | H | propyl | $CH_3CH_2$ | $CH_3$ | $CH_3O$ | $CF_3O$ | 2-ethyl-6-[2-methoxy-4-(trifluoromethoxy)phenyl]-5-methyl-N-propylpyridin-3-amine | 369.2 |
| 209 | H | 1-ethyl-propyl | $CH_3CH_2$ | $CH_3$ | $CH_3O$ | $CF_3O$ | 2-ethyl-N-(1-ethylpropyl)-6-[2-methoxy-4-(trifluoromethoxy)phenyl]-5-methylpyridin-3-amine | Rf 0.45 (5% MeOH in dichloromethane) |
| 210 | H | $CH_3(CH_2)_2(C=O)$ | $CH_3O$ | $CH_3$ | $CH_3O$ | $CF_3O$ | N-{2-methoxy-6-[2-methoxy-4-(trifluoromethoxy)phenyl]-5-methylpyridin-3-yl}butanamide | 399.3 |

Additional compounds of Formula I.

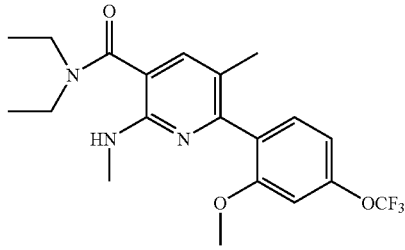

211. N,N-diethyl-6-[2-methoxy-4-(trifluoromethoxy)phenyl]-5-methyl-2-(methylamino)nicotinamide MS (M+1): 426.4
212. 2-Ethyl-1-[5-ethyl-6-(4-isopropoxy-2-methoxy-phenyl)-2-methoxy-pyridin-3-yl]-butan-1-ol
213. 5-Ethyl-6-(4-isopropoxy-2-methoxy-phenyl)-2-methylamino-N,N-dipropyl-nicotinamide Example 10

Additional Compounds of Formula I

The $R_2$-Matrix, Het-Matrix, and Ar-Matrix tables below set forth a number of additional compounds of Formula I. Compounds are formed by combining any element from the $R_2$ Matrix with any element from the Het-matrix to form an $R_2$-Het moiety, and then combining this moiety with any element of the Ar-Matrix to form a compound of Formula I. For example, the combination of element 143 from the $R_2$-Matrix, with element 203 from the Het-matrix, gives the moiety 143203. This moiety is then combined with element 304 from the Ar-matrix, to form a compound of Formula I, compound 143203304, which is [6-(2,4-Dimethoxy-phenyl)-2,5-diethyl-pyridin-3-yl]-(1-ethyl-propyl)-amine.

$R_2$-Het-Ar ⟹ 143203304 ⟹

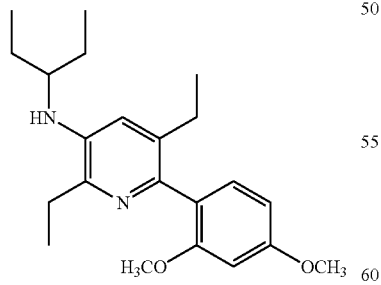

Thus, the invention includes compounds of the formula $R_2$-Het-Ar and the pharmaceutically acceptable salts thereof, wherein $R_2$ is any element, 102–151, of the $R_2$ Matrix, Het is any element, 201–232 of the Het-Matrix, and Ar is any element, 301–380 of the Ar-Matrix.

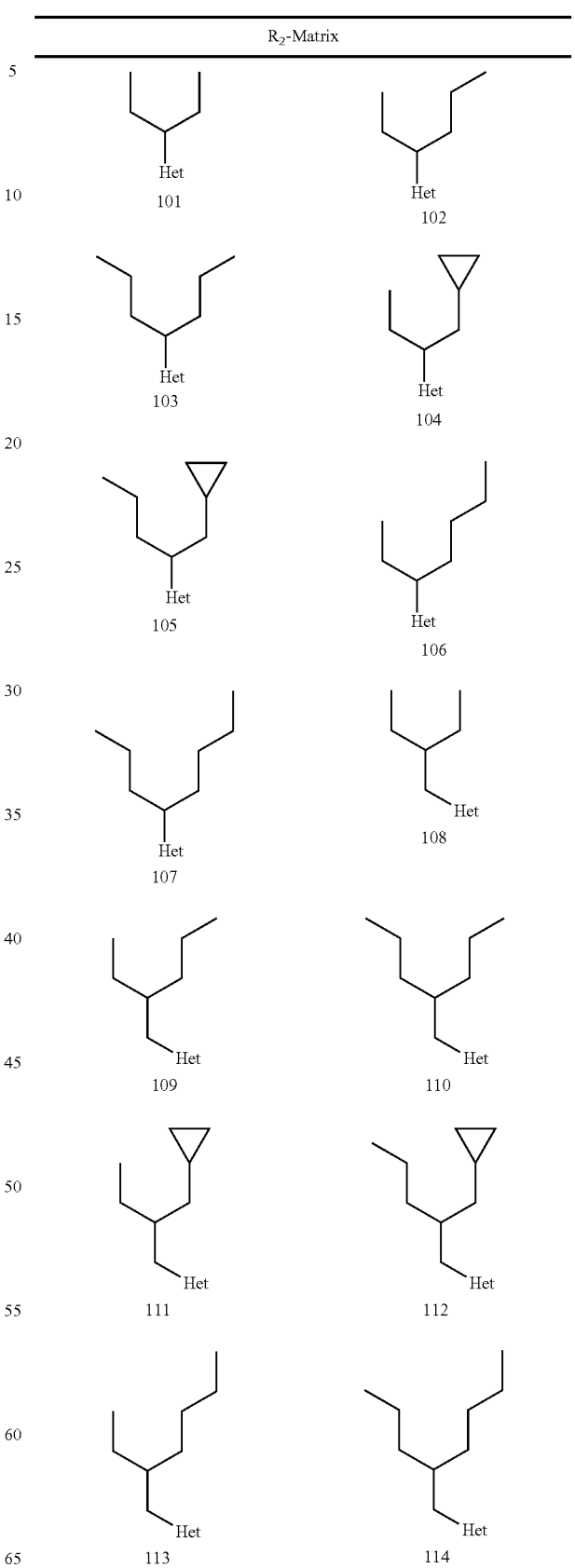

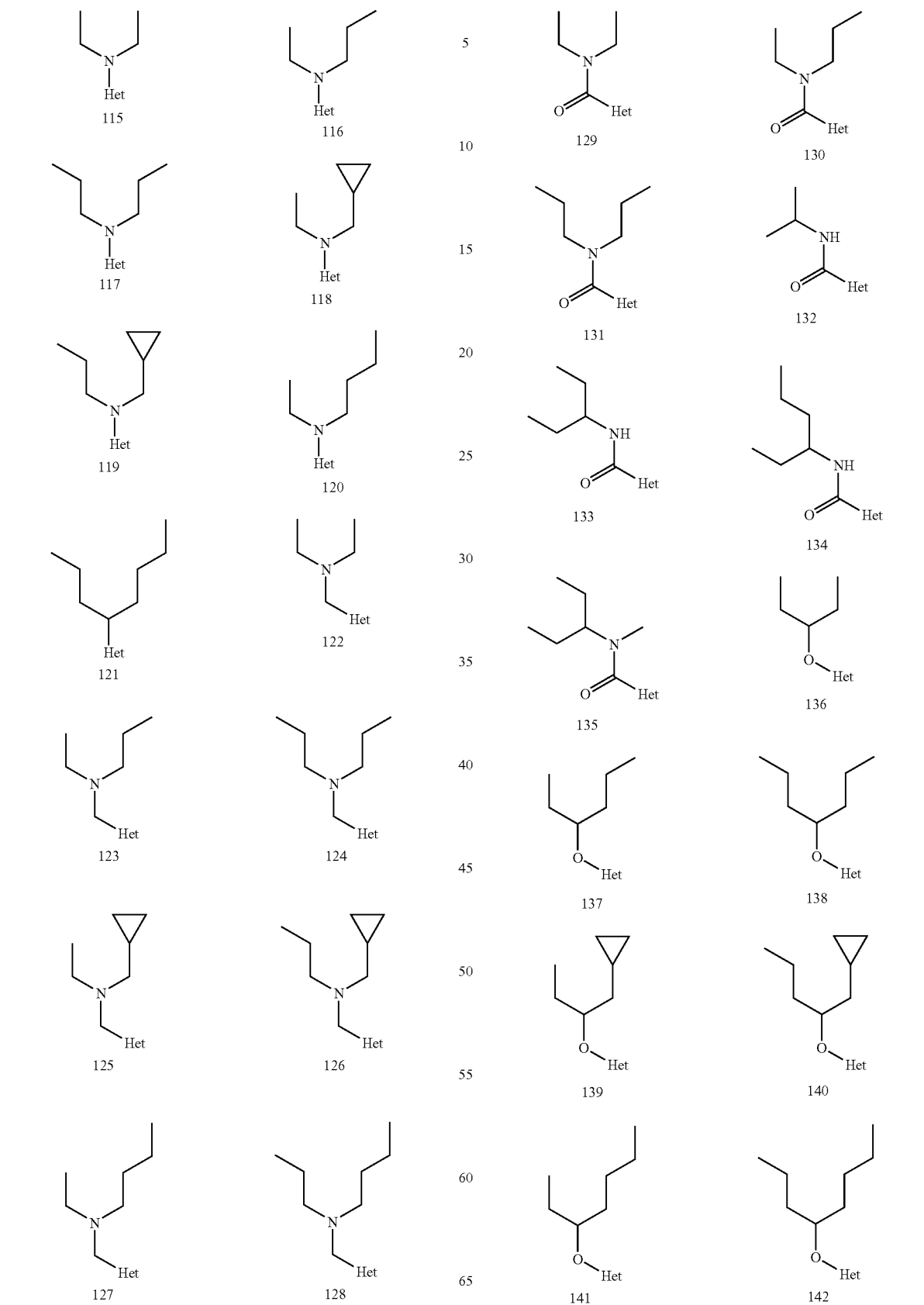

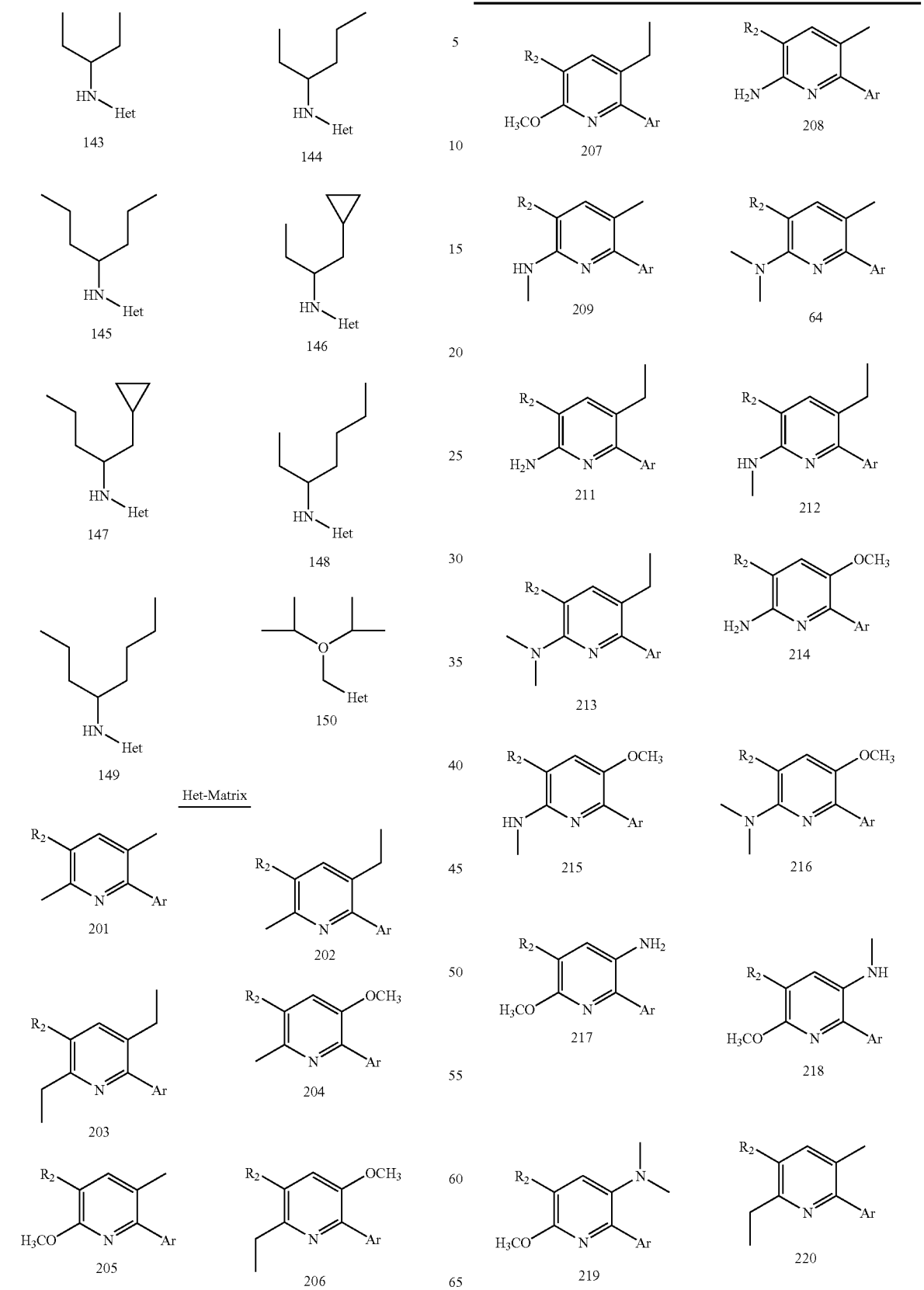

-continued
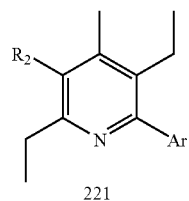
221
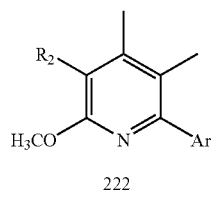
222
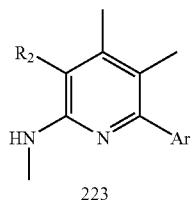
223
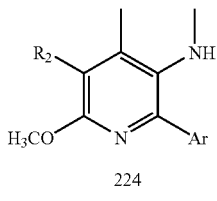
224
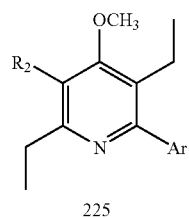
225
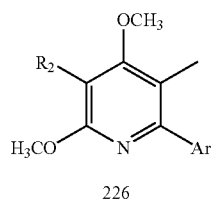
226
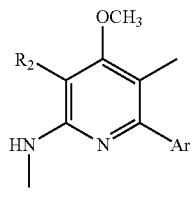
227
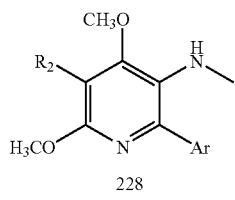
228
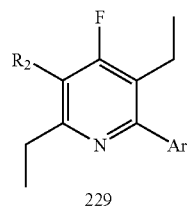
229
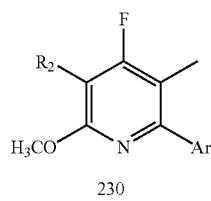
230
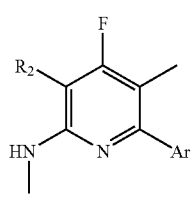
231
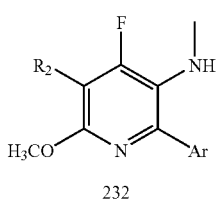
232
Ar-Matrix
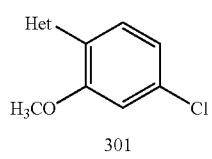
301
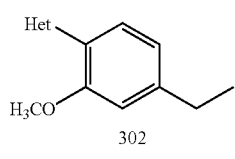
302
-continued
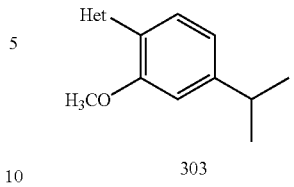
303
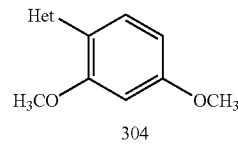
304
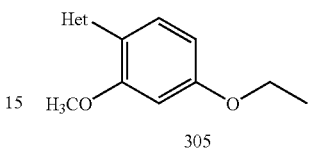
305
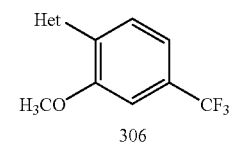
306
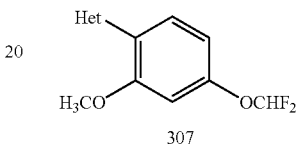
307
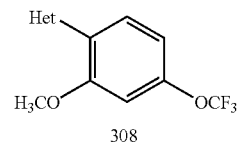
308
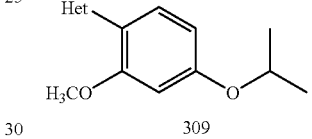
309
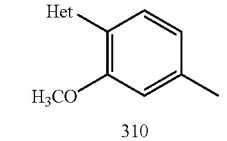
310
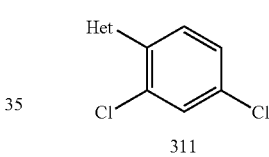
311
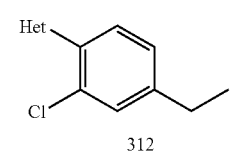
312
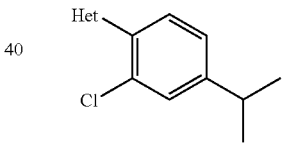
313
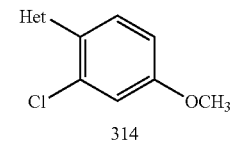
314
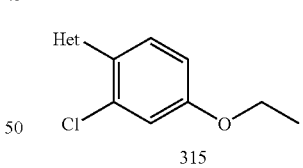
315
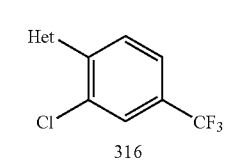
316
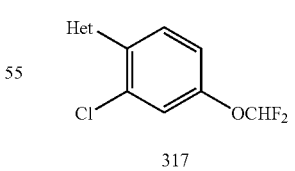
317
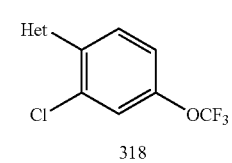
318
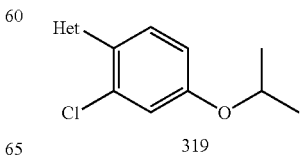
319
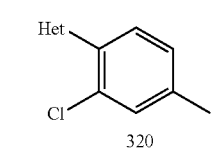
320

-continued
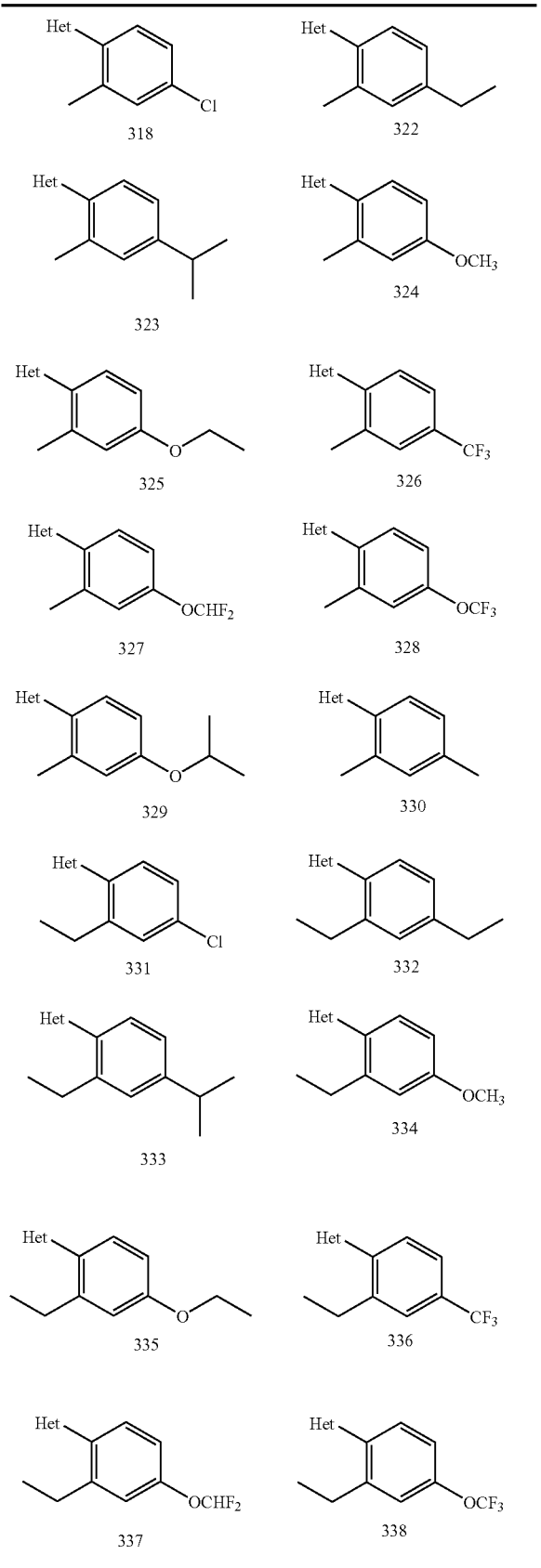
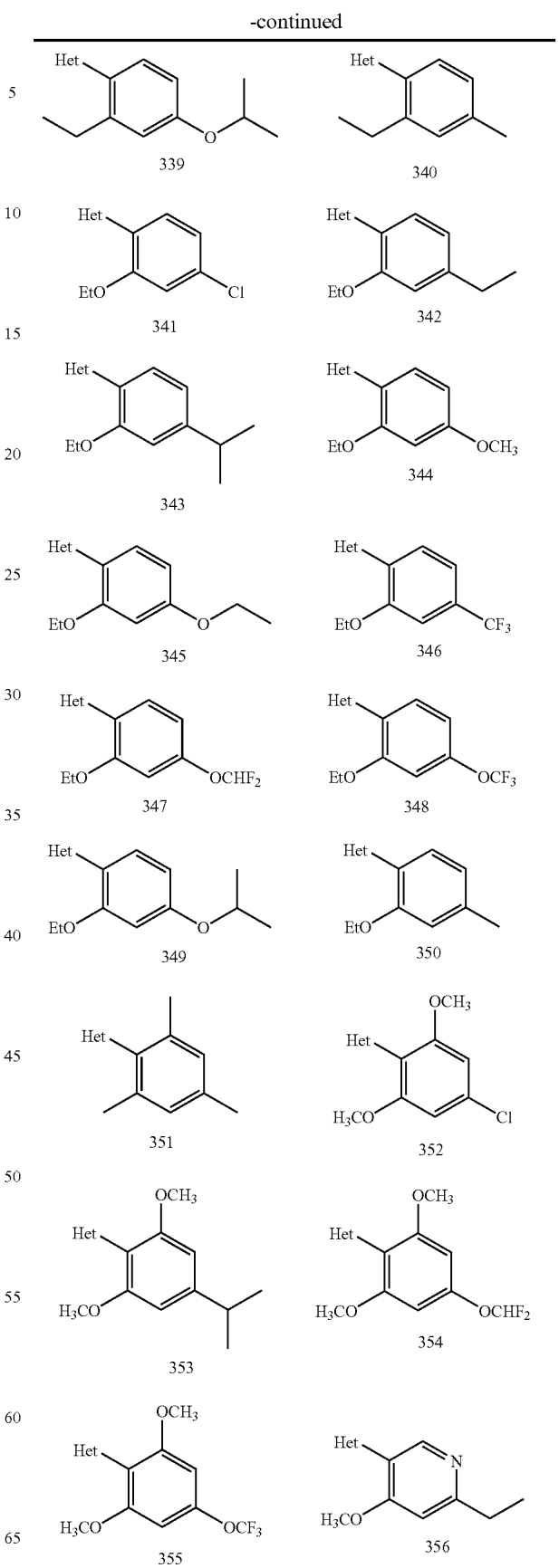

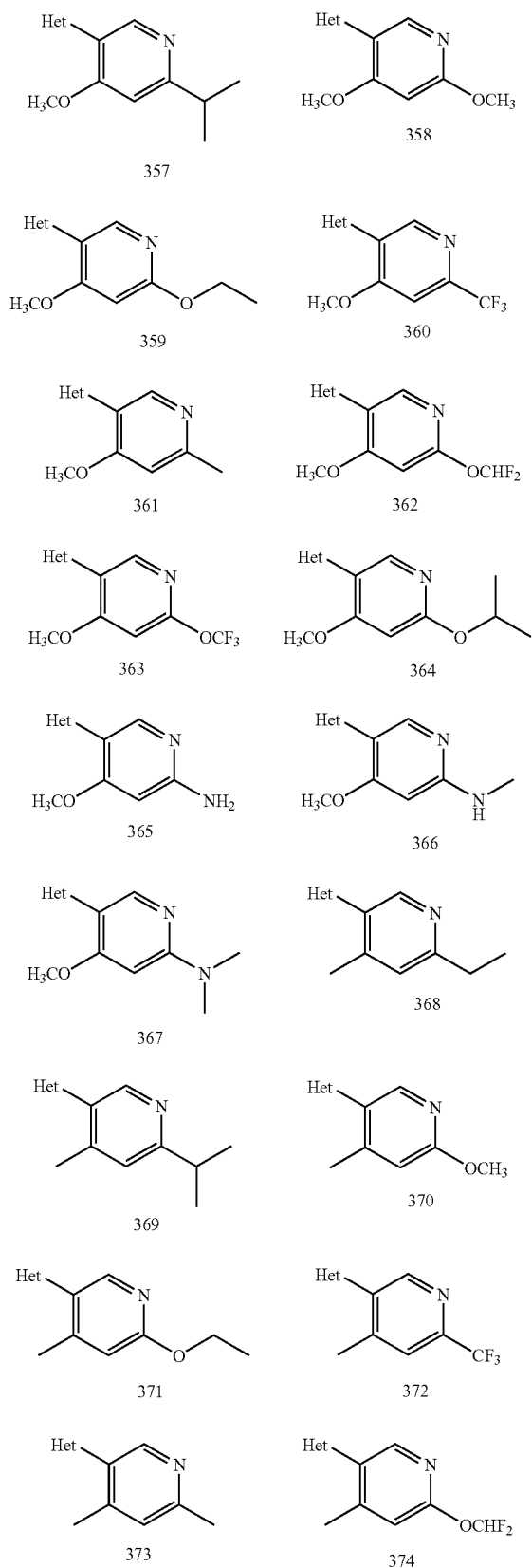
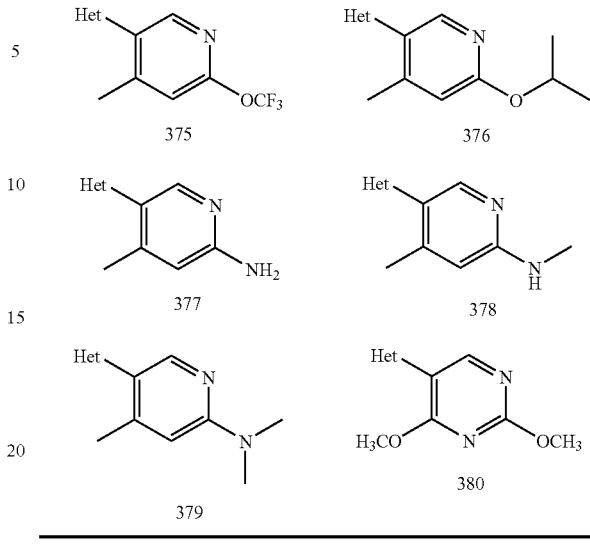

Example 11

Assay for CRF Receptor Binding Activity

As discussed above, the following assay is defined herein as a standard in vitro CRF receptor binding assay. The pharmaceutical utility of compounds of this invention is indicated by the following assay for CRF1 receptor activity.

The CRF receptor binding is performed using a modified version of the assay described by Grigoriadis and De Souza (*Methods in Neurosciences*, Vol. 5, 1991). IMR-32 human neuroblastoma cells, a cell line that can be induced to express the CRF1 receptor, are cultured in growth medium consisting of EMEM w/Earle's BSS (JRH Biosciences, Cat# 51411) supplemented with 10% Fetal Bovine Serum, 25 mM HEPES (pH 7.2), 1 mM Sodium Pyruvate, and Non-Essential Amino Acids (JRH Biosciences, Cat# 58572). Stock cultures of cells are grown to confluence and subcultured twice per week at split ratios of 1:2 to 1:4 (cells are dislodged during subculturing using No-Zyme, JRH Biosciences, Cat# 59226). To induce CRF1 receptor expression, the cells are grown to approximately 80% confluence and then changed to growth media containing 2.5 μM 5-bromo-2' deoxyuridine (BrdU, Sigma, Cat# B9285). Growth media containing BrdU is replaced every 3–4 days and the cells are harvested via centrifugation (using No-Zyme) after 10 days of BrdU treatment. Harvested cells are stored frozen at −80° C. until needed for the preparation of membrane homogenates.

To prepare receptor-containing membranes cells are homogenized in wash buffer (50 mM Tris HCl, 10 mM $MgCl_2$, 2 mM EGTA, pH 7.4) and centrifuged at 48,000×g for 10 minutes at 4° C. The pellet is re-suspended in wash buffer and the homogenization and centrifugation steps are performed once more.

Membrane pellets (containing CRF receptors) are resuspended and brought to a final concentration of 1.0 mg membrane protein/ml in binding buffer (Tris buffer above with 0.1% BSA and 0.1 mM bacitracin). For the binding assay, 150 microliters of the membrane preparation is added to 96 well microtube plates containing 50 microliters of $^{125}$I-CRF (SA 2200 Ci/mmol, final concentration of 100 pM)

and 2 microliters of test compound. Binding is carried out at room temperature for 2 hours. Plates are then harvested using 50 mM Tris buffer pH 7.4, on a BRANDEL 96 well cell harvester and filters (soaked in 1% PEI for 1.5 hours) are counted for gamma emissions on a Wallac 1205 BETA-PLATE liquid scintillation counter. Non-specific binding is defined by 2 micromolar cold CRF. $IC_{50}$ values are calculated with the non-linear curve fitting program RS/1 (BBN Software Products Corp., Cambridge, Mass.).

The binding affinity for the compounds of Formula I expressed as an $IC_{50}$ value, generally ranges from about 0.5 nanomolar to about 10 micromolar. Preferred compounds of Formula I exhibit $IC_{50}$ values of less than or equal to 1.5 micromolar, more preferred compounds of Formula I exhibit $IC_{50}$ values of less than 500 nanomolar, still more preferred compounds of Formula I exhibit $IC_{50}$ values of less than 100 nanomolar, and most preferred compound of Formula I exhibit $IC_{50}$ values of less than 10 nanomolar.

Compounds of Formula I shown in Examples 1–9 for which analytical data is provided have been tested in this assay and found to exhibit $IC_{50}$ values of less than or equal to 4 micromolar.

Example 12

Preparation of Radiolabled Probe Compounds of Formula I

The compounds of Formula I are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of Formula I as substrate. In addition, certain precursors may be subjected to tritium-halogen exchange with tritium gas, tritium gas reduction of unsaturated bonds, or reduction using sodium borotritide, as appropriate.

Example 13

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of Formula I prepared as described in the preceding Examples.

Example 14

Additional Aspects of Preferred Compounds of Formula I

The most preferred compounds of Formula I are suitable for pharmaceutical use in treating human patients. Accordingly, such preferred compounds are non-toxic. They do not exhibit single or multiple dose acute or long-term toxicity, mutagenicity (e.g., as determined in a bacterial reverse mutation assay such as an Ames test), teratogenicity, tumorogenicity, or the like, and rarely trigger adverse effects (side effects) when administered at therapeutically effective dosages.

Preferably, administration of such preferred compounds of Formula I at certain doses (e.g., doses yielding therapeutically effective in vivo concentrations or preferably doses of 10, 50, 100, 150, or 200 mg/kg—preferably 150 mg/kg—administered parenterally or preferably orally) does not result in prolongation of heart QT intervals (i.e., as determined by electrocardiography, e.g., in guinea pigs, minipigs or dogs). When administered daily for 5 or preferably ten days, such doses of such preferred compounds also do not cause liver enlargement resulting in an increase of liver to body weight ratio of more than 100%, preferably not more than 75% and more preferably not more than 50% over matched controls in laboratory rodents (e.g., mice or rats). In another aspect such doses of such preferred compounds also preferably do not cause liver enlargement resulting in an increase of liver to body weight ratio of more than 50%, preferably not more than 25%, and more preferably not more than 10% over matched untreated controls in dogs or other non-rodent animals.

In yet another aspect such doses of such preferred compounds also preferably do not promote the release of liver enzymes (e.g., ALT, LDH, or AST) from hepatocytes in vivo. Preferably such doses do not elevate such enzymes by more than 100%, preferably not by more than 75% and more preferably not by more than 50% over matched untreated controls in laboratory rodents. Similarly, concentrations (in culture media or other such solutions that are contacted and incubated with cells in vitro) equivalent to two, fold, preferably five-fold, and most preferably ten-fold the minimum in vivo therapeutic concentration do not cause release of any of such liver enzymes from hepatocytes in vitro.

Because side effects are often due to undesirable receptor activation or antagonism, preferred compounds of Formula I exert their receptor-modulatory effects and bind to the CRF1 receptor with high selectivity. This means that they do not bind to certain other receptors (i.e., other than CRF receptors) with high affinity, but rather only bind to, activate, or inhibit the activity of such other receptors with affinity constants of greater than 100 nanomolar, preferably greater than 1 micromolar, more preferably greater than 10 micromolar and most preferably greater than 100 micromolar. Such receptors preferably are selected from the group including ion channel receptors, including sodium ion channel receptors, neurotransmitter receptors such as alpha- and beta-adrenergic receptors, muscarinic receptors (particularly m1, m2, and m3 receptors), dopamine receptors, and metabotropic glutamate receptors; and also include histamine receptors and cytokine receptors, e.g., interleukin receptors, particularly IL-8 receptors. The group of other receptors to which preferred compounds do not bind with high affinity also includes GABAA receptors, bioactive peptide receptors (including NPY and VIP receptors), neurokinin receptors, bradykinin receptors (e.g., BK1 receptors and BK2 receptors), and hormone receptors (including thyrotropin releasing hormone receptors and melanocyte-concentrating hormone receptors).

Example 15

Absence of Sodium Ion Channel Activity

Preferred compounds of Formula I do not exhibit activity as sodium ion channel blockers. Sodium channel activity may be measured a standard in vitro sodium channel binding assays such as the assay given by Brown et al. (J. Neurosci. (1986) 265: 17995–18004). Preferred compounds of Formula I exhibit less than 15 percent inhibition, and more preferably less than 10 percent inhibition, of sodium channel specific ligand binding when present at a concentration of 4 uM. The sodium ion channel specific ligand used may be labeled batrachotoxinin, tetrodotoxin, or saxitoxin. Such assays, including the assay of Brown referred to above, are performed as a commercial service by CEREP, INC., Redmond, Wash.

Alternatively, sodium ion channel activity may be measured in vivo in an assay of anti-epileptic activity. Anti-epileptic activity of compounds may be measured by the ability of the compounds to inhibit hind limb extension in the supramaximal electroshock model. Male Han Wistar rats (150–200 mg) are dosed i.p. with a suspension of 1 to 20 mg of test compound in 0.25% methylcellulose 2 hr. prior to test. A visual observation is carried out just prior to testing for the presence of ataxia. Using auricular electrodes a current of 200 mA, duration 200 milliseconds, is applied and the presence or absence of hind limb extension is noted. Preferred compounds of Formula I do not exhibit significant anti-epileptic activity at the $p<0.1$ level of significance or more preferably at the $p<0.05$ level of significance as measured using a standard parametric assay of statistical significance such as a student's T test.

Example 16

Optimal In Vitro Half-life

Compound half-life values ($t_{1/2}$ values) may be determined via the following standard liver microsomal half-life assay. Liver microsomes are obtained from pooled liver samples and prepared so that the P-450 enzyme content is approximately 0.5 nmol/ mg protein. Reactions are preformed in a 5 ml well deep-well plate as follows:

Phosphate buffer: 19 mL 0.1 M $NaH_2PO_4$, 81 mL 0.1 $Na_2HPO_4$, pH 7.4 with $H_3PO_4$.

CoFactor Mixture: 16.2 mg NADP, 45.4 mg Glucose-6-phosphate in 4 mL 100 mM $MgCl_2$. Glucose-6-phosphate dehydrogenase: 214.3 microliters glucose-6-phosphate dehydrogenase, 1285.7 microliters distilled water Starting Reaction Mixture: 3 mL CoFactor Mixture, 1.2 mL Glucose-6-phosphate dehydrogenase 6 identical sample wells each containing 25 microliters microsomes, 5 microliters test compound (from a 100 uM stock), and 399 microliters 0.1 M phosphate buffer, pH 7.4, are prepared. A seventh well containing 25 microliters microsomes, 399 microliters 0.1 M phosphate buffer, pH 7.4, and 5 microliters(from a 100 uM stock) of a compound, e.g. diazapam, clozapine, with known metabolic properties is used as a positive control. Reactions are preincubated at 39° C. for 10 minutes. 71 microliters Starting Reaction Mixture is added to 5 of the 6 reaction wells and to the positive control well, 71 microliters 100 mM $MgCl_2$ is added to the sixth reaction well, which is used as a negative control. At each time point (0, 1, 3, 5, and 10 minutes) 75 microliters reaction is pipetted into a 96-well deep-well plate reaction well containing 75 microliters ice-cold acetonitrile. Samples are vortexed and centrifuged 10 minutes at 6000 rpm (Sorval T 6000D rotor). Supernatant, 75 microliters from each reaction well, is transferred to a 96-well plate containing 150 microliters internal standard per well. The remaining test compound is quantitated via LCMS. Compound concentration vs time is plotted and commercially available statistical software is used to extrapolate to the $t_{1/2}$ value of the test compound.

Preferred compounds of Formula I exhibit in vitro $t_{1/2}$ values of greater than 10 minutes and less than 4 hours. Most preferred compounds of Formula I exhibit in vitro $t_{1/2}$ values of between 30 minutes and 1 hour in human liver microsomes.

Example 17

MDCK Toxicity

Compounds causing acute cytotoxicity will decrease ATP production by Madin Darby canine kidney (MDCK) cells in the following assay.

MDCK cells, ATCC no. CCL-34 (American Type Culture Collection, Manassas, Va.) are maintained in sterile conditions following the instructions in the ATCC production information sheet. The PACKARD, (Meriden, Conn.) ATP-LITE-M Luminescent ATP detection kit, product no. 6016941, allows measurement ATP production in MDCK cells.

Prior to assay 1 microliter of test compound or control sample is pipetted into PACKARD (Meriden, Conn.) clear bottom 96-well plates. Test compounds and control samples are diluted in DMSO to give final concentration in the assay of 10 micromolar, 100 micromolar, or 200 micromolar. Control samples are drug or other compounds having known toxicity properties.

Confluent MDCK cells are trypsinized, harvested, and diluted to a concentration of $0.1 \times 10^6$ cells/ml with warm (37° C.) VITACELL Minimum Essential Medium Eagle (ATCC catalog # 30–2003). 100 microliters of cells in medium is pipetted into each of all but five wells of each 96-well plate. Warm medium without cells (100 ul) is pipetted in the remaining five wells of each plate. These wells, to which no cells are added, are used to determine the standard curve. The plates are then incubated at 37° C. under 95% $O_2$, 5% $CO_2$ for 2 hours with constant shaking. After incubation, 50 microliters of mammalian cell lysis solution is added per well, the wells are covered with PACKARD TOPSEAL stickers, and plates are shaken at approximately 700 rpm on a suitable shaker for 2 minutes.

During the incubation, PACKARD ATP LITE-M reagents are allowed to equilibrate to room temperature. Once equilibrated the lyophilized substrate solution is reconstituted in 5.5 ml of substrate buffer solution (from kit). Lyophilized ATP standard solution is reconstituted in deionized water to give a 10 mM stock. For the five control wells, 10 microliters of serially diluted PACKARD standard is added to each of the five standard curve control wells to yield a final concentration in each subsequent well of 200 nM, 100 nM, 50 nM, 25 nM, and 12.5 nM.

PACKARD substrate solution (50 ul) is added to all wells. Wells are covered with PACKARD TOPSEAL stickers, and plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter, e.g. PACKARD TOPCOUNT Microplate Scintillation and Luminesense Counter or TECAN SPECTRAFLUOR PLUS.

Luminescence values at each drug concentration are compared to the values computed from the standard curve for that concentration. Preferred test compounds exhibit luminescence values 80% or more of the standard, or preferably 90% or more of the standard, when a 10 micromolar (uM) concentration of the test compound is used. When a 100 micromolar concentration of the test compound is used, preferred test compounds exhibit luminescence values 50% or more of the standard, or more preferably 80% or more of the standard.

What is claimed is:

1. A compound of the formula

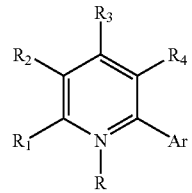

or a pharmaceutically acceptable salt thereof, wherein:

Ar is selected from the group consisting of phenyl or naphthyl, each of which is substituted with up to 5 $R_A$ groups;

R is oxygen or absent;

$R_1$ is selected from amino, nitro, and mono- or di-$C_1$–$C_6$carbhydryl$_1$amino, where each carbhydryl$_1$ is independently straight or branched, contains 0 or 1 double or triple bonds, and is unsubstituted or substituted with one or more substituents independently chosen from halogen, hydroxy, oxo, cyano, $C_1$–$C_4$alkoxy, amino, and mono- or di-($C_1$–$C_4$alkyl)amino;

$R_3$ is selected from hydrogen, halogen, hydroxy, amino, nitro, $C_1$–$C_6$carbhydryl$_1$, $C_1$–$C_6$carbhydryl$_1$-O—, mono- or di-$C_1$–$C_6$carbhydryl$_1$amino, $C_3$–$C_7$cycloalkyl$_2$($C_0$–$C_4$carbhydryl$_1$), $C_3$–$C_7$cycloalkenyl$_2$($C_0$–$C_4$carbhydryl$_1$), $C_3$–$C_7$cycloalkyl$_2$($C_0$–$C_4$carbhydryl$_1$)-O—, $C_3$–$C_7$cycloalkenyl$_2$($C_0$–$C_4$carbhydryl$_1$)-O—, halo$C_1$–$C_6$carbhydryl$_1$, halo$C_1$–$C_6$carbhydryl$_1$-O—, and —S(O)$_n$($C_1$–$C_6$carbhydryl$_1$), where each carbhydryl$_1$ is independently straight or branched, contains 0 or 1 double or triple bonds, and is unsubstituted or substituted with one or more substituents independently chosen from halogen, hydroxy, oxo, cyano, ($C_1$–$C_4$alkoxy, amino, and mono- or di-($C_1$–$C_4$alkyl)amino, and where each $C_3$–$C_7$cycloalkyl$_2$ and $C_3$–$C_7$cycloalkenyl$_2$ is optionally substituted by one or more substituents independently chosen from halogen, hydroxy, oxo, cyano, $C_1$–$C_4$alkoxy, amino, and mono- or di-($C_1$–$C_4$)alkylamino;

$R_4$ is selected from hydrogen, amino, hydroxy, nitro, $C_1$–$C_6$carbhydryl$_1$, $C_1$–$C_6$carbhydryl$_1$-O—, mono- or di-$C_1$–$C_6$carbhydryl$_1$amino, $C_3$–$C_7$cycloalkyl$_2$ ($C_0$–$C_4$carbhydryl$_1$), $C_0$–$C_4$carbhydryl$_1$, ($C_0$–$C_4$carbhydryl$_1$)-O—, ($C_0$–$C_4$carbhydryl$_1$)-O—, halo$C_1$–$C_6$carbhydryl$_1$-O—, and —S(O)$_n$ ($C_1$–$C_6$carbhydryl$_1$), $C_3$–$C_7$cycloalkenyl$_2$, $C_3$–$C_7$cycloalkyl$_2$, $C_3$–$C_7$cycloalkenyl$_2$, halo$C_1$–$C_6$carbhydryl$_1$, and —S(O)$_n$ ($C_1$–$C_6$carbhydryl$_1$), where each carbhydryl$_1$ is independently straight or branched, contains 0 or 1 double or triple bonds, and is unsubstituted or substituted with one or more substituents independently chosen train halogen, hydroxy, oxo, cyano, $C_1$–$C_4$alkoxy, amino, and mono- or di-($C_1$–$C_4$alkyl)amino, and where each $C_3$–$C_7$cycloalkyl$_2$ and $C_3$–$C_7$cycloalkenyl$_2$ is optionally substituted by one or more substituents independently chosen from halogen, hydroxy, oxo, cyano, $C_2$–$C_4$alkoxy, amino, and mono- or di-($C_1$–$C_4$)alkylamino;

$R_2$ is selected from the group consisting of —OR$_C$, —SR$_C$, —NHR$_C$, and —NR$_C$R$_D$;

X is independently selected at each occurrence from the group consisting of —CH$_2$—, —CHR$_D$—, —O—, —C(=O)—, —C(=O)O—, —S(O)$_n$—, —NH—, —NR$_D$—, —C(=O)NH—, —C(=O)NR$_D$—, —S(O)$_n$NH—, —S(O)$_n$NR$_D$—, —OC(=S)S—, —NHC(=O)—, —NR$_D$C(=O)—, —NHS(O)$_n$—, and —NR$_D$S(O)$_n$—;

Y and Z are independently selected at each occurrence from: 3- to 7-membered carbocyclic or heterocyclic groups, which are saturated, partially unsaturated, or aromatic, which may be further substituteted with one or more substituents independently selected from halogen, oxo, hydroxy, amino, cyano, $C_1$–$C_4$alkyl, $C_1$–$C_4$alkoxy, mono- or di-($C_1$–$C_4$alkyl)amino, and —S(O)$_n$(alkyl), wherein said 3- to 7-membered heterocyclic groups contain from 1 to 3 heteroatom(s) independently selected from N, O, and S, with remaining ring members being carbon;

$R_A$ is independently selected at each occurrence from halogen, cyano, nitro, halo($C_1$–$C_6$)alkyl, halo ($C_1$–$C_6$alkoxy, hydroxy, amino, $C_1$–$C_6$alkyl substituted with 0–2 $R_B$, $C_2$–$C_6$alkenyl substituted with 0–2 $R_n$, $C_2$–$C_6$alkynyl substituted with 0–2 $R_B$, $C_3$–$C_7$cycloalkyl substituted with 0–2 $R_u$, ($C_3$–$C_7$cycloalkyl)$C_1$–$C_4$alkyl substituted with 0–2 $R_n$, $C_1$–$C_6$alkoxy substituted with 0–2 $R_B$, —NH ($C_1$–$C_6$alkyl) substituted with 0–2 $R_B$, —N($C_1$–$C_6$alkyl)($C_1$–$C_6$alkyl) where each $C_1$–$C_6$alkyl is independently substituted with 0–2 $R_B$, —XR$_C$, and Y;

$R_B$ is independently selected at each occurrence from halogen, hydroxy, cyano, amino, $C_1$–$C_4$alkyl, $C_1$–$C_4$alkoxy, mono- or di-($C_1$–$C_4$alkyl)amino, —S(O)$_n$(alkyl), halo($C_1$–$C_4$)alkyl, halo($C_1$–$C_4$)alkoxy, —CO($C_1$–$C_4$alkyl), —CONH($C_1$–$C_4$alkyl), —CON ($C_1$–$C_4$alkyl)($C_1$–$C_4$alkyl), —XR$_C$, and Y;

$R_C$ is independently selected at each occurrence from:

straight, branched, and cyclic alkyl groups, and (cycloalkyl)alkyl groups, having 1 to 8 carbon atoms, and containing zero or one double or triple bonds, each of which 1 to 8 carbon atoms may be further substituted with one or more substituent(s) independently selected from oxo, hydroxy, halogen, cyano, amino, $C_1$–$C_6$alkoxy, and mono or di-($C_1$–$C_6$alkyl)amino;

$R_D$ is independently selected at each occurrence from hydrogen, and straight, branched, and cyclic alkyl groups, and (cycloalkyl)alkyl groups, having 1 to 8 carbon atoms, and containing zero or one double or triple bonds, each of which 1 to 8 carbon atom may be further substituted with one or more substituent(s) independently selected from oxo, hydroxy, halogen, cyano, amino, $C_1$–$C_6$alkoxy, mono- or di-($C_1$–$C_4$alkyl)amino, —NHC(=O)($C_1$–$C_6$alkyl), —N($C_1$–$C_6$alkyl)C(=O)($C_1$–$C_6$alkyl), —NHS(O)$_n$($C_1$–$C_6$alkyl), —S(O)$_n$($C_1$–$C_6$alkyl), —S(O)$_n$NH($C_1$–$C_6$alkyl), —S(O)$_n$N($C_1$–$C_6$alkyl)($C_1$–$C_6$alkyl), and Z; and n is independently selected at each occurrence from 0, 1, and 2;

with the proviso that not all of $R_1$, $R_2$, $R_3$, and $R_4$ are unsubstituted alkyl and not all of $R_1$, $R_3$, and $R_4$ are hydrogen.

2. A compound or salt according to claim 1, wherein R is absent and Ar is phenyl which is substituted with $R_A$ in at least 1 position ortho to the point of attachment of Ar in Formula I, and optionally substituted with up to 2 additional $R_A$ groups.

3. A compound or salt according to claim 2 wherein
R is absent;
$R_3$ is selected from the group consisting of i) hydrogen, ii) halogen, iii) $C_1$–$C_3$alkyl, iv) $C_1$–$C_3$alkoxy, v) ($C_3$–$C_7$cycloalkyl)$C_0$–$C_3$alkyl, vi) ($C_3$–$C_7$cycloalkyl)$C_0$–$C_3$alkoxy, vii) mono- or di-($C_1$–$C_3$alkyl)amino, viii) $C_1$–$C_3$haloalkyl, and ix) $C_1$–$C_3$haloalkoxy wherein each of iii, iv, v, vi, and vii is unsubstituted or substituted by 1–3 groups independently chosen from hydroxy, amino, cyano, and halogen; and
$R_4$ is selected from the group consisting of i) hydrogen, ii) $C_1$–$C_3$alkyl, iii) $C_1$–$C_3$alkoxy, iv) ($C_3$–$C_7$cycloalkyl)$C_0$–$C_3$alkyl, v) ($C_3$–$C_7$cycloalkyl)$C_0$–$C_3$alkoxy, vi) mono- or di-($C_1$–$C_3$alkyl)amino, vii) $C_1$–$C_3$haloalkyl, and viii) $C_1$–$C_3$haloalkoxy, wherein each of ii, iii, iv, v, and vi is unsubstituted or substituted by 1–3 groups independently chosen from hydroxy, amino, cyano, and halogen.

4. A compound or salt according to claim 1, wherein:
R is absent;
Ar is phenyl which is substituted with $R_A$ in at least 1 position otho to the point of attachment of Ar in Formula I, end optionally substituted with up to 2 additional $R_A$ groups; and
$R_C$ and $R_D$, which may be the same or different, are independently selected at each occurrence from straight, branched, or cyclic alkyl groups having from 1 to 8 carbon atoms, which alkyl groups may contain one double or triple bonds.

5. A compound or salt according to claim 4, wherein:
$R_3$ is selected from the group consisting of i) hydrogen, ii) halogen, iii) $C_1$–$C_3$alkyl, iv) $C_1$–$C_3$alkoxy, v) ($C_3$–$C_7$cycloalkyl)$C_0$–$C_3$alkyl, vi) ($C_3$–$C_7$cycloalkyl)$C_0$–$C_3$alkoxy, vii) mono- or di-($C_1$–$C_3$alkyl)amino, viii) $C_1$–$C_3$haloalkyl, and ix) $C_1$–$C_3$haloalkoxy, wherein each of iii, iv, v, vi, and vii is unsubstituted or substituted by 1–3 groups independently chosen from hydroxy, amino, cyano, and halogen; and
$R_4$ is selected from the group consisting of i) hydrogen, ii) $C_1$–$C_3$alkyl, iii) $C_1$–$C_3$alkoxy, iv) ($C_3$–$C_7$cycloalkyl)$C_0$–$C_3$alkyl, v) ($C_3$–$C_7$cycloalkyl)$C_0$–$C_3$alkoxy, vi) mono- or di-($C_1$–$C_3$alkyl)amino, vii) $C_1$–$C_3$haloalkyl, and viii) $C_1$–$C_3$haloalkoxy, wherein each of ii, iii, iv, v, and vi is unsubstituted or substituted by 1–3 groups independently chosen from hydroxy, amino, cyano, and halogen.

6. A compound or salt according to claim 1, wherein:
R is absent;
Ar is phenyl which is substituted in at least one position ortho to the point of attachment of Ar in Formula I with a substituent selected from halogen, cyano, nitro, halo($C_1$–$C_6$)alkyl, halo($C_1$–$C_6$)alkoxy, hydroxy, amino, $C_1$–$C_6$alkyl, $C_2$–$C_6$alkenyl, $C_2$–$C_6$alkynyl, $C_3$–$C_7$cycloalkyl, ($C_3$–$C_7$cycloalkyl)$C_1$–$C_4$alkyl, $C_1$–$C_6$alkoxy, and mono- or di-($C_1$–$C_6$alkyl)amino and optionally substituted with up to 2 additional substituents independently selected from halogen, cyano, nitro, halo($C_1$–$C_6$)alkyl, halo($C_1$–$C_6$)alkoxy, hydroxy, amino, $C_1$–$C_6$alkyl, $C_2$–$C_6$alkenyl, $C_2$–$C_6$alkynyl, $C_3$–$C_7$cycloalkyl, ($C_3$–$C_7$cycloalkyl)$C_1$–$C_4$alkyl, $C_1$–$C_6$alkoxy, and mono- or di-($C_1$–$C_6$alkyl)amino;
$R_3$ is selected from the group consisting of i) hydrogen, ii) halogen, iii) $C_1$–$C_3$alkyl, iv) $C_1$–$C_3$alkoxy, v) ($C_3$–$C_7$cycloalkyl)$C_0$–$C_3$alkyl, vi) ($C_3$–$C_7$cycloalkyl)$C_0$–$C_3$alkoxy, vii) mono- or di-($C_1$–$C_3$alkyl)amino, viii)$C_1$–$C_3$haloalkyl, and ix) $C_1$–$C_3$haloalkoxy,
wherein each of iii, iv, v, vi, and vii is unsubstituted or substituted by 1–3 groups independently chosen from hydroxy, amino, cyano, and halogen;
$R_4$ is selected from the group consisting of i) hydrogen, ii) $C_1$–$C_3$alkyl, iii) $C_1$–$C_3$alkoxy, iv) ($C_3$–$C_7$cycloalkyl)$C_0$–$C_3$alkyl, v) ($C_3$–$C_7$cycloalkyl)$C_0$–$C_3$alkoxy, vi) mono- or di-($C_1$–$C_3$alkyl)amino, vii)$C_1$–$C_3$haloalkyl, and viii) $C_1$–$C_3$haloalkoxy, wherein each of ii, iii, iv, v, and vi is unsubstituted or substituted by 1–3 groups independently chosen from hydroxy, amino, cyano, and halogen.

7. A compound or salt according to claim 6, wherein $R_2$ is $OR_C$, $NHR_C$, or $NR_{CRD}$; and
$R_D$ is independently selected at each occurrence from: hydrogen, and straight, branched, and cyclic alkyl groups, and (cycloalkyl)alkyl groups, having 1 to 8 carbon atoms, and containing zero or one or more double or triple bonds, each of which 1 to 8 carbon atoms may be further substituted with one or more substituent(s) independently selected from oxo, hydroxy, halogen, cyano, amino, $C_1$–$C_6$alkoxy, and mono- and di ($C_1$–$C_6$alkyl)amino.

8. A compound or salt according to claim 7, wherein $R_C$ and $R_D$, are the same or different, and are independently selected at each occurrence from: straight, branched, and cyclic alkyl groups, and (cycloalkyl)alkyl groups, having 1 to 8 carbon atoms, containing zero or one double or triple bonds.

9. A compound or salt of Formula II

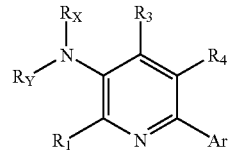

Formula II wherein:
Ar is selected from the group consisting of phenyl or naphthyl, each of which is substituted with up to 5 $R_A$ groups;
$R_1$ is selected from amino, nitro, and mono- or di-$C_1$–$C_6$carbhydryl$_1$amino, where each carbhydryl$_1$ is independently straight or branched, contains 0 or 1 double or triple bonds, and is unsubstituted or substituted with one or more substituents independently chosen from halogen, hydroxy, oxo, cyano, $C_1$–$C_4$alkoxy, amino, and mono- or di-($C_1$–$C_4$alkyl) amino;

$R_1$ $R_3$, and $R_4$ are independently selected from hydrogen, halogen, hydroxy, amino, nitro, $C_1$–$C_6$carbhydryl$_1$, $C_1$–$C_6$carbhydryl$_1$-O—, mono- or di-$C_1$–$C_6$carbhydryl$_1$amino, $C_3$–$C_7$cycloalkyl$_2$ ($C_0$–$C_4$carbhydryl$_1$), $C_3$–$C_7$cycloalkenyl$_2$ ($C_0$–$C_4$carbhydryl$_1$), $C_3$–$C_7$cycloalkyl$_2$ ($C_0$–$C_4$carbhydryl$_1$)-O—, $C_3$–$C_7$cycloalkenyl$_2$ ($C_0$–$C_4$carbhydryl$_1$)-O—, halo$C_1$–$C_6$carbhydryl$_1$, halo$C_1$–$C_6$carbhydryl$_1$-O—, and —S(O)$_n$($C_1$–$C_6$carbhydryl$_1$), where each carbhydryl$_1$ is independently straight or branched, contains 0 or 1 double or triple bonds, and is unsubstituted or substituted with one or more substituents independently chosen from halogen, hydroxy, oxo, cyano, $C_1$–$C_4$alkoxy, amino, and mono- or di-($C_1$–$C_4$alkyl)amino, and where each $C_3$–$C_7$cycloalkyl$_2$ and $C_3$–$C_7$cycloalkenyl$_2$ is optionally substituted by one or more substituents independently chosen from halogen, hydroxy, oxo, cyano, $C_1$–$C_4$alkoxy, amino, and mono- or di-($C_1$–$C_4$alkylamino;

X is independently selected at each occurrence from the group consisting of —CH$_2$—, —CHR$_D$—, —O—, —C(=O)—, —C(=O)O—, —S(O)$_n$—, —NH—, —NR$_D$—, —C(=O)NH—, —C(=O)NR$_D$—, —S(O)$_n$NH—, —S(O)$_n$NR$_D$—, —OC(=S)S—, —NHC(=O)—, —NR$_D$C(=O)—, —NHS(O)$_n$—, and —NR$_D$S(O)$_n$—;

Y and Z are independently selected at each occurrence from: 3- to 7-membered carbocyclic or heterocyclic groups, which are saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, mono- or di-($C_1$–$C_4$alkyl)amino, and —S(O)$_n$(alkyl), wherein said 3- to 7-membered heterocyclic groups contain from 1 to 3 heteroatom(s) independently selected from N, O, and S, with remaining ring members being carbon;

R$_A$ is independently selected at each occurrence from halogen, cyano, nitro, halo($C_1$–$C_6$)alkyl, halo ($C_1$–$C_6$alkoxy, hydroxy, amino, $C_1$–$C_6$alkyl substituted with 0–2 R$_B$, $C_2$–$C_6$alkenyl substituted with 0–2 R$_B$, $C_2$–$C_6$alkynyl substituted with 0–2 R$_B$, $C_3$–$C_7$cycloalkyl substituted with 0–2 R$_B$, ($C_3$–$C_7$cycloalkyl)$C_1$–$C_4$alkyl substituted with 0–2 R$_B$, $C_1$–$C_6$alkoxy substituted with 0–2 R$_B$, —NH ($C_1$–$C_6$alkyl) substituted with 0–2 R$_B$, —N($C_1$–$C_6$alkyl)($C_1$–$C_6$alkyl) where each $C_1$–$C_6$alkyl is independently substituted with 0–2 R$_B$, —XR$_C$, and Y;

R$_B$ is independently selected at each occurrence from halogen, hydroxy, cyano, amino, $C_1$–$C_4$alkyl, $C_1$–$C_4$alkoxy, mono- or di-($C_1$–$C_4$alkyl)amino, —S(O)$_n$(alkyl), halo($C_1$–$C_4$)alkyl, halo($C_1$–$C_4$)alkoxy, —CO($C_1$–$C_4$alkyl), —CONH(alkyl), —CON ($C_1$–$C_4$alkyl)($C_1$–$C_4$alkyl), —XR$_C$, and Y;

R$_C$ and R$_D$, are the same or different, and are independently selected at each occurrence from: hydrogen, and straight, branched, and cyclic alkyl groups, and (cycloalkyl)alkyl groups, having 1 to 8 carbon atoms, and containing zero or one double or triple bonds, each of which 1 to 8 carbon atoms may be further substituted with one or more substituent(s) independently selected from oxo, hydroxy, halogen, cyano, amino, $C_1$–$C_6$alkoxy, and mono or di-($C_1$–$C_6$alkyl)amino; —NHC(=O)($C_1$–$C_6$alkyl), —N($C_1$–$C_6$alkyl)C(=O) ($C_1$–$C_6$alkyl), —NHS(O)$_n$($C_1$–$C_6$alkyl), —S(O)$_n$ ($C_1$–$C_6$alkyl), —S(O)$_n$NH($C_1$–$C_6$alkyl), —S(O)$_n$ ($C_1$–$C_6$alkyl)($C_1$–$C_6$alkyl), and Z; and n is independently selected at each occurrence from 0, 1, and 2;

R$_X$ and R$_Y$ are the same or different and are independently selected from:

a) hydrogen,
b) —(C=O)$C_1$–$C_8$alkyl; and
c) straight or branched alkyl groups, cycloalkyl groups) or (cycloalkyl)alkyl groups, having 1 to 8 carbon atoms and containing zero double or triple bonds, each of which 1 to 8 carbon atoms may be further substituted with one or more substituent(s) independently selected from:
   i) halogen, hydroxy, amino, cyano, $C_1$–$C_4$alkyl, $C_1$–$C_4$alkoxy, and mono- or di-$C_1$–$C_4$alkyl)amino, and
   ii) 3- to 7-membered carbocyclic or heterocyclic groups which are saturated, partially unsaturated, or aromatic, which may be further substituted with one or more substituents independently selected from halogen, hydroxy, amino, cyano, $C_1$–$C_4$alkyl, $C_1$–$C_4$alkoxy, and mono- or di-($C_1$–$C_4$alkyl)amino, wherein said 3- to 7-membered heterocyclic groups contain front 1 to 3 heteroatom(s) independently selected from N, O, and S, with remaining ring members being carbon, with the proviso that not all of $R_1$, $R_3$, and $R_4$ are unsubstituted alkyl and not all of $R_1$, $R_3$, and $R_4$ are hydrogen.

10. A compound or salt according to claim 9, wherein:

R$_X$ and R$_Y$ are the same or different and are independently selected from:

a) hydrogen,
b) (C=O)$C_1$–$C_8$alkyl, and
c) straight or branched alkyl groups, cycloalkyl groups, or (cycloalkyl)alkyl groups, having 1 to 8 carbon atoms and containing zero double or triple bonds, each of which 1 to 8 carbon atoms may be further substituted with one or more substituent(s) independently selected from: halogen, hydroxy, amino, cyano, $C_1$–$C_4$alkyl, $C_1$–$C_4$alkoxy, and mono- or di- ($C_1$–$C_4$alkyl)amino, Ar is phenyl which is mono-, di-, or tri-substitutcd with R$_A$, with the proviso that at least one of the positions ortho to the point of attachment of Ar shown in Formula II is substituted;

X is independently selected at each occurrence from the group consisting of —CH$_2$—, —CHR$_D$—, —O—, —C(=O)—, —C(=O)O—, —NH—, —NR$_D$—, —C(=O)NH—, —C(=O)NR$_D$—, —NHC(=O)—, and —NR$_D$C(=O)—;

Y and Z are independently selected at each occurrence from: 3- to 7-membered carbocyclic or heterocyclic groups, which are saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, mono- or di-($C_1$–$C_4$alkyl)amino, wherein said 3- to 7-membered heterocyclic groups contain from 1 to 3 heteroatom(s) independently selected from N, O, and S, with remaining ring members being carbon; and $R_C$ and $R_D$, are the same or different, and are independently selected at each occurrence from: hydrogen, and straight, branched, and cyclic alkyl groups, and (cycloalkyl)alkyl groups, having 1 to 8 carbon atoms, and containing zero or one double or triple bonds, each or which 1 to 8 carbon atoms may be further substituted with one or more substituent(s) independently selected from oxo, hydroxy, halogen, cyano, amino, $C_1$–$C_6$alkoxy, mono- or di-$C_1$–$C_4$alkyl)amino, —NHC(=O)($C_1$–$C_6$alkyl), —N($C_1$–$C_6$alkyl)C(=O)($C_1$–$C_6$alkyl), and Z.

11. A compound or salt according to claim 9, wherein:

$R_1$ $R_3$ and $R_4$ are independently selected from the group consisting of i) hydrogen, ii) halogen, iii) $C_1$–$C_4$alkyl, iv) $C_1$–$C_3$alkoxy, v) ($C_3$–$C_7$cycloalkyl)$C_0$–$C_3$alkyl, vi) $C_3$–$C_7$cycloalkyl)$C_0$–$C_3$alkoxy, vii) mono- or di-($C_1$–$C_3$alkyl)amino, viii)$C_1$–$C_3$haloalkyl, and ix) $C_1$–$C_3$haloalkoxy, wherein each of iii, iv, v, vi, and vii is unsubstituted or substituted by 1–3 groups independently chosen from halogen, hydroxy, oxo, cyano, $C_1$–$C_4$alkoxy, amino, and mono- or di-($C_1$–$C_4$)amino.

12. A compound or salt according to claim 10, wherein $R_X$ is a) hydrogen or b) a straight or branched alkyl group, a cycloalkyl groups, or (cycloalkyl)alkyl group, each of which groups having 1 to 8 carbon atoms and containing zero double or triple bonds, each of which 1 to 8 carbon atoms may be further substituted with one or more substituent(s) independently selected from halogen, hydroxy, amino, cyano, $C_1$–$C_4$alkyl, $C_1$–$C_4$alkoxy, and mono- or di-($C_1$–$C_4$)alkylamino;

$R_Y$ is a straight or branched alkyl group, a cycloalkyl groups, or (cycloalkyl)alkyl group, each of which groups having 1 to 8 carbon atoms and containing zero double or triple bonds, each of which 1 to 8 carbon atoms may be further substituted with one or more substituent(s) independently selected from halogen, hydroxy, amino, cyano, $C_1$–$C_4$alkyl, $C_1$–$C_4$alkoxy, and mono- or di-($C_1$–$C_4$)alkylamino;

Ar is phenyl, mono-, di-, or tri-substituted with substituents independently selected at each occurrence from halogen, cyano, nitro, halo($C_1$–$C_6$)alkyl, halo($C_1$–$C_6$)alkoxy, hydroxy, amino, $C_1$–$C_4$alkyl, $C_2$–$C_6$alkenyl, $C_2$–$C_6$alkynyl, $C_3$–$C_7$cycloalkyl, ($C_3$–$C_7$cycloalkyl) $C_1$–$C_4$alkyl, $C_1$–$C_6$alkoxy, and mono- or di-($C_1$–$C_6$alkyl)amino; and $R_1$ $R_3$ and $R_4$ are independently selected from the group consisting of hydrogen, halogen, $C_1$–$C_4$alkyl, $C_1$–$C_3$alkoxy, ($C_3$–$C_7$cycloalkyl)$C_0$–$C_3$alkyl, ($C_3$–$C_7$cycloalkyl)$C_0$–$C_3$alkoxy, mono- or di-($C_1$–$C_3$alkyl)amino, $C_1$–$C_3$haloalkyl, and $C_1$–$C_3$haloalkoxy.

13. A compound or salt according to claim 12, wherein $R_X$ is hydrogen, $C_1$–$C_6$alkyl, a $C_3$–$C_7$cycloalkyl, or ($C_3$–$C_7$cycloalkyl) $C_1$–$C_4$alkyl;

$R_Y$ a $C_1$–$C_6$alkyl, a $C_3$–$C_7$cycloalkyl, or ($C_3$–$C_7$cycloalkyl) $C_1$–$C_4$alkyl;

Ar is phenyl, mono-, di-, or tri-substituted with substituents independently selected at each occurrence from halogen, halo($C_1$–$C_2$)alkyl, halo($C_1$–$C_2$)alkoxy, hydroxy, amino, $C_1$–$C_3$alkyl, $C_1$–$C_2$alkoxy, and mono- or di-($C_1$–$C_2$alkyl)amino; and $R_4$ is selected from the group consisting of hydrogen, halogen, $C_1$–$C_3$alkyl, $C_1$–$C_3$alkoxy, mono- or di-($C_1$–$C_3$alkyl)amino, $C_1$–$C_3$haloalkyl and $C_1$–$C_3$haloalkoxy; and $R_3$ is hydrogen, halogen, or methyl.

14. A compound or salt according to claim 9 of Formula III:

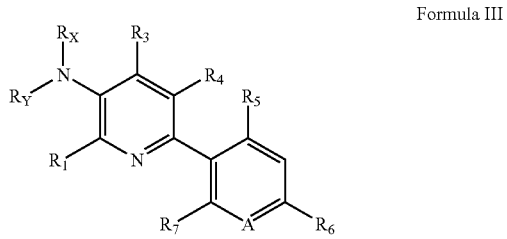

Formula III wherein:

A is CH; and $R_5$, $R_6$, and $R_7$ are independently i) hydrogen, halogen, cyano, halo($C_1$–$C_4$)alkyl, halo($C_1$–$C_4$)alkoxy, hydroxy, amino, $C_1$–$C_6$alkyl, $C_1$–$C_6$alkoxy, ($C_1$–$C_4$alkoxy) $C_1$–$C_4$alkoxy, or mono- or di($C_1$–$C_4$alkyl)amino, or ii) $C_1$–$C_6$alkyl or $C_1$–$C_6$alkoxy, each of which is further substituted with a 3- to 7-membered carbocyclic or heterocyclic groups which is saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, and mono- or di-($C_1$–$C_4$alkyl)amino;

wherein at least one of $R_5$ and $R_7$ is not hydrogen.

15. A compound or salt according to claim 14, wherein: $R_X$ is a) hydrogen or b) a straight or branched alkyl group, a cycloalkyl group, or (cycloalkyl)alkyl group, having 1 to 8 carbon atoms and containing zero double or triple bonds, each of which 1 to 8 carbon atoms may be further substituted with one or more substituent(s) independently selected from halogen, hydroxy, amino, cyano, $C_1$–$C_4$alkyl, $C_1$–$C_4$alkoxy, and mono- or di-($C_1$–$C_4$)alkylamino;

$R_Y$ is a straight or branched alkyl group, a cycloalkyl groups, or (cycloalkyl)alkyl group, each having 1 to 8 carbon atoms and containing zero double or triple bonds, each of which 1 to 8 carbon atoms may be further substituted with one or more substituent(s) independently selected from halogen, hydroxy, amino, cyano, $C_1$–$C_4$alkyl, $C_1$–$C_4$alkoxy, and mono- or di-($C_1$–$C_4$)alkylamino;

$R_4$ is selected from the group consisting of hydrogen, halogen, $C_1$–$C_4$alkoxy, halo($C_1$–$C_4$)alkyl, halo($C_1$–$C_4$) alkoxy, and $C_1$–$C_6$alkyl, which $C_1$–$C_6$alkyl is unsubstituted or substituted by one to three substituents independently selected from hydroxy, oxo, cyano, $C_1$–$C_4$alkoxy, amino, and mono- or di($C_1$–$C_4$)alkylamino, $R_3$ is hydrogen, halogen, methyl, or methoxy; and $R_5$, $R_6$, and $R_7$ are independently selected from hydrogen, halogen, cyano, halo($C_1$–$C_4$)alkyl, halo($C_1$–$C_4$)alkoxy, hydroxy, amino, $C_1$–$C_6$alkyl, $C_1$–$C_6$alkoxy, ($C_1$–$C_4$alkoxy)$C_1$–$C_4$alkoxy, and mono- or di($C_1$–$C_4$alkyl)amino.

16. A compound or salt according to claim 9 of Formula V:

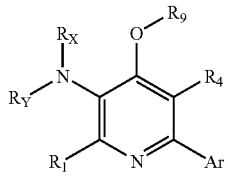

Formula V wherein:

Ar is phenyl, which is mono-, di-, or tri-substituted with $R_4$, with the proviso that at least one of the positions ortho to the point of attachment of Ar shown in Formula V is substituted;

$R_4$ is selected from the group consisting of hydrogen, halogen, $C_1$–$C_4$alkoxy, halo($C_1$–$C_4$)alkyl, halo($C_1$–$C_4$)alkoxy, $C_1$–$C_6$alkyl, and mono- and di-($C_1$–$C_4$alkyl)amino; and $R_9$ is selected from straight or branched alkyl groups, cycloalkyl groups, and (cycloalkyl)alkyl groups, having 1 to 8 carbon atoms and containing zero double or triple bonds, each of which 1 to 8 carbon atoms may be further substituted with one or more substituent(s) independently selected from oxo, hydroxy, halogen, cyano, $C_1$–$C_4$alkoxy, amino, and mono- or di-($C_1$–$C_4$)alkylamino.

17. A compound or salt according to claim 16 of Formula VI:

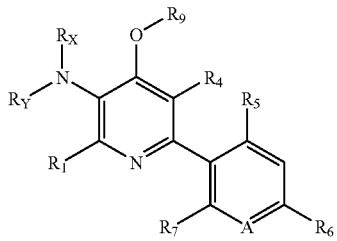

Formula VI wherein, A is CH; and $R_5$, $R_6$, and $R_7$ are independently i) hydrogen, halogen, cyano, halo($C_1$–$C_4$)alkyl, halo($C_1$–$C_4$)alkoxy, hydroxy, amino, $C_1$–$C_6$alkyl, $C_1$–$C_6$alkoxy, ($C_1$–$C_4$alkoxy) $C_1$–$C_4$alkoxy, or mono- or di($C_1$–$C_4$alkyl)amino, or ii) $C_1$–$C_6$alkyl or $C_1$–$C_6$alkoxy, each of which is further substituted with a 3- to 7-membered carbocyclic or heterocyclic groups which is saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, and mono- or di-($C_1$–$C_4$alkyl)amino;

wherein at least one of $R_5$ and $R_7$ is not hydrogen.

18. A compound or salt according to claim 16, of Formula VII:

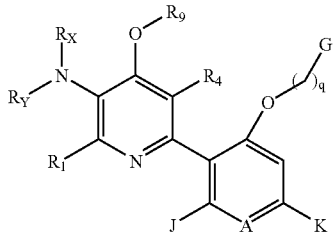

Formula VII wherein:

A is CH;

q is an integer from 1 to 4;

G is hydrogen, hydroxy, $C_1$–$C_4$alkoxy, mono- or di($C_1$–$C_4$alkyl)amino, or a 3- to 7-membered carbocyclic or heterocyclic group which is saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, mono- or di-($C_1$–$C_4$alkyl)amino and —S(O)$_n$(alkyl), wherein said 3- to 7-membered heterocyclic group contains from 1 to 3 heteroatom(s) independently selected from N, O, and S, with remaining ring members being carbon, and n is 0, 1, or 2; and J and K are independently selected from hydrogen, halogen, cyano, halo($C_1$–$C_4$)alkyl, halo($C_1$–$C_4$)alkoxy, hydroxy, amino, $C_1$–$C_6$alkyl, $C_1$–$C_6$alkoxy, ($C_1$–$C_4$alkoxy)$C_1$–$C_4$alkoxy, and mono- or di($C_1$–$C_4$alkyl)amino.

19. A compound or salt according to claim 1 of Formula VIII

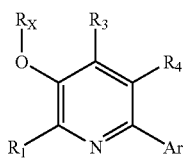

Formula VIII wherein:

$R_X$ is a straight or branched alkyl group, cycloalkyl group, or (cycloalkyl)alkyl group, having 1 to 8 carbon atoms and containing zero double or triple bonds, each which 1 to 8 carbon atoms may be further substituted with one or more substituent(s) independently selected from:

i) halogen, hydroxy, amino, cyano, $C_1$–$C_4$alkyl, $C_1$–$C_4$alkoxy, and mono- or di-($C_1$–$C_4$alkyl)amino, ii) 3- to 7-membered carbocyclic or heterocyclic groups which are saturated, partially unsaturated, or aromatic, which may be further substituted with one or more substituents independently selected from halogen, hydroxy, amino, cyano, $C_1$–$C_4$alkyl, $C_1$–$C_4$alkoxy, and mono- or di-($C_1$–$C_4$alkyl)amino, wherein said 3- to 7-membered heterocyclic groups contain from 1 to 3 heteroatom(s) independently selected from N, O, and S, with remaining ring members being carbon.

20. A compound or salt according to claim 19, wherein:

Ar is phenyl, which is mono-, di-, or tri-substituted with $R_4$, with the proviso that at least one of the positions ortho to the point of attachment of Ar shown in Formula VIII is substituted;

X is independently selected at each occurrence from the group consisting of —$CH_2$—, —$CHR_D$—, —O—, —C(=O)—, —C(=O)O—, —NH—, —$NR_D$—, —C(=O)NH—, —C(=O)$NR_D$—, —NHC(=O)—, and —$NR_D$C(=O)—;

Y and Z are independently selected at each occurrence from: 3- to 7-membered carbocyclic or heterocyclic groups which are saturated, partially unsaturated, or aromatic, which may be further substituted with one or more substituents independently selected from halogen, oxo, hydroxy, amino, cyano, $C_1$–$C_4$alkyl, —O($C_1$–$C_4$alkyl), and —NH($C_1$–$C_4$alkyl), —N($C_1$–$C_4$alkyl)($C_1$–$C_4$alkyl), wherein said 3- to 7-membered hererocyclic groups contain from 1 to 3 heteroatom(s) independently selected from N, O, and S, with remaining ring members being carbon;

$R_D$ is independently selected at each occurrence from: hydrogen, and straight, branched, and cyclic alkyl groups, and (cycloalkyl)alkyl groups, having 1 to 8 carbon atoms, and containing zero or one double or triple bonds, each of which 1 to 8 carbon atoms may be further substituted with one or more substituent(s) independently selected from oxo, hydroxy, halogen, cyano, amino, $C_1$–$C_6$alkoxy, mono- or di-($C_1$–$C_4$alkyl)amino, —NHC(=O)($C_1$–$C_6$alkyl), —N($C_1$–$C_6$alkyl)C(=O)($C_1$–$C_6$alkyl), and Z.

21. A compound or salt according to claim 19, wherein:

$R_1$ is mono- or di-($C_1$–$C_3$alkyl)amino, which is unsubstituted or substituted with 1 to 3 substituents independently chosen from halogen, hydroxy, oxo, cyano, $C_1$–$C_4$alkoxy, amino, and mono- or di-($C_1$–$C_3$)amino;

$R_3$ is selected from the group consisting of i) hydrogen, ii) halogen, iii) $C_1$–$C_4$alkyl, iv) $C_1$–$C_3$alkoxy, v) ($C_3$–$C_7$cycloalkyl)$C_0$–$C_3$alkyl, vi) ($C_3$–$C_7$cycloalkyl)$C_0$–$C_3$alkoxy, vii) mono- or di-($C_1$–$C_3$alkyl)amino, viii) $C_1$–$C_3$haloalkyl, and ix) $C_1$–$C_3$haloalkoxy, wherein each of iii, iv, v, vi, and vii is unsubstituted or substituted by 1–3 groups independently chosen from halogen, hydroxy, oxo, cyano, $C_1$–$C_4$alkoxy, amino, and mono- or di-($C_1$–$C_4$alkyl)amino; and $R_4$ is selected from the group consisting of i) hydrogen, ii) $C_1$–$C_4$alkyl, iii) $C_1$–$C_3$alkoxy, iv) ($C_3$–$C_7$cycloalkyl)$C_0$–$C_3$alkyl, v) ($C_3$–$C_7$cycloalkyl)$C_0$–$C_3$alkoxy, vi) mono- or di-($C_1$–$C_3$alkyl)amino, vii) $C_1$–$C_3$haloalkyl, and viii) $C_1$–$C_3$haloalkoxy, wherein each of ii, iii, iv, v, and vi, is unsubstituted or substituted by 1–3 groups independently chosen from halogen, hydroxy, oxo, cyano, $C_1$–$C_4$alkoxy, amino, and mono- or di-($C_1$–$C_4$alkyl)amino.

22. A compound or salt according to claim 20, wherein

Ar is phenyl, mono-, di-, or tri-substituted with substituents independently selected at each occurrence from halogen, cyano, nitro, halo($C_1$–$C_6$alkyl), halo($C_1$–$C_6$)alkoxy, hydroxy, amino, $C_3$–$C_6$alkyl, $C_2$–$C_6$alkyenyl, $C_2$–$C_6$alkynyl, $C_3$–$C_7$cycloalkyl, ($C_3$–$C_7$cycloalkyl)$C_1$–$C_4$alkyl, $C_1$–$C_6$alkoxy, and mono- or di-($C_1$–$C_6$alkyl)amino;

$R_1$ is mono- or di-($C_1$–$C_3$alkyl)amino;

$R_3$ is selected from the group consisting of hydrogen, halogen, $C_1$–$C_4$alkyl, $C_1$–$C_3$alkoxy, ($C_3$–$C_7$cycloalkyl)$C_0$–$C_3$alkyl, ($C_3$–$C_7$cycloalkyl)$C_0$–$C_3$alkoxy, mono- or di-($C_1$–$C_3$alkyl)amino, $C_1$–$C_3$haloalkyl, and $C_1$–$C_3$haloalkoxy; and $R_4$ is selected from the group consisting of hydrogen, halogen, $C_1$–$C_4$alkyl, $C_1$–$C_3$alkoxy, $C_3$–$C_7$cycloalkyl)$C_0$–$C_3$alkyl, ($C_3$–$C_7$cycloalkyl)$C_0$–$C_3$alkoxy, mono- or di-($C_1$–$C_3$alkyl)amino, $C_1$–$C_3$haloalkyl, and $C_1$–$C_3$haloalkoxy.

23. A compound or salt according to claim 22, wherein $R_X$ is a $C_1$–$C_6$alkyl, $C_3$–$C_7$cycloalkyl, or ($C_3$–$C_7$cycloalkyl) $C_1$–$C_4$alkyl group;

Ar is phenyl, mono-, di-, or tri-substituted with substituents independently selected at each occurrence from halogen, halo($C_1$–$C_2$)alkyl, halo($C_1$–$C_2$)alkoxy, hydroxy, amino, $C_1$–$C_3$alkyl, $C_1$–$C_2$alkoxy, and mono- or di-($C_1$–$C_2$alkyl)amino; and $R_4$ is selected from the group consisting of hydrogen $C_1$–$C_3$alkyl, $C_1$–$C_3$alkoxy, mono- or di-($C_1$–$C_3$alkyl) amino, $C_1$–$C_3$haloalkyl, and $C_1$–$C_3$haloalkoxy; and $R_3$ is hydrogen, halogen, or methyl.

24. A compound or salt according to claim 19 of Formula IX:

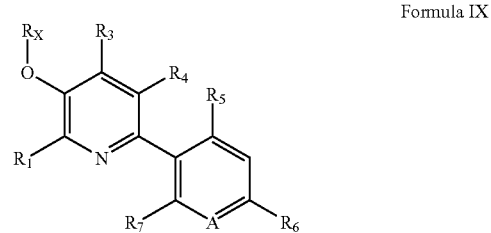

Formula IX wherein:

A is CH;

$R_1$ is mono- or di-($C_1$–$C_4$alkyl)amino, which is unsubstituted or substituted with 1 to 3 substituents independently chosen from halogen, hydroxy, oxo, cyano, $C_1$–$C_4$alkoxy, amino, and mono- or di-($C_1$–$C_3$alkyl) amino; and $R_5$, $R_6$, and $R_7$ are independently i) hydrogen, halogen, cyano, halo($C_1$–$C_4$)alkyl, halo ($C_1$–$C_4$)alkoxy, hydroxy, amino, $C_1$–$C_6$alkyl, $C_1$–$C_6$alkoxy, ($C_1$–$C_4$alkoxy) $C_1$–$C_4$alkoxy, or mono- or di($C_1$–$C_4$alkyl)amino, or ii) $C_1$–$C_6$alkyl or $C_1$–$C_6$alkoxy, each of which is further substituted with a 3- to 7-membered carbocyclic or heterocyclic groups which is saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, and mono- or di-($C_1$–$C_4$alkyl)amino, wherein said 3- to 7-membered heterocyclic group contains from 1 to 3 heteroatom(s) independently selected from N, O, and S, with remaining ring members being carbon;

wherein at least one $R_5$ and $R_7$ is not hydrogen.

25. A compound or salt according to claim 24, wherein:

$R_X$ is a straight or branched alkyl group, a cycloalkyl group, or (cycloalkyl)alkyl group, having 1 to 8 carbon atoms and containing zero double or triple bonds, each of which 1 to 8 carbon atoms may be further substituted with one or more substituent(s) independently selected from halogen, hydroxy, amino, cyano, $C_1$–$C_4$alkyl, $C_1$–$C_4$alkoxy, and mono- or di-($C_1$–$C_4$)alkylamino;

$R_4$ is selected from the group consisting of hydrogen, halo($C_1$–$C_4$)alkyl, halo($C_1$–$C_4$)alkoxy, and $C_1$–$C_6$alkyl, which $C_1$–$C_6$alkyl is unsubstituted or substituted by one to three substituents independently selected from hydroxy, oxo, cyano, $C_1$–$C_4$alkoxy, amino, and mono- or di($C_1$–$C_4$)alkylamino, $R_3$ is hydrogen, halogen, methyl, or methoxy; and $R_5$, $R_6$, and $R_7$ are independently selected from hydrogen, halogen, cynno, halo($C_1$–$C_4$)alkyl, halo($C_1$–$C_4$)alkoxy, hydroxy, amino, $C_1$–$C_6$alkyl, $C_1$–$C_6$alkoxy, ($C_1$–$C_4$alkoxy)$C_1$–$C_4$alkoxy, and mono- or di($C_1$–$C_4$alkyl)amino.

26. A pharmaceutical composition comprising a pharmaceutically acceptable carrier and a compound or salt of claim 1.

27. A pharmaceutical composition according to claim 26, wherein the composition is formulated as an injectable fluid, an aerosol, a cream, a gel, a tablet, a pill, a capsule, a syrup or a transdermal patch.

28. A package comprising a pharmaceutical composition of claim 26 in a container and further comprising indicia comprising at least one of:

instructions for using the composition to treat a patient suffering from anxiety, or instructions for using the composition to treat a patient suffering from stress, or instructions for using the composition to treat a patient suffering from depression.

29. A package comprising a pharmaceutical composition of claim 26 in a container and further comprising at least one of: instructions for using the composition to treat a patient suffering from irritable bowel syndrome or instructions for using the composition to treat a patient suffering from Crohn's disease.

* * * * *